(12) United States Patent
Vaughan

(10) Patent No.: US 10,984,899 B2
(45) Date of Patent: *Apr. 20, 2021

(54) PLATFORM AND SYSTEM FOR DIGITAL PERSONALIZED MEDICINE

(71) Applicant: Cognoa, Inc., Palo Alto, CA (US)

(72) Inventor: Brent Vaughan, Portola Valley, CA (US)

(73) Assignee: COGNOA, INC., Palo Alto, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/068,682

(22) Filed: Oct. 12, 2020

(65) Prior Publication Data

US 2021/0035668 A1 Feb. 4, 2021

Related U.S. Application Data

(63) Continuation of application No. 16/155,798, filed on Oct. 9, 2018, now Pat. No. 10,839,950, which is a (Continued)

(51) Int. Cl.
*G16H 10/60* (2018.01)
*G16H 10/20* (2018.01)
(Continued)

(52) U.S. Cl.
CPC ............. *G16H 10/60* (2018.01); *A61B 5/168* (2013.01); *A61B 5/4088* (2013.01);
(Continued)

(58) Field of Classification Search
CPC ..... A61B 5/0022; A61B 5/168; A61B 5/4088; A61B 5/4833; A61B 5/486; A61B 5/7267;
(Continued)

(56) References Cited

U.S. PATENT DOCUMENTS 5,722,418 A 3/1998 Bro
6,425,764 B1 7/2002 Lamson
(Continued)

FOREIGN PATENT DOCUMENTS

CN 1918575 A 2/2007
CN 101499078 A 8/2009
(Continued)

OTHER PUBLICATIONS

Bailey, et al. Autism as a strongly genetic disorder: evidence from a British twin study. Psychol Med. Jan. 1995;25(1):63-77.
(Continued)

*Primary Examiner* — Neal Sereboff
(74) *Attorney, Agent, or Firm* — Wilson Sonsini Goodrich & Rosati

(57) ABSTRACT

The digital personalized medicine system uses digital data to assess or diagnose symptoms of a subject to provide personalized or more appropriate therapeutic interventions and improved diagnoses. The use of prioritized questions and answers with associated feature importance can be used to assess mental function and allow a subject to be diagnosed with fewer questions, such that diagnosis can be repeated more often and allow the dosage to be adjusted more frequently. Pharmacokinetics of the subject can be estimated based on demographic data and biomarkers or measured, in order to determine a treatment plan for the subject. Also, biomarkers can be used to determine when the patient may be at risk for experiencing undesirable side effects and the treatment plan adjusted accordingly.

20 Claims, 33 Drawing Sheets

Related U.S. Application Data continuation of application No. PCT/US2018/017354, filed on Feb. 8, 2018.

(60) Provisional application No. 62/457,130, filed on Feb. 9, 2017.

(51) Int. Cl.
  *G16H 50/20* (2018.01)
  *G16H 50/70* (2018.01)
  *G16H 20/10* (2018.01)
  *G16H 20/70* (2018.01)
  *A61B 5/00* (2006.01)
  *A61B 5/16* (2006.01)
  *G06N 20/00* (2019.01)
  *G16H 80/00* (2018.01)

(52) U.S. Cl.
  CPC .......... *A61B 5/4833* (2013.01); *A61B 5/7267* (2013.01); *G16H 10/20* (2018.01); *G16H 20/10* (2018.01); *G16H 20/70* (2018.01); *G16H 50/20* (2018.01); *G16H 50/70* (2018.01); *A61B 5/0022* (2013.01); *A61B 5/486* (2013.01); *G06N 20/00* (2019.01); *G16H 80/00* (2018.01)

(58) Field of Classification Search
  CPC ........ G16H 10/20; G16H 10/60; G16H 20/10; G16H 20/70; G16H 50/20; G16H 50/70; G16H 80/00
  See application file for complete search history.

(56) References Cited

U.S. PATENT DOCUMENTS

| | | | |
|---|---|---|---|
| 6,569,093 | B2 | 5/2003 | Iliff |
| 6,957,202 | B2 | 10/2005 | Skaanning et al. |
| 7,043,439 | B2 | 5/2006 | Jost et al. |
| 7,155,421 | B1 | 12/2006 | Haldar |
| 7,311,666 | B2 | 12/2007 | Stupp et al. |
| 7,958,066 | B2 | 6/2011 | Pinckney et al. |
| 7,974,872 | B2 | 7/2011 | Katayama et al. |
| 8,024,332 | B2 | 9/2011 | Cao et al. |
| 8,655,817 | B2 | 2/2014 | De Bruin et al. |
| 9,443,199 | B2 | 9/2016 | Pinckney et al. |
| 9,443,205 | B2 | 9/2016 | Wall |
| 10,311,645 | B1 | 6/2019 | Ravindran et al. |
| 10,478,112 | B2 | 11/2019 | Wall |
| 2001/0034615 | A1 | 10/2001 | Wilkinson et al. |
| 2001/0036444 | A1* | 11/2001 | Placke .................. A61K 31/00 424/43 |
| 2002/0002325 | A1 | 1/2002 | Iliff |
| 2002/0019747 | A1 | 2/2002 | Ware et al. |
| 2002/0035486 | A1 | 3/2002 | Huyn et al. |
| 2002/0042786 | A1 | 4/2002 | Scarborough et al. |
| 2003/0032069 | A1 | 2/2003 | Muraca |
| 2003/0191680 | A1 | 10/2003 | Dewar |
| 2004/0015337 | A1 | 1/2004 | Thomas et al. |
| 2004/0103001 | A1 | 5/2004 | Mazar et al. |
| 2004/0147840 | A1 | 7/2004 | Duggirala et al. |
| 2004/0265784 | A1 | 12/2004 | Stout |
| 2005/0142524 | A1 | 6/2005 | Simon et al. |
| 2005/0176057 | A1 | 8/2005 | Bremer et al. |
| 2005/0209785 | A1 | 9/2005 | Wells et al. |
| 2005/0216243 | A1 | 9/2005 | Graham et al. |
| 2005/0260549 | A1 | 11/2005 | Feierstein et al. |
| 2006/0009683 | A1 | 1/2006 | Sakai et al. |
| 2006/0059145 | A1 | 3/2006 | Henschke et al. |
| 2006/0078856 | A1 | 4/2006 | Kellman |
| 2006/0282306 | A1 | 12/2006 | Thissen-Roe |
| 2007/0118399 | A1 | 5/2007 | Avinash et al. |
| 2007/0207449 | A1 | 9/2007 | Feierstein |
| 2008/0016024 | A1 | 1/2008 | Andoh et al. |
| 2009/0016559 | A1 | 1/2009 | Cleary |
| 2009/0083075 | A1 | 3/2009 | Henschke et al. |
| 2009/0137923 | A1 | 5/2009 | Suffin et al. |
| 2009/0182578 | A1 | 7/2009 | Ozersky |
| 2009/0259494 | A1 | 10/2009 | Feder et al. |
| 2010/0068687 | A1 | 3/2010 | Bertelsen |
| 2010/0177950 | A1 | 7/2010 | Donovan et al. |
| 2010/0184093 | A1 | 7/2010 | Donovan et al. |
| 2010/0189818 | A1 | 7/2010 | Tsai |
| 2010/0280760 | A1 | 11/2010 | Pi et al. |
| 2011/0119212 | A1 | 5/2011 | De Bruin et al. |
| 2011/0145161 | A1 | 6/2011 | Scarborough et al. |
| 2011/0184379 | A1 | 7/2011 | Van Antwerp et al. |
| 2012/0059282 | A1 | 3/2012 | Agichtein et al. |
| 2012/0102405 | A1 | 4/2012 | Zuckerman et al. |
| 2012/0270199 | A1 | 10/2012 | Malik |
| 2013/0159010 | A1 | 6/2013 | Paty et al. |
| 2013/0178731 | A1 | 7/2013 | Bosl |
| 2013/0184603 | A1 | 7/2013 | Rothman |
| 2013/0184792 | A1 | 7/2013 | Simon et al. |
| 2013/0262357 | A1 | 10/2013 | Amarasingham et al. |
| 2013/0267441 | A1* | 10/2013 | Momeni .................. A61P 21/00 506/12 |
| 2014/0006319 | A1 | 1/2014 | Anand et al. |
| 2014/0052474 | A1 | 2/2014 | Madan et al. |
| 2014/0074848 | A1 | 3/2014 | Kettunen et al. |
| 2014/0141983 | A1* | 5/2014 | Singh .................. C12Q 1/6883 506/7 |
| 2014/0219986 | A1 | 8/2014 | Greene et al. |
| 2014/0279746 | A1 | 9/2014 | De Bruin et al. |
| 2014/0304200 | A1 | 10/2014 | Wall |
| 2014/0336539 | A1 | 11/2014 | Torres et al. |
| 2015/0004588 | A1 | 1/2015 | Vats et al. |
| 2015/0006192 | A1 | 1/2015 | Sudharsan et al. |
| 2015/0119437 | A1 | 4/2015 | Clark et al. |
| 2015/0154372 | A1* | 6/2015 | Soenksen ................. G06F 19/00 705/2 |
| 2015/0197543 | A1 | 7/2015 | Glass et al. |
| 2015/0315182 | A1 | 11/2015 | Lee et al. |
| 2016/0046990 | A1 | 2/2016 | Hensel |
| 2016/0135706 | A1 | 5/2016 | Sullivan et al. |
| 2016/0140859 | A1 | 5/2016 | Jiao et al. |
| 2016/0180248 | A1 | 6/2016 | Regan |
| 2016/0209428 | A1* | 7/2016 | Naviaux .............. A61K 31/185 |
| 2016/0342756 | A1 | 11/2016 | Wall |
| 2016/0357924 | A1* | 12/2016 | Jenkins ................. A61B 5/4833 |
| 2017/0035792 | A1* | 2/2017 | Montagnier ........... A61K 31/00 |
| 2017/0069216 | A1 | 3/2017 | Vaughan et al. |
| 2017/0091423 | A1 | 3/2017 | Kumar et al. |
| 2017/0160878 | A1 | 6/2017 | Endo et al. |
| 2017/0262609 | A1 | 9/2017 | Perlroth et al. |
| 2018/0098724 | A1 | 4/2018 | Lu et al. |
| 2018/0184964 | A1 | 7/2018 | Simon et al. |
| 2018/0366144 | A1 | 12/2018 | Ashoori et al. |
| 2019/0019581 | A1 | 1/2019 | Vaughan et al. |
| 2019/0043610 | A1 | 2/2019 | Vaughan |
| 2019/0043618 | A1 | 2/2019 | Vaughan et al. |
| 2019/0043619 | A1 | 2/2019 | Vaughan et al. |
| 2019/0088366 | A1 | 3/2019 | Vaughan et al. |

FOREIGN PATENT DOCUMENTS

| | | |
|---|---|---|
| CN | 101821741 A | 9/2010 |
| CN | 102971755 A | 3/2013 |
| CN | 103473631 A | 12/2013 |
| CN | 104254863 A | 12/2014 |
| CN | 104427932 A | 3/2015 |
| CN | 104956391 A | 9/2015 |
| EP | 0424869 | 2/1991 |
| JP | 2001034688 A | 2/2001 |
| JP | 2015228202 A | 12/2015 |
| WO | WO-9521419 A1 | 8/1995 |
| WO | WO-9705553 A1 | 2/1997 |
| WO | WO-2013062937 A2 | 5/2013 |
| WO | WO-2017106770 A1 | 6/2017 |

(56) References Cited

FOREIGN PATENT DOCUMENTS

| WO | WO-2018090009 A1 | 5/2018 |
|---|---|---|
| WO | WO-2018148365 A1 | 8/2018 |

OTHER PUBLICATIONS

Bernier, et al. Psychopathology, families, and culture: autism. Child Adolesc Psychiatr Clin N Am. Oct. 2010;19(4):855-67.
Berument, et al. Autism screening questionnaire: diagnostic validity. Br J Psychiatry. Nov. 1999; 175:444-51.
Breiman et al.: Chapter 6 Medical diagnosis and prognosis. Classification and regression trees. Chappman & Hall/CRC (1984) (pp. 174-346).
Breiman. Random Forests. Machine Learning 45:5-32 (2001).
Brewer et al., Pinteresce: Exploring Reminiscence as an Incentive to Digital Reciprocity for Older Adults. CSCW'15 Companion (2015).
Cicchetti, et al. Reliability of the ADI-R: multiple examiners evaluate a single case. J Autism Dev Disord. Apr. 2008;38(4):764-70. Epub Dec. 5, 2007.
Cohen. Fast effective rule induction. Proceedings of the Twelfth International Conference on Machine Learning. (pp. 115-123) (1995).
Duda, et al. Clinical Evaluation of a Novel and Mobile Autism Risk Assessment. J Autism Dev Disord. Jun. 2016;46(6):1953-61.
Duda, et al. Testing the accuracy of an observation-based classifier for rapid detection of autism risk Transl Psychiatry. Aug. 12, 2014;4:e424.
Duda, et al. Testing the accuracy of an observation-based classifier for rapid detection of autism risk. Transl Psychiatry. Apr. 28, 2015;5:e556.
Elder et al., Clinical impact of early diagnosis of autism on the prognosis and parent-child relationships. Psychology Research and Behavior Management 10: 283-292 (2017).
EP12844474.2. Search Report and Search Opinion dated Jun. 26, 2015.
European Patent Application No. 17869145.7 Supplementary Search Report dated May 4, 2020.
Fischbach, et al. The Simons Simplex Collection: a resource for identification of autism genetic risk factors. Neuron. Oct. 21, 2010;68(2):192-5.
Fisher et al., DISC Interviewer Manual. Section 2 Computerized Versions of the DISC (2006).
Frank, et al. A simple approach to ordinal prediction. European conference on Maching Learning; Freiburg, Germany, Springer-Verlag 2001:145-156.
Frank, et al. Data mining in bioinformatics using Weka. Bioinformatics. Oct. 12, 2004;20(15):2479-81. Epub Apr. 8, 2004.
Frank et al. Generating accurate rule sets without global optimization. In: Machine Learning: Proceedings of the Fifteenth International Conference: 1998; San Francisco, CA, Morgan Kaufmann Publishers (8 pgs).
Freund, et al. A decision-theoretic generalization of on-line learning and an application to boosting. Journal of computer and system sciences 55.1 (1997): 119-139.
Freund, et al. Experiments with a new boosting algorithm. In: Proceedings of the International Conference on Machine Learning: 1996, San Francisco, Morgan Kautinann: pp. 148-156.
Freund, et al. The alternating decision tree learning algorithm. In: Machine Learning: Proceedings of the Sixteenth International Conference. 1999, pp. 124-133.
Fusaro, et al. The potential of accelerating early detection of autism through content analysis of YouTube videos. PLoS One. Apr. 16, 2014;9(4):e93533.
Gaines, et al. Induction of ripple-down rules applied to modeling large databases. Journal of Intelligent Information Systems 5.3 (1995): 211-228.
Gama. Functional trees. Machine Learning 55:219-250 (2004).
Geschwind et al. The autism genetic resource exchange: a resource for the study of autism and related neuropsychiatric conditions. The American Journal of Human Genetics 69:463-466 (2001).
Gillberg et al. Early detection of autism. Diagnostic instruments for clinicians. European Child & Adolescent Psychiatry 5.2:67-74. (1996).
Golarai, G. et al. Autism and the development of face processing. Clinical Neuroscience Research 6:145-160 (2006).
Gotham, et al. The Autism Diagnostic Observation Schedule: revised algorithms for improved diagnostic validity. J Autism Dev Disord. Apr. 2007;37(4):613-27. Epub Dec. 16, 2006.
Gura, et al. Autism spectrum disorder screening in primary care. J Dev Behav Pediatr. Jan. 2011;32(1):48-51.
Hall et al. The WEKA data mining software: an update. SIGKDD Explorations Newsletter 11:10-18 (2009).
Hirsch, S. et al. Development of a questionnaire weighted scoring system to target diagnostic examinations for asthma in adults: a modelling study. BMC Fam. Pract. 5:30 pp. 1-13 (2004) [E-pub Dec. 17, 2004].
Holmes et al. Multiclass alternating decision trees. Machine learning: ECML 2002. Springer Berlin Heidelberg, (pp. 161-172) (2002).
Holte. Very simple classification rules perform well on most commonly used datasets. Machine learning 11:63-91 (1993).
Howlin. Chapter 3—Identifying and assessing children with autism or asperger syndrome. Children with Autism and Asperger's Syndrome: A Guide for Practitioners and Carers. UK: John Wiley and Sons (1998) (pp. 52-75, 294-321).
Kobak et al. Web-based training in early autism screening: results from a pilot study. Telemed J E Health. Oct. 2011;17(8):640-4.
Kohavi. A study of cross-validation and bootstrap for accuracy estimation and model selection. In: Proceedings IJCAI-95: 1995: Montreal, Morgan Kaufmann, Los Altos, CA: 1137-1143.
Kosmicki, et al. Searching for a minimal set of behaviors for autism detection through feature selection-based machine learning. Transl Psychiatry. Feb. 24, 2015;5:e514.
Landwehr et al. Logistic model trees. Machine Learning 59:161-205 (2005).
Lee et al., How to Create Suitable Augmented Reality Application to Teach Social Skills for Children with ASD. IntechOpen 76476: 119-138 (2018).
Lord et al. Autism Diagnostic Interview-Revised: A revised version of a diagnostic interview for caregivers of individuals with possible pervasive developmental disorders. J Autism Dev Discord 24(5):659-685 (1994).
Lord, et al. Autism diagnostic observation schedule: a standardized observation of communicative and social behavior. J Autism Dev Disord. Jun. 1989;19(2):185-212.
Lord et al. The Autism Diagnostic Observation Schedule—Generic: A Standard Measure of Social and Communication Deficits Associated with the Spectrum of Autism. J Autism Dev Discord 30(3):205-223 (2000).
Martin. Instance-Based learning: Nearest neighbor with generalization. Hamilton, New Zealand, University of Waikato (83 pgs) (1995).
Moore et al. Cached Sufficient Statistics for Efficient Machine Learning with Large Datasets. JAIR 8:67-91 (1998).
Muangnak et al. Classification students with learning disabilities using naive bayes classifier and decision tree. The 6th International Conference on Networked Computing and Advanced Information Management. IEEE, 2010.
Ordonez, C. et al. Machine learning techniques applied to the determination of osteoporosis incidence in post-menopausal women. Mathematical and Computer Modelling, 50:673-679 (2009).
PCT/US2012/061422 International Search Report and Written Opinion dated May 24, 2013.
PCT/US2016/046557 International Search Report and Written Opinion dated Nov. 3, 2016.
PCT/US2016/067358 International Preliminary Report on Patentability dated Jun. 28, 2018.
PCT/US2016/067358 International Search Report and Written Opinion dated Apr. 13, 2017.
PCT/US2017/061552 International Search Report and Written Opinion dated Mar. 26, 2018.

(56) References Cited

OTHER PUBLICATIONS

PCT/US2018/017354 International Preliminary Report on Patentability dated Aug. 13, 2019.
PCT/US2018/017354 International Search Report and Written Opinion dated Apr. 26, 2018.
PCT/US2020/024029 International Search Report and Written Opinion dated Jul. 30, 2020.
Pinto-Martin, et al. Screening strategies for autism spectrum disorders in pediatric primary care. J Dev Behav Pediatr. Oct. 2008;29(5):345-50.
Pisula, E. Parents of children with autism: review of current research. Arch Psychiatry Psychother, 2003, 5: 51-63.
Plajner et al., Bayesian Network Models for Adaptive Testing; Proceedings of the Twelfth Bayesian Modeling Applications Workshop, co-located with the 31st Conference on Uncertainty in Artificial Intelligence; Amsterdam, the Netherlands, Jul. 16, 2015; http://ceur-ws.org/Vol-1565/ (Year: 2015).
Planjner, Slide presentation on Bayesian Network Models for Adaptive Testing: Proceeding of the Twelfth Bayesian Modeling Applications Workshop (2015).
Quinlan. C4. 5: Programming for machine learning. Morgan Kauffmann (6 pgs) (1993).
Risi, et al. Combining information from multiple sources in the diagnosis of autism spectrum disorders. Journal of the American Academy of Child & Adolescent Psychiatry, 2006, 45(9): 1094-1103.
Robins, et al. The Modified Checklist for Autism in Toddlers: an initial study investigating the early detection of autism and pervasive developmental disorders. J Autism Dev Disord. Apr. 2001;31(2):131-44.
Rutter et al. Autism diagnostic interview-revised. Los Angeles, CA: Western Psychological Services 29:30 (2003).
Santosh et al. The construction and validation of a short form of the developmental, diagnostic and dimensional interview. Eur Child Adolesc Psychiatry. Aug. 2009;18(8):521-4.
Shattuck, et al. Timing of identification among children with an autism spectrum disorder: findings from a population-based surveillance study. J Am Acad Child Adolesc Psychiatry. May 2009;48(5):474-83.
Shi. Best-first decision tree learning. Master Thesis, The University of Waikato (120 pgs) (2007).
Skuse et al. The developmental, dimensional and diagnostic interview (3di): a novel computerized assessment for autism spectrum disorders. Journal of the American Academy of Child & Adolescent Psychiatry 43.5:548-558 (2004).
Tadevosyan-Leyfer, et al. A principal components analysis of the Autism Diagnostic Interview-Revised. J Am Acad Child Adolesc Psychiatry. Jul. 2003;42(7):864-72.
U.S. Appl. No. 16/155,794 Office Action dated Aug. 15, 2019.
U.S. Appl. No. 16/155,798 Office Action dated Jul. 29, 2019.
U.S. Appl. No. 15/234,814 Non-Final Office Action dated Mar. 24, 2020.
U.S. Appl. No. 15/234,814 Office Action dated Oct. 3, 2019.
U.S. Appl. No. 16/155,758 Non-Final Office Action dated Jul. 7, 2020.
U.S. Appl. No. 16/155,761 Non-Final Office Action dated Apr. 2, 2020.
U.S. Appl. No. 16/155,761 Office Action dated Oct. 7, 2019.
U.S. Appl. No. 16/155,794 Non-Final Office Action dated Apr. 16, 2020.
U.S. Appl. No. 16/155,798 Non-Final Office Action dated Apr. 9, 2020.
U.S. Appl. No. 14/354,032 Notice of Allowance dated Apr. 13, 2016.
U.S. Appl. No. 14/354,032 Notice of Allowance dated Jun. 14, 2016.
U.S. Appl. No. 14/354,032 Office Action dated Jul. 28, 2015.
U.S. Appl. No. 15/234,814 Non-Final Office Action dated Jun. 7, 2018.
U.S. Appl. No. 15/234,814 Office Action dated Jan. 18, 2019.
U.S. Appl. No. 16/155,758 Preinterview First Office Action dated Feb. 8, 2019.
U.S. Appl. No. 16/155,761 Preinterview First Office Action dated Jan. 9, 2019.
U.S. Appl. No. 16/155,794 Office Action dated Jan. 14, 2019.
U.S. Appl. No. 16/157,787 Office Action dated Mar. 27, 2019.
Van Stralen et al. Diagnostic methods I: sensitivity, specificity, and other measures of accuracy. Kidney Int. 75(12):1257-1263 (2009).
Wall et al. Use of artificial intelligence to shorten the behavioral diagnosis of autism. PLoS One. 2012;7(8):e43855.
Wall, et al. Use of machine learning to shorten observation-based screening and diagnosis of autism. Transl Psychiatry. Apr. 10, 2012;2:e100.
Wenner, M. Gut Bacteria May Play a Role in Autism. Scientific American, pp. 1-4, Sep. 1, 2014.
Wiggins, et al. Examination of the time between first evaluation and first autism spectrum diagnosis in a population-based sample. J Dev Behav Pediatr. Apr. 2006;27(2 Suppl):579-87.
Witten et al. Data Mining: Practical Machine Learning Tools and Techniques with Java Implementations. Morgan Kaufmann, Amsterdam, Second Edition (558 pgs) (Oct. 2005).
European Application No. 18750938.5 Search Report dated Oct. 16, 2020.
Hamidpour, et al., Antipurinergic therapy with Suramin as a treatment for autism spectrum disorder, Journal of Biomedical sciences, Mar. 29, 2016; 5:pp. 17; abstract, p. 1, p. 2, p. 4, p. 5.
Mayes et al., Autism and ADHD: Overlapping and discriminating symptoms. Research in Autism Spectrum Disorders 6(1) :277-285 (2012).
Ogden, et al., Suramin as a chemosensitizer: Oral pharmacokinetics in rats, Pharmaceutical research, Nov. 2004;21:2058-2063; p. 2058.
U.S. Appl. No. 16/155,758 Final Office Action dated Jan. 12, 2021.
U.S. Appl. No. 16/010,284 Non-Final Office Action dated Feb. 4, 2021.

* cited by examiner

Your child's profile
* Required

Child's first name

Child's last name

Date of Birth mm/dd/yyyy

*Gender

| Girl | Boy |

* Has your child been diagnosed with any of the following? (check as many as apply)

| No | Yes |

* If yes, what was the diagnosis? Check all that apply

- Autism Spectrum Disorder
- Attention Deficit Disorder (ADD/ADHD)
- Sensory Processing Disorder
- Intellectual Disability
- Developmental Delay
- Language Delay
- Speech Delay

*Who gave the diagnosis?
- Doctor
- Clinical psychologist
- School psychologist
- Other Save

FIG. 18

STRENGTHS

What areas are strengths for your child? (optional)

Check all that apply

- Responsive, normal use of language
- Interacts well with other children
- Works well in groups
- Works well one-on-one
- Able to organize toys and items
- Follows instructions well
- Likes learning new things
- Potty trained or making progress
- Sleeps through the night Skip

FIG. 19

Back    CONCERNS

What concerns do you have about your child? (optional)
Check all that apply

| Delayed / odd use of language | ⊙ |
| Little interaction with other children | ⊙ |
| Problem behaviors (tantrums, oppositional) | ⊙ |
| Unable to follow commands or respond to name | ⊙ |
| Very restless, can't sit still | ⊙ |
| Odd or repetitive hand or finger mannerisms or body movements | ⊙ |
| Sleep problems | ⊙ |
| Tummy troubles (aches, constipation, diarrhea) | ⊙ |
| Odd use of toys | ⊙ |
| None | ⊙ |

[ Skip ]

PLATFORM AND SYSTEM FOR DIGITAL PERSONALIZED MEDICINE

CROSS-REFERENCE

The present application is a continuation of U.S. patent application Ser. No. 16/155,798, filed Oct. 9, 2018, which claims the benefit of International Patent Application No. PCT/US2018/017354, filed Feb. 8, 2018, which claims priority to U.S. Provisional Patent Application No. 62/457,130, filed Feb. 9, 2017, the entire contents of which are herein incorporated by reference for all purposes.

BACKGROUND

Prior methods and apparatus for digital diagnosis and treatment of patients are less than ideal in at least some respects. Although digital data can be acquired from patients in many ways, the integration of this digital data with patient treatment is less than ideal. For example, merely recording activity of a patient and suggesting an activity according to a predetermined treatment plan may not provide the best treatment for the patient.

Although digital diagnosis with machine learning has been proposed, the integration of digital diagnostics with patient treatments can be less than ideal. For example, classifiers used to diagnose patients may be less than ideally suited to most effectively align treatments with diagnoses or monitor treatments.

Prior methods and apparatus for diagnosing and treating cognitive function of people such as people with a developmental disorder can be less than ideal in at least some respects. Unfortunately, a less than ideal amount of time, energy and money can be required to obtain a diagnosis and treatment, and to determine whether a patient is at risk for decreased cognitive function such as dementia, Alzheimer's disease, or a developmental disorder. Examples of cognitive and developmental disorders less than ideally treated by the prior approaches include autism, autistic spectrum disorder, attention deficit disorder, attention deficit hyperactive disorder, and speech and learning disability, for example. Examples of mood and mental illness disorders less than ideally treated by the prior approaches include depression, anxiety, ADHD, obsessive compulsive disorder, and substance disorders such as substance abuse and eating disorders. The prior approaches to diagnosis and treatment of several neurodegenerative diseases can be less than ideal in many instances, and examples of such neurodegenerative diseases include age-related cognitive decline, cognitive impairment, Alzheimer's disease, Parkinson's disease, Huntington's disease, and amyotrophic lateral sclerosis ("ALS"), for example. The healthcare system is under increasing pressure to deliver care at lower costs, and prior methods and apparatus for clinically diagnosing or identifying a patient as at risk of a developmental disorder can result in greater expense and burden on the health care system than would be ideal. Further, at least some patients are not treated as soon as ideally would occur, such that the burden on the healthcare system is increased with the additional care required for these patients.

The identification and treatment of cognitive disorders in patients can present a daunting technical problem in terms of both accuracy and efficiency. Many prior methods for identifying and treating such disorders are often time-consuming and resource-intensive, requiring a patient to answer a large number of questions or undergo extensive observation under the administration of qualified clinicians, who may be limited in number and availability depending on the patient's geographical location. In addition, many prior methods for identifying and treating behavioral, neurological or mental health disorders have less than ideal accuracy and consistency, as patients to be evaluated using such methods often present a vast range of variation that can be difficult to capture and classify. A technical solution to such a technical problem would be desirable, wherein the technical solution can improve both the accuracy and efficiency for diagnosis and treatment. Ideally, such a technical solution would reduce the required time and resources for administering a method for identifying and treating attributes of cognitive function, such as behavioral, neurological or mental health disorders, and improve the accuracy and consistency of the identification outcomes of patients.

Furthermore, although prior lengthy tests with questions can be administered to caretakers such as parents in order to diagnose or identify a patient as at risk for a developmental disorder, such tests can be quite long and burdensome. For example, at least some of these tests have over one hundred questions, and more than one such lengthy test may be administered further increasing the burden on health care providers and caretakers. Additional data may be required such as clinical observation of the patient, and clinical visits may further increase the amount of time and burden on the healthcare system. Consequently, the time between a patient being identified as needing to be evaluated and being clinically identified as at risk or diagnosed with a developmental delay can be several months, and in some instances over a year.

Also, it would be helpful if diagnostic methods and treatments could be applied to patients to advance cognitive function for patients with advanced, normal and decreased cognitive function.

In addition, many prior methods and apparatus can be less than ideal for treating attributes of cognitive function, such as behavioral, neurological or mental health disorders. Although therapeutic agents can be delivered, these may not be delivered in sufficient amounts and can have undesirable side effects. Prior methods and apparatus that rely on fixed dosing or treatment regimens, for example, may not sustain appropriate amounts of the therapeutic agent for therapeutic benefit. Also, delivering too much therapeutic agent can result in side effects. Further, not all patients respond similarly, and some patients may take more drug than may be needed to achieve a desired therapeutic benefit, while other patients may not receive enough with a similar dosage. Accordingly, it would be beneficial to have methods and apparatus that could customize treatment to individual characteristics of a patient, such as pharmacokinetics of a patient.

Although a growing class of antipurinergic drugs (APDs) are being developed, the technical challenge in incorporating a therapeutic agent into a therapeutic treatment lies not only in determining an appropriate dosage, but also in how to maintain a level of the therapeutic agent in a subject's bloodstream to sustain its efficacy as a treatment. More specifically some APDs, such as suramin, may be used with doses that are too high in one patient, resulting in toxicity, while the same dose may be too low and have decreased efficacy in other patient. Accordingly, it would be advantageous to provide improved methods and apparatus for treating a cognitive disorder such as autism with a therapeutic agent such as suramin.

Work in relation to the present disclosure suggests that kidney function can be related to the clearance rate of a therapeutic agent and amount of therapeutic agent that can be administered. For example, patients can have differing kidney function and associated beta clearance rates, such that a therapeutic agent may be removed more quickly from one patient than another. Also, the amount of therapeutic agent that can be tolerated can be related to biomarkers of kidney function such as creatinine. The prior one dosage fits all approach to clinical studies, while effective can still be improved based on individual patient characteristics.

In light of the above, improved digital therapeutics for subjects are needed. Ideally, such digital therapeutics would provide a customized treatment plan for a subject, receive updated diagnostic data in response to the customized treatment plan to determine progress, and update the treatment plan accordingly. There is also a need for improved methods and apparatus of diagnosing, treating and identifying subjects who are at risk. Ideally such methods and apparatus would monitor subjects with fewer questions, decreased amounts of time, and provide clinically acceptable sensitivity and specificity in a clinical or nonclinical environment, which can be used to monitor and adapt treatment efficacy. Additionally, such methods and apparatus would ideally incorporate a timing and dose amount of a therapeutic agent such as suramin in a therapeutic treatment plan customized to effectively treat a subject for a cognitive function attribute or disorder such as autism. Ideally, such methods and apparatus can also be used to determine the developmental progress of a subject, and modify treatment to advance developmental progress.

SUMMARY

The digital personalized medicine systems and methods described herein provide digital diagnostics and digital therapeutics to a subject such as a patient. The digital personalized medicine system uses digital data to assess or diagnose symptoms of a subject in to provide personalized therapeutic treatment and improved diagnoses. The use of prioritized questions and answers with associated feature importance can be used to assess mental function and allow a subject to be diagnosed with fewer questions, such that diagnosis can be repeated more often and allow the dosage to be adjusted more frequently for improved therapeutic benefit with decrease side effects. Pharmacokinetics of the subject can be estimated based on demographic data and biomarkers or measured, in order to determine an improved treatment plan for the subject. Also, biomarkers can be used to determine when the patient may be at risk for experiencing undesirable side effects and the treatment plan adjusted accordingly. Machine learning classifiers can be trained on a population and may be used to determine the treatment plan for a subject who is not a member of the population.

A therapeutic treatment for the subject may comprise a customized personalized treatment plan that includes administration of a therapeutic agent to treat attributes of a cognitive function. The systems and methods disclosed herein are capable of providing improved dosing of a therapeutic agent such as suramin, both in terms of the appropriate amount and the timing of an administered dose to treat a cognitive disorder such as autism. Improved dosing of a therapeutic agent may be implemented by a therapeutic module that can output a personal therapeutic treatment plan comprising timing or an amount of a dose of the therapeutic agent. The therapeutic module can employ a therapeutic classifier such as, for example a machine learning classifier, an artificial intelligence classifier, or a statistical modeling classifier to determine the timing or amount of the dose of the therapeutic agent for the subject. Moreover, the personal therapeutic treatment plan can be based at least in part on answers to a set of questions related to cognitive function of a subject as well as answers to the set of questions related to cognitive function of members of a subject population. A therapeutic treatment plan provided by the methods and systems as described herein addresses at least some of the shortcomings of prior methods and systems by improving the amount and timing of a dose of therapeutic agent by using a classifier and by also optionally making use of answers to a set of questions related to a subject's cognitive function. A mobile device can allow a user to administer an appropriate amount at an appropriate time for a dose of a therapeutic agent. The mobile device can also be employed to maintain a level of the therapeutic agent within a target range over at least half the time between subsequent treatments of a dose. The mobile device can be configured to display a plurality of questions and receive a plurality of answers, and display the timing or the amount of the next dose to the user.

In an aspect, a digital therapeutic system to treat a subject with a personal therapeutic treatment plan may comprise a processor comprising software instructions for: 1) a diagnostic module to receive data for the subject and output diagnostic data for the subject; and 2) a therapeutic module to receive the diagnostic data for the subject and output the personal therapeutic treatment plan for the subject. The diagnostic module may comprise a diagnostic classifier selected from the group consisting of a machine learning classifier, an artificial intelligence classifier, and a statistical modeling classifier. The diagnostic classifier may be based on data for a subject population to determine the diagnostic data for the subject. The therapeutic treatment plan may comprise timing or an amount of a dose of therapeutic agent. The therapeutic module may comprise a therapeutic classifier selected from the group consisting of a machine learning classifier, an artificial intelligence classifier, and a statistical modeling classifier. The therapeutic classifier may be based on the data for the subject population to determine the timing or amount of the dose of the therapeutic agent for the subject.

The data for the subject may comprise answers to a plurality of questions related to cognitive function of the subject. The data for the subject population may comprise answers to the plurality of questions related to cognitive function of members of the subject population. The treatment plan may comprise the amount and the timing of the dose. The therapeutic module may be configured to determine the personal therapeutic treatment plan in response to the diagnostic data for the subject.

The diagnostic module can be configured to generate a diagnostic score in response to an answer to each of a plurality of questions, wherein said answer to each of the plurality of questions corresponds to a feature importance for said each answer, and wherein the diagnostic module is configured to generate a score in response to said feature importance and transmit the score to the therapeutic module and wherein the therapeutic module is configured to determine the timing or amount of the dose in response to the score.

The diagnostic module can be configured to generate a plurality of diagnostic scores at each of a plurality of separate non-overlapping times and to transmit the plurality of diagnostic scores to the therapeutic module for said each of the plurality of separate overlapping times, and wherein the therapeutic module is configured to determine the timing or the amount of the dose in response to the plurality of diagnostic scores.

The diagnostic module may be configured to receive updated subject data from the subject in response to the therapy of the subject and generate updated diagnostic data for the subject. The therapeutic module may be configured to receive the updated diagnostic data to determine an updated amount and an updated timing for administering an updated dose of a therapeutic agent and output an updated personal treatment plan for the subject in response to the diagnostic data and the updated diagnostic data. The personal therapeutic treatment plan for the subject may comprise the updated amount and updated timing of administering the updated dose of the therapeutic agent. The therapeutic agent may comprise a beta elimination half-life within a range from about 1 day to about 30 days. The therapeutic module may be configured to determine timing of a subsequent dose in response to the beta elimination half-life.

The therapeutic module may be configured to determine the timing or amount of the dose of the therapeutic agent and output the personal therapeutic treatment plan in response to measured pharmacokinetics of the subject. The measured pharmacokinetics of the subject may be selected from the group consisting of an alpha elimination half-life and a beta elimination half-life. The measured pharmacokinetics of the subject may be determined in response to administering a known amount of the therapeutic agent to the subject at a first time and determining an amount of the therapeutic agent at a second time. The therapeutic module may be configured to determine the amount or timing of a subsequent dose in response to a target therapeutic range of therapeutic agent in blood of the subject and the beta elimination half-life in order to provide the therapeutic agent within the therapeutic range to the subject. The therapeutic module may be configured to determine the timing of the subsequent dose in order to provide the therapeutic agent from the dose within the therapeutic range over at least half of a time between the dose and a subsequent dose. The therapeutic module may be configured to determine the timing or amount of the dose of the therapeutic agent and output the personal therapeutic treatment plan in response to an estimated beta clearance rate of the subject based on demographics of the subject. The measured pharmacokinetics of the subject may be selected from the group consisting of an alpha elimination half-life and a beta elimination half-life. The demographics of the subject may be selected from the group consisting of height, weight, age, and gender.

The therapeutic agent may comprise suramin and the subject may be a pediatric subject. The therapeutic agent may comprise suramin. An injected amount may be within a range from about 10 mg/kg body weight of the subject tto about 40 mg/kg body weight of the subject. The therapeutic module may be configured to target an amount of suramin in the subject's blood within a range from about 1 µM to about 100 µM.

The therapeutic module may be configured to determine the amount and the timing of administering the dose of the therapeutic agent based on detecting an amount of each of a plurality of metabolites in a biological sample obtained from the subject. Each metabolite may be in a metabolic pathway selected from the group consisting of: creatine or creatinine metabolism, purine metabolism, eicosanoid metabolism, resolvin metabolism, vitamin B3 metabolism, nicotinamide adenine dinucleotide metabolism, microbiome metabolism, fatty acid oxidation and/or synthesis, ganglioside metabolism, sphingolipid metabolism, glycolysis and/or gluconeogenesis, S-adenosyl methionine metabolism, S-adenosylhomocysteine metabolism, glutathione metabolism, phospholipid metabolism, nitric oxide metabolism, reactive oxygen species metabolism, cardiolipin metabolism, bile salt metabolism, cholesterol metabolism, cortisol metabolism, steroid metabolism, oxalate metabolism, glyoxylate metabolism, tryptophan metabolism, Krebs cycle, gamma-aminobutyric acid metabolism, glutamate metabolism, arginine metabolism, ornithine metabolism, proline metabolism, pyrimidine metabolism, vitamin B2 metabolism, thyroxine metabolism, amino-sugar metabolism, galactose metabolism, methionine metabolism, biopterin metabolism, neopterin metabolism, and molybdopterin metabolism.

Each metabolite may be a metabolite selected from the group consisting of: creatinine, xanthine, hypoxanthine, inosine, LTB4, guanosine, 1-methylnicotinamide, 11-dehydro-thromboxane B2, 4-hydroxyphenyllactic acid, L-cystine, hexanoylcarnitine, dihexosylceramide, ceramide, 2,3-diphosphoglyceric acid, phosphatidyl inositol, cysteine-glutathione disulfide, D-glucose, trihexosylceramide, bismonoacylphospholipid, malondialdehyde, phosphatidylcholine, 3,5-tetradecadiencarnitine, epoxy-5,8,11-eicosatrienoic acid, cardiolipin, 8,9-epoxyeicosatrienoic acid, myristoylcarnitine, cholic acid, octanoylcarnitine, pimelylcarnitine, dodecynoylcarnitine, L-homocysteic acid, 9-decenoylcarnitine, hydroxyisocaproic acid, propionic acid, 5-alpha-cholestanol, glyceric acid 1,3-biphosphate, 3-methylphenylacetic acid, cytidine, oxaloacetic acid, 9-hexadecenoylcarnitine, dehydroisoandrosterone 3-sulfate, 11-R-hydroxyeicosatetraenoic acid, pyridoxamine, 11,12-dihydroxyeicosatrienoic acid, sedoheptulose 7-phosphate, and 5-aminoimidazole-4-carboxamide ribonucleotide.

The system may comprise a user interface configured to display a plurality of questions and wherein the therapeutic module is configured to determine an efficacy in response to the plurality of questions. The therapeutic module may be configured to determine an efficacy in response to the plurality of questions. The therapeutic module may be configured to determine the dose in response to a creatinine measurement of the subject. The therapeutic module may be configured to adjust the amount of the dose injected or the timing of administering the dose in response to the diagnostic data and the updated diagnostic data for the subject. The therapeutic module may be configured to provide a fixed administration schedule and a fixed measurement schedule and to adjust an amount of a next dose in response to the diagnostic data and the updated diagnostic data for the subject. The therapeutic module may be configured to adjust the timing of administering the dose of the therapeutic agent in response to the diagnostic data and the updated diagnostic data and the measured pharmacokinetics of the subject. The subject may be not a member of the subject population. The therapeutic module classifier may be based on a portion of the data for the subject population.

In another aspect, a mobile device to provide a personalized treatment plan for a subject may comprise a display and a processor configured with instructions to: 1) display a plurality of questions related to a cognitive function of the subject; 2) receive input from a user comprising answers to the plurality of questions related to the subject before treatment of the subject; and 3) display a personal therapeutic treatment plan for the subject in response to the plurality of questions. The personal therapeutic treatment plan may comprise an amount and timing for administering a dose of a therapeutic agent. The processor may be configured with instructions to receive an indication that the user has been treated according to the personal therapeutic treatment plan. The processor may be configured with instructions to display a second plurality of questions related to a cognitive function of the subject after treatment of the subject. The processor may be configured with instructions to receive input from a user comprising answers to the plurality of questions related to the cognitive function of the subject subsequent to treatment of the subject with the therapeutic agent. The processor may be configured with instructions to display an updated personal therapeutic treatment plan for the subject. The treatment plan may comprise a second amount and timing of administering a second dose of the therapeutic agent in response to the received input from the user. The input from the user may comprise answers to the plurality of questions related to the cognitive function of the subject subsequent to treatment of the subject with the therapeutic agent. The processor may be configured with instructions to receive and display a next most predictive question among the plurality of questions before administration of the dose to the subject. The processor may be configured with instructions to receive and display a next most predictive question after administration of the dose to the subject.

The processor may be configured with instructions to repeatedly execute steps in response to received input from the user, after executing instructions to display an updated personal therapeutic treatment plan for the user. The treatment plan may comprise an amount and timing of administering a next dose of the therapeutic agent in response to the received input from the user. The input from the user may comprise answers to the plurality of questions after treatment of the user. The processor may be configured with instructions to display a prompt to the user indicating a next time the user should check in after the user has completed treatment. The processor may be configured with instructions to prompt the user to enter when a dose of a therapeutic agent was applied and a dose amount and to update a record indicating when the dose was applied and the dose amount. The processor may be configured with instructions to display a score result indicative of the user's response to the treatment. The processor may be configured with instructions to display a plurality of questions related to pharmacologic or non-pharmacologic intervention.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 18 shows a graphical user interface for use with a digital personalized medicine platform that prompts a user for information about their child's diagnostic state, in accordance with some embodiments;

FIG. 19 shows a graphical user interface for use with a digital personalized medicine platform that prompts a user for information about their child's strengths, in accordance with some embodiments;

FIG. 20 shows a graphical user interface for use with a digital personalized medicine platform that prompts a user for information about their concerns regarding their child, in accordance with some embodiments;

FIG. 28 shows a graphical user interface for use with a digital personalized medicine platform that provides suggestions to a user regarding activities that their child can perform to alleviate symptoms associated with their child's diagnosis, in accordance with some embodiments;

DETAILED DESCRIPTION

Figure 1A:
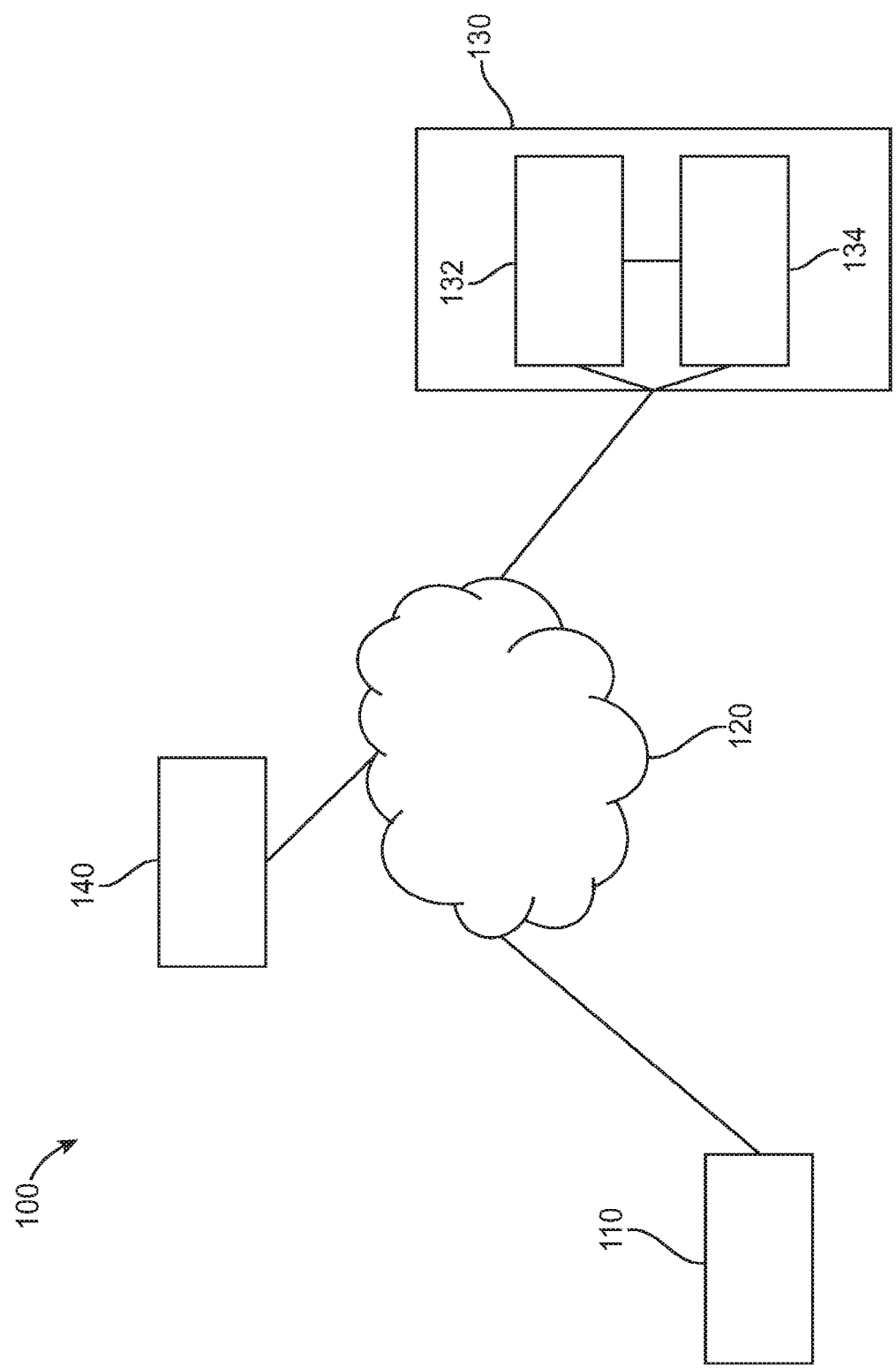
FIG. 1A illustrates an exemplary system diagram for a digital personalized medicine platform, in accordance with some embodiments.

In an aspect, the digital personalized medicine system comprises digital devices with processors and associated software configured to: receive data to assess and diagnose a subject; capture interaction and feedback data that identify relative levels of efficacy, compliance and response resulting from the therapeutic interventions; and perform data analysis, including at least one or machine learning, artificial intelligence, and statistical models to assess user data and user profiles to further personalize, improve or assess efficacy of the therapeutic interventions.

In some instances, the system is configured to use digital diagnostics and digital therapeutics. Digital diagnostics and digital therapeutics can comprise a system or methods comprising collecting digital information and processing and analyzing the provided data to improve the medical, psychological, or physiological state of an individual. A digital therapeutic system can apply software based learning to analyze user data, monitor and improve the diagnoses and therapeutic interventions provided by the system.

Digital diagnostics in the system can comprise of data and meta-data collected from the subject, or a caregiver, or a party that is independent of the individual being assessed. In some instances the collected data can comprise monitoring behaviors, observations, judgements, or assessments may be made by a party other than the individual. In further instances the assessment can comprise an adult performing an assessment or provide data for an assessment of a child or juvenile.

Data sources can comprise either active or passive sources, in digital format via one or more digital devices such as mobile phones, video capture, audio capture, activity monitors, or wearable digital monitors. Examples of active data collection comprise devices, systems or methods for tracking eye movements, recording body or appendage movement, monitoring sleep patterns, recording speech patterns. In some instances, the active sources can include audio feed data source such as speech patterns, lexical/syntactic patterns (for example, size of vocabulary, correct/incorrect use of pronouns, correct/incorrect inflection and conjugation, use of grammatical structures such as active/passive voice etc., and sentence flow), higher order linguistic patterns (for example, coherence, comprehension, conversational engagement, and curiosity), touch-screen data source (for example, fine-motor function, dexterity, precision and frequency of pointing, precision and frequency of swipe movement, and focus/attention span), and video recording of subject's face during activity (for example, quality/quantity of eye fixations vs saccades, heat map of eye focus on the screen, focus/attention span, variability of facial expression, and quality of response to emotional stimuli). Passive data collection can comprise devices, systems, or methods for collecting data from the user using recording or measurements derived from mobile applications, toys with embed sensors or recording units. In some instances, the passive source can include sensors embedded in smart toys (for example, fine motor function, gross motor function, focus/attention span and problem solving skills) and wearable devices (for example, level of activity, quantity/quality of rest).

The data used in the diagnosis and treatment can come from a plurality of sources, and may comprise a combination of passive and active data collection gathered from one device such as a mobile device with which the user interacts, or other sources such as microbiome sampling and genetic sampling of the subject.

The methods and apparatus disclose herein are well suited for the diagnosis and digital therapeutic treatment of cognitive and developmental disorders, mood and mental illness, and neurodegenerative diseases. Examples of cognitive and developmental disorders include speech and learning disorders, intelligence quotient ("IQ"), non-verbal IQ and verbal IQ and other disorders as described herein. Examples of mood and mental illness disorders, which can effect children and adults, include behavioral disorders, mood disorders, depression, attention deficit hyperactivity disorder ("ADHD"), obsessive compulsive disorder ("OCD"), schizophrenia, and substance such as eating disorders and substance abuse. Examples of neurodegenerative diseases include age related cognitive decline, cognitive impairment progressing to Alzheimer's disease and senility, Parkinson's disease and Huntington's disease, and amyotrophic lateral sclerosis ("ALS"). The methods and apparatus disclosed herein are capable of digitally diagnosing and treating children and continuing treatment until the subject becomes an adult, and can provide lifetime treatment based on personalized profiles.

The digital diagnosis and treatment as described herein is well suited for behavioral intervention coupled with biological or chemical therapeutic treatment. By gathering user interaction data as described herein, feedback effective therapies can be provided for combinations of behavioral intervention data pharmaceutical and biological treatments.

The mobile devices as describe herein may comprise sensors to collect data of the subject that can be used as part of the feedback loop so as to improve outcomes and decrease reliance on user input. The mobile device may comprise passive or active sensors as described herein to collect data of the subject subsequent to treatment. The same mobile device or a second mobile device, such as an iPad™ or iPhone™ or similar device, may comprise a software application that interacts with the user to tell the user what to do in improve treatment on a regular basis, e.g. day by day, hour by hour, etc. The user mobile device can be configured to send notifications to the user in response to treatment progress. The mobile device may comprise a drug delivery device configured to monitor deliver amounts of a therapeutic agent delivered to the subject.

The methods and apparatus disclosed herein are well suited for treatment of both parents and children, for example. Both a parent and a child can receive separate treatments as described herein. For example, neurological condition of the parent can be monitored and treated, and the developmental progress of the child monitored and treated.

The mobile device used to acquire data of the subject can be configured in many ways and may combine a plurality of devices, for example. Sleep patterns can be related to autism, for example, and sleep data acquired and used as input to the diagnostic and therapeutic modules as described herein. The mobile device may comprise a mobile wearable for sleep monitoring for a child, which can be provide as input for diagnosis and treatment and may comprise a component of the feedback loop as described herein.

Many types of sensor, biosensors and data can be used to gather data of the subject and input into the diagnosis and treatment of the subject. For example, work in relation to embodiments suggests that microbiome data can be useful for the diagnosis and treatment of autism. The microbiome data can be collected in many ways known to one of ordinary skill in the art, and may comprise data selected from a stool sample, intestinal lavage, or other sample of the flora of the subject's intestinal track. Genetic data can also be acquired an input into the diagnostic and therapeutic modules. The genetic data may comprise full genomic sequencing of the subject, of sequencing and identification of specific markers.

The diagnostic and therapeutic modules as disclosed herein can receive data from a plurality of sources, such as data acquired from the group consisting of genetic data, floral data, a sleep sensor, a wearable anklet sleep monitor, a bootie to monitor sleep, and eye tracking of the subject. The eye tracking can be performed in many ways to determine the direction and duration of gaze. The tracking can be done glasses, helmets other sensors for direction and duration of gaze. The data can be acquired with any combination of games, video games, and captured video of the subject and these can be used to determine facial expression and gaze of the subject. This data can be acquired and provided to the therapeutic module and diagnostic module as described herein before, during and after treatment, in order to initially diagnose the subject, determine treatment of the subject, modify treatment of the subject, and monitor the subject subsequent to treatment.

The visual gaze, duration of gaze and facial expression information can be acquired with methods and apparatus known to one of ordinary skill in the art, and acquired an input into the diagnostic and therapeutic modules. The data can be acquired with an app comprising software instructions, which can be downloaded. For example, facial processing has been described by Gloarai et al., "Autism and the development of face processing", Clinical Neuroscience Research 6 (2006) 145-160. An autism research group at Duke University has been conducting the Autism & Beyond research study with a software app downloaded onto mobile devices as described on the web page at autismandbeyond.researchkit.duke.edu. Data from such devices is particularly well suited for combination in accordance with the present disclosure. Facial recognition data and gaze data can be input into the diagnostic and therapeutic modules as described herein.

The classifiers as disclosed herein are particularly well suited for combination with this data to provide improved therapy and treatment. The data can be stratified and used with a feedback loop as described herein. For example, the feedback data can be used in combination with a drug therapy to determine differential responses and identify responders and non-responders. Alternatively or in combination, the feedback data can be combined with non-drug therapy, such as behavioral therapy.

With regards to genetics, recent work suggests that some people may have genetics that make them more susceptible to autism. The genetic composition of the subject may render the subject more susceptible to environmental influences, which can result symptoms and may influence the severity of symptoms. The environmental influence may comprise an insult from a toxin, virus or other substance, for example. Without being bound by any particular theory, this may result in mechanisms that change the regulation of expression genes. The change in expression of genes may be related to change in gastro-intestinal ("GI") flora, and these changes in flora may affect symptoms related to autism. Alternatively or in combination, an insult to the intestinal microbiome may result in a change in the microbiome of the subject, resulting in the subject having less than ideal homeostasis, which may affect associated symptoms related to autism. The inventors note that preliminary studies with *B. fragilis* conducted by Sarkis K. Mazmanian and others, suggest changes in this micro-organism can be related to autism and the development of autisms. (See also, "Gut Bacteria May Play a Role in Autism" by Melinda Wenner Moyer, *Scientific American,* Sep. 1, 2014)

The digital diagnostic uses the data collected by the system about the subject, which may include complimentary diagnostic data captured outside the digital diagnostic, with analysis from tools such as machine learning, artificial intelligence, and statistical modeling to assess or diagnose the subject's condition. The digital diagnostic can also provide assessment of a subject's change in state or performance, directly or indirectly via data and meta-data that can be analyzed by tools such as machine learning, artificial intelligence, and statistical modeling to provide feedback into the system to improve or refine the diagnoses and potential therapeutic interventions.

Data assessment and machine learning from the digital diagnostic and corresponding responses, or lack thereof, from the therapeutic interventions can lead to the identification of novel diagnoses for subjects and novel therapeutic regimens for both patents and caregivers.

Types of data collected and utilized by the system can include subject and caregiver video, audio, responses to questions or activities, and active or passive data streams from user interaction with activities, games or software features of the system, for example. Such data can also include meta-data from subject or caregiver interaction with the system, for example, when performing recommended activities. Specific meta-data examples include data from a user's interaction with the system's device or mobile app that captures aspects of the user's behaviors, profile, activities, interactions with the software system, interactions with games, frequency of use, session time, options or features selected, and content and activity preferences. Data may also include data and meta-data from various third party devices such as activity monitors, games or interactive content.

Digital therapeutics as described herein can comprise of instructions, feedback, activities or interactions provided to the subject or caregiver by the system. Examples include suggested behaviors, activities, games or interactive sessions with system software and/or third party devices (for example, the Internet of Things "IoT" enabled therapeutic devices as understood by one of ordinary skill in the art).

FIG. 1A illustrates a system diagram for a digital personalized medicine platform 100 for providing diagnosis and therapy related to behavioral, neurological or mental health disorders. The platform 100 can provide diagnosis and treatment of pediatric cognitive and behavioral conditions associated with developmental delays, for example. A user digital device 110—for example, a mobile device such as a smart phone, an activity monitors, or a wearable digital monitor—records data and metadata related to a subject. Data may be collected based on interactions of the subject with the device, as well as based on interactions with caregivers and health care professionals. The data may be collected actively, such as by administering tests, recording speech and/or video, and recording responses to diagnostic questions. The data may also be collected passively, such as by monitoring online behavior of subjects and caregivers, such as recording questions asked and topics investigated relating to a diagnosed developmental disorder.

The digital device 110 is connected to a computer network 120, allowing it to share data with and receive data from connected computers. In particular, the device can communicate with personalized medical system 130, which may comprise a server configured to communicate with digital device 110 over the computer network 120. Personalized medical system 130 may comprise a diagnosis module 132 to provide initial and incremental diagnosis of a subject's developmental status, as well as a therapeutic module 134 to provide personalized therapy recommendations in response to the diagnoses of diagnosis module 132.

Each of diagnosis modules 132 and 134 communicate with the user digital device 110 during a course of treatment. The diagnosis module provides diagnostic tests to and receives diagnostic feedback from the digital device 110, and uses the feedback to determine a diagnosis of a subject. An initial diagnosis may be based on a comprehensive set of tests and questions, for example, while incremental updates may be made to a diagnosis using smaller data samples. For example, the diagnostic module may diagnose autism-related speech delay based on questions asked to the caregiver and tests administered to the subject such as vocabulary or verbal communication tests. The diagnosis may indicate a number of months or years delay in speech abilities. Later tests may be administered and questions asked to update this diagnosis, for example showing a smaller or larger degree of delay.

The diagnosis module communicates its diagnosis to the digital device 110, as well as to therapeutic module 134, which uses the diagnosis to suggest therapies to be performed to treat any diagnosed symptoms. The therapeutic module 134 sends its recommended therapies to the digital device 110, including instructions for the subject and caregivers to perform the therapies recommended over a given time frame. After performing the therapies over the given time frame, the caregivers or subject can indicate completion of the recommended therapies, and a report can be sent from the digital device 110 to the therapeutic module 134. The therapeutic module 134 can then indicate to the diagnosis module 132 that the latest round of therapy is finished, and that a new diagnosis is needed. The diagnostic module 132 can then provide new diagnostic tests and questions to the digital device 110, as well as take input from the therapeutic module of any data provided as part of therapy, such as recordings of learning sessions or browsing history of caregivers or subjects related to the therapy or diagnosed condition. The diagnostic module 132 then provides an updated diagnosis to repeat the process and provide a next step of therapy.

Information related to diagnosis and therapy can also be provided from personalized medical system 130 to a third-party system 140, such as a computer system of a health care professional. The health care professional or other third party can be alerted to significant deviations from a therapy schedule, including whether a subject is falling behind an expected schedule or is improving faster than predicted. Appropriate further action can then be taken by the third party based on this provided information.

Figure 1B:
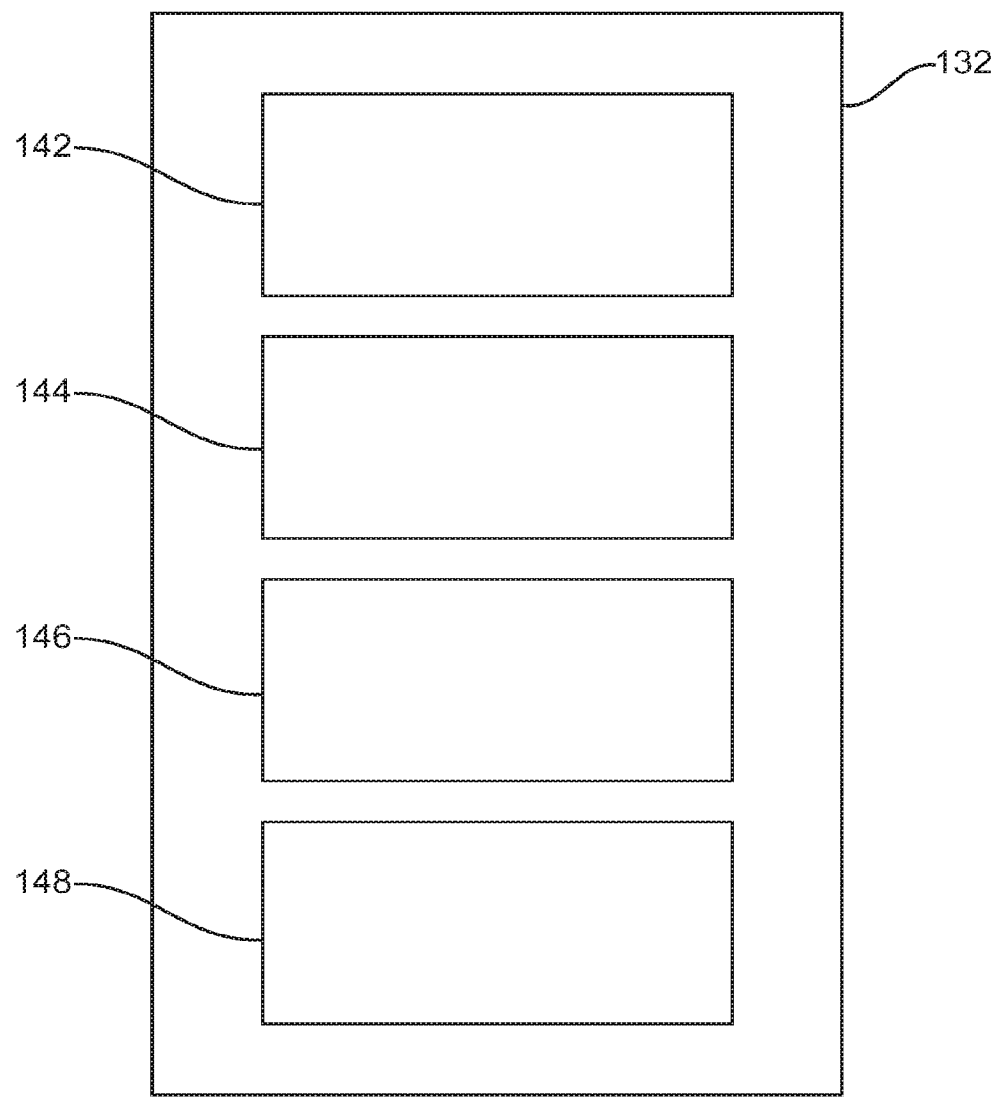
FIG. 1B illustrates a detailed diagram of an exemplary diagnosis module, in accordance with some embodiments.

FIG. 1B illustrates a detailed diagram of diagnosis module 132. The diagnosis module 132 may comprise a test administration module 142 that generates tests and corresponding instructions for administration to a subject. The diagnosis module 132 may also comprise a subject data receiving module 144 in which subject data are received, such as test results; caregiver feedback; meta-data from subject and caregiver interactions with the system; and video, audio, and gaming interactions with the system, for example. A subject assessment module 146 generates a diagnosis of the subject based on the data from subject data receiving module 144, as well as past diagnoses of the subject and of similar subjects. A machine learning module 148 assesses the relative sensitivity of each input to the diagnosis to determine which types of measurement provide the most information regarding a subject's diagnosis. These results can be used by test administration module 142 to provide tests which most efficiently inform diagnoses and by subject assessment module 146 to apply weights to diagnosis data in order to improve diagnostic accuracy and consistency. Diagnostic data relating to each treated subject are stored, for example in a database, to form a library of diagnostic data for pattern matching and machine learning. A large number of subject profiles can be simultaneously stored in such a database, for example 10,000 or more.

Figure 1C:
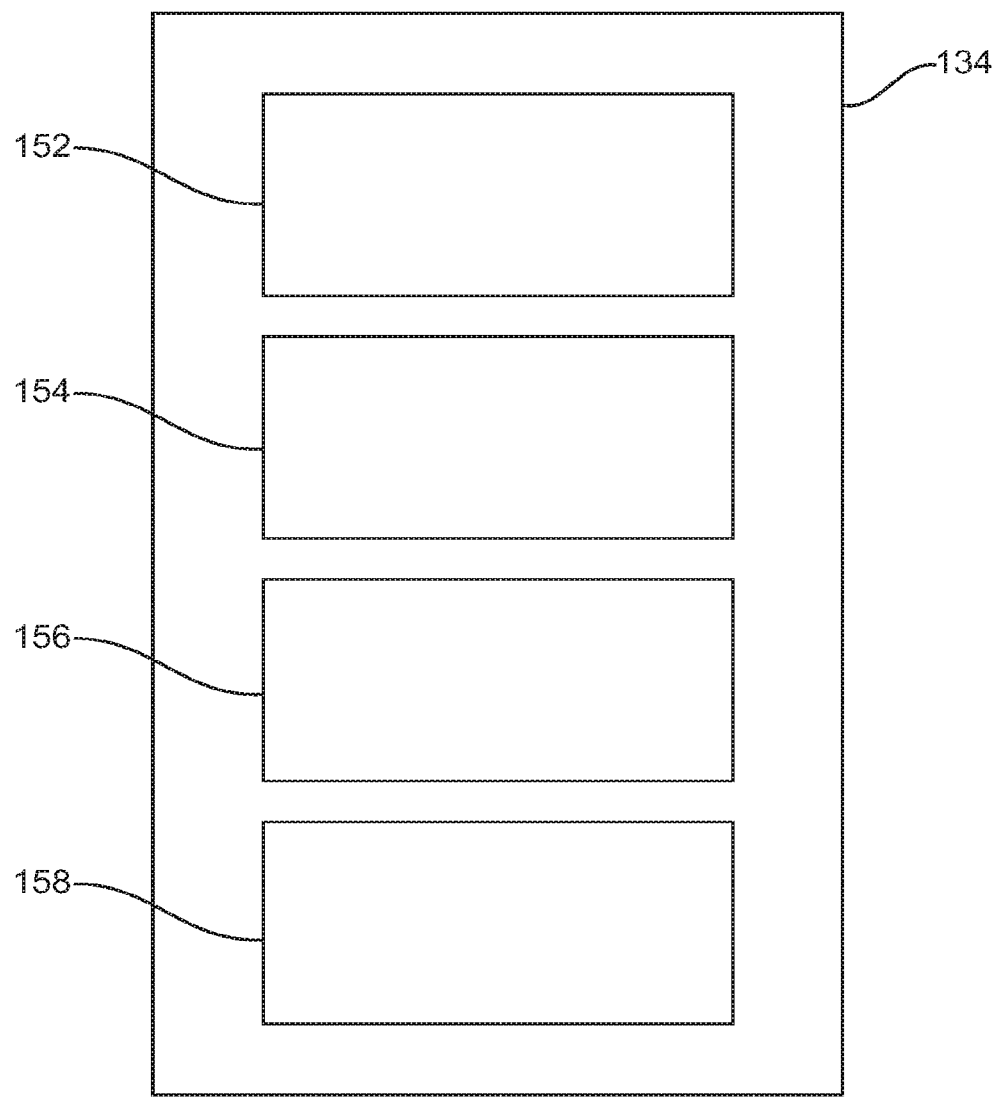
FIG. 1C illustrates a diagram of an exemplary therapeutic module, in accordance with some embodiments.

FIG. 1C illustrates a detailed diagram of therapeutic module 134. Therapeutic module 134 may comprise a therapy assessment module 152 that scores therapies based on their effectiveness. A previously suggested therapy is evaluated based on the diagnoses provided by the diagnostic module both before and after the therapy, and a degree of improvement is determined. This degree of improvement is used to score the effectiveness of the therapy. The therapy may have its effectiveness correlated with particular classes of diagnosis; for example, a therapy may be considered effective for subjects with one type of diagnosis but ineffective for subjects with a second type of diagnosis. A therapy matching module 154 is also provided that compares the diagnosis of the subject from diagnosis module 132 with a list of therapies to determine a set of therapies that have been determined by the therapy assessment module 152 to be most effective at treating diagnoses similar to the subject's diagnosis. Therapy recommendation module 156 then generates a recommended therapy comprising one or more of the therapies identified as promising by the therapy matching module 154, and sends that recommendation to the subject with instructions for administration of the recommended therapies. Therapy tracking module 158 then tracks the progress of the recommended therapies, and determines when a new diagnosis should be performed by diagnosis module 132, or when a given therapy should be continued and progress further monitored. Therapeutic data relating to each subject treated are stored, for example in a database, to form a library of therapeutic data for pattern matching and machine learning. A large number of subject profiles can be simultaneously stored in such a database, for example 10,000 or more. The therapeutic data can be correlated to the diagnostic data of the diagnostic module 132 to allow a matching of effective therapies to diagnoses.

Figure 2:
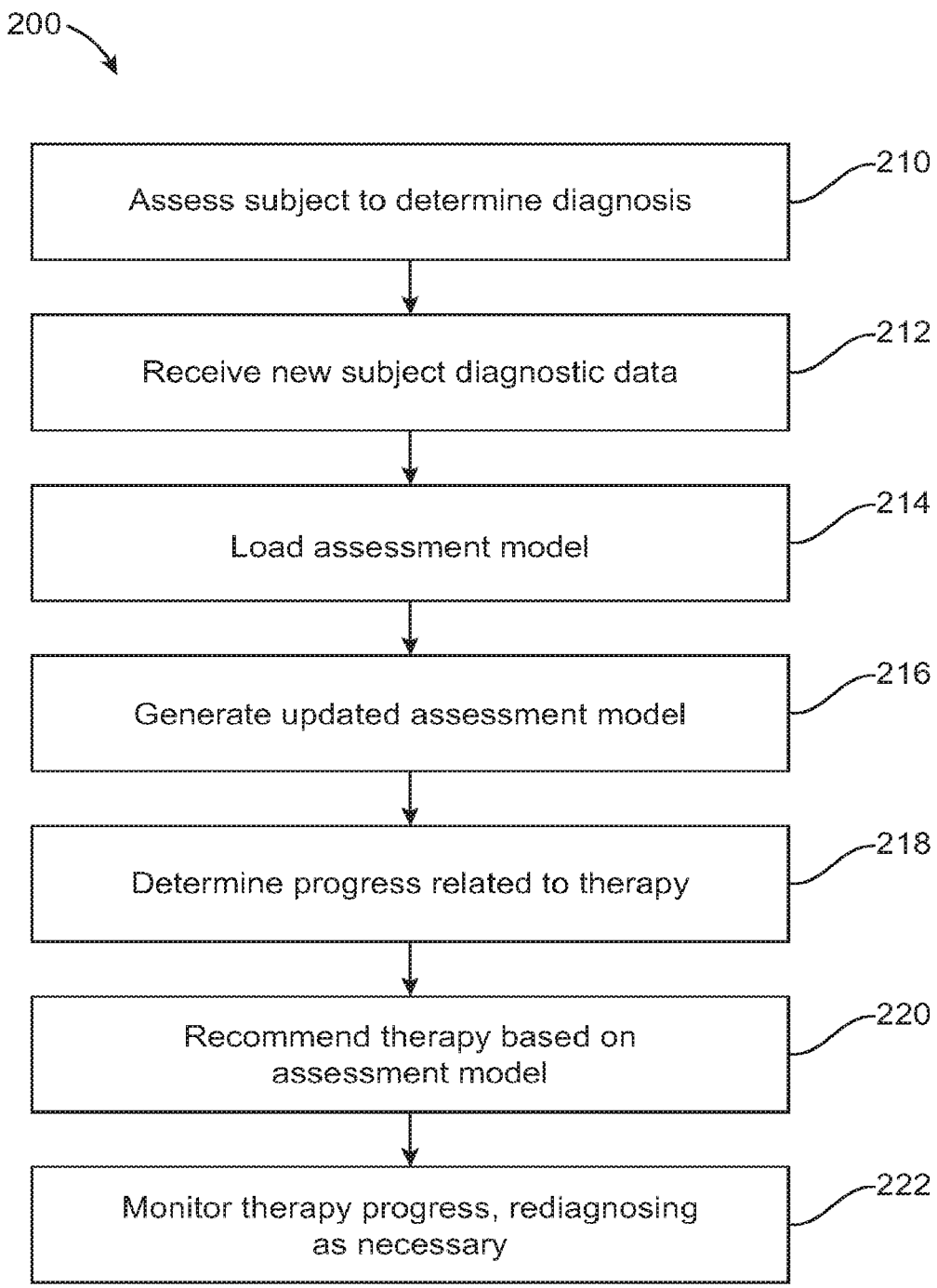
FIG. 2 illustrates an exemplary method for diagnosis and therapy to be provided in a digital personalized medicine platform, in accordance with some embodiments.

A therapy can comprise a digital therapy. A digital therapy can comprise a single or multiplicity of therapeutic activities or interventions that can be performed by the subject or caregiver. The digital therapeutic can include prescribed interactions with third party devices such as sensors, computers, medical devices and therapeutic delivery systems. Digital therapies can support an FDA approved medical claim, a set of diagnostic codes, a single diagnostic code FIG. 2 illustrates a method 200 for diagnosis and therapy to be provided in a digital personalized medicine platform. The digital personalized medicine platform communicates with a subject, which may include a subject with one or more caregivers, to provide diagnoses and recommend therapies.

In step 210 the diagnosis module assesses the subject to determine a diagnosis, for example by applying diagnostic tests to the subject. The diagnostic tests may be directed at determining a plurality of features and corresponding feature values for the subject. For example, the tests may include a plurality of questions presented to a subject, observations of the subject, or tasks assigned to the subject. The tests may also include indirect tests of the subject, such as feedback from a caregiver of subject performance versus specific behaviors and/or milestones; meta-data from subject and caregiver interactions with the system; and video, audio, and gaming interactions with the system or with third party tools that provide data on subject and caregiver behavior and performance. For initial tests, a more comprehensive testing regimen may be performed, aimed at generating an accurate initial diagnosis. Later testing used to update prior diagnoses to track progress can involve less comprehensive testing and may, for example, rely more on indirect tests such as behavioral tracking and therapy-related recordings and meta-data.

In step 212, the diagnosis module receives new data from the subject. The new data can comprise an array of features and corresponding feature values for a particular subject. As described herein, the features may comprise a plurality of questions presented to a subject, observations of the subject, or tasks assigned to the subject. The feature values may comprise input data from the subject corresponding to characteristics of the subject, such as answers of the subject to questions asked, or responses of the subject. The feature values may also comprise recorded feedback, meta-data, and system interaction data as described above.

In step 214, the diagnosis module can load a previously saved assessment model from a local memory and/or a remote server configured to store the model. Alternatively, if no assessment model exists for the subject, a default model may be loaded, for example, based on one or more initial diagnostic indications.

In step 216, the new data is fitted to the assessment model to generate an updated assessment model. This assessment model may comprise an initial diagnosis for a previously untreated subject, or an updated diagnosis for a previously treated subject. The updated diagnosis can include a measurement of progress in one or more aspects of a condition, such as memory, attention and joint attention, cognition, behavioral response, emotional response, language use, language skill, frequency of specific behaviors, sleep, socialization, non-verbal communication, and developmental milestones. The analysis of the data to determine progress and current diagnosis can include automated analysis such as question scoring and voice-recognition for vocabulary and speech analysis. The analysis can also include human scoring by analysis reviewing video, audio, and text data.

In step 218, the updated assessment model is provided to the therapeutic module, which determines what progress has been made as a result of any previously recommended therapy. The therapeutic module scores the therapy based on the amount of progress in the assessment model, with larger progress corresponding to a higher score, making a successful therapy and similar therapies more likely to be recommended to subjects with similar assessments in the future. The set of therapies available is thus updated to reflect a new assessment of effectiveness, as correlated with the subject's diagnosis.

In step 220, a new therapy is recommended based on the assessment model, the degree of success of the previous therapy, if any, and the scores assigned to a collection of candidate therapies based on previous uses of those therapies with the subject and other subjects with similar assessments. The recommended therapy is sent to the subject for administration, along with instructions of a particular span of time to apply it. For example, a therapy might include a language drill to be performed with the subject daily for one week, with each drill to be recorded in an audio file in a mobile device used by a caregiver or the subject.

In step 222, progress of the new therapy is monitored to determine whether to extend a period of therapy. This monitoring may include periodic re-diagnoses, which may be performed by returning to step 210. Alternatively, basic milestones may be recorded without a full re-diagnosis, and progress may be compared to a predicted progress schedule generated by the therapeutic module. For example, if a therapy is unsuccessful initially, the therapeutic module may suggest repeating it one or more times before either re-diagnosing and suggesting a new therapy or suggesting intervention by medical professionals.

Figure 3:
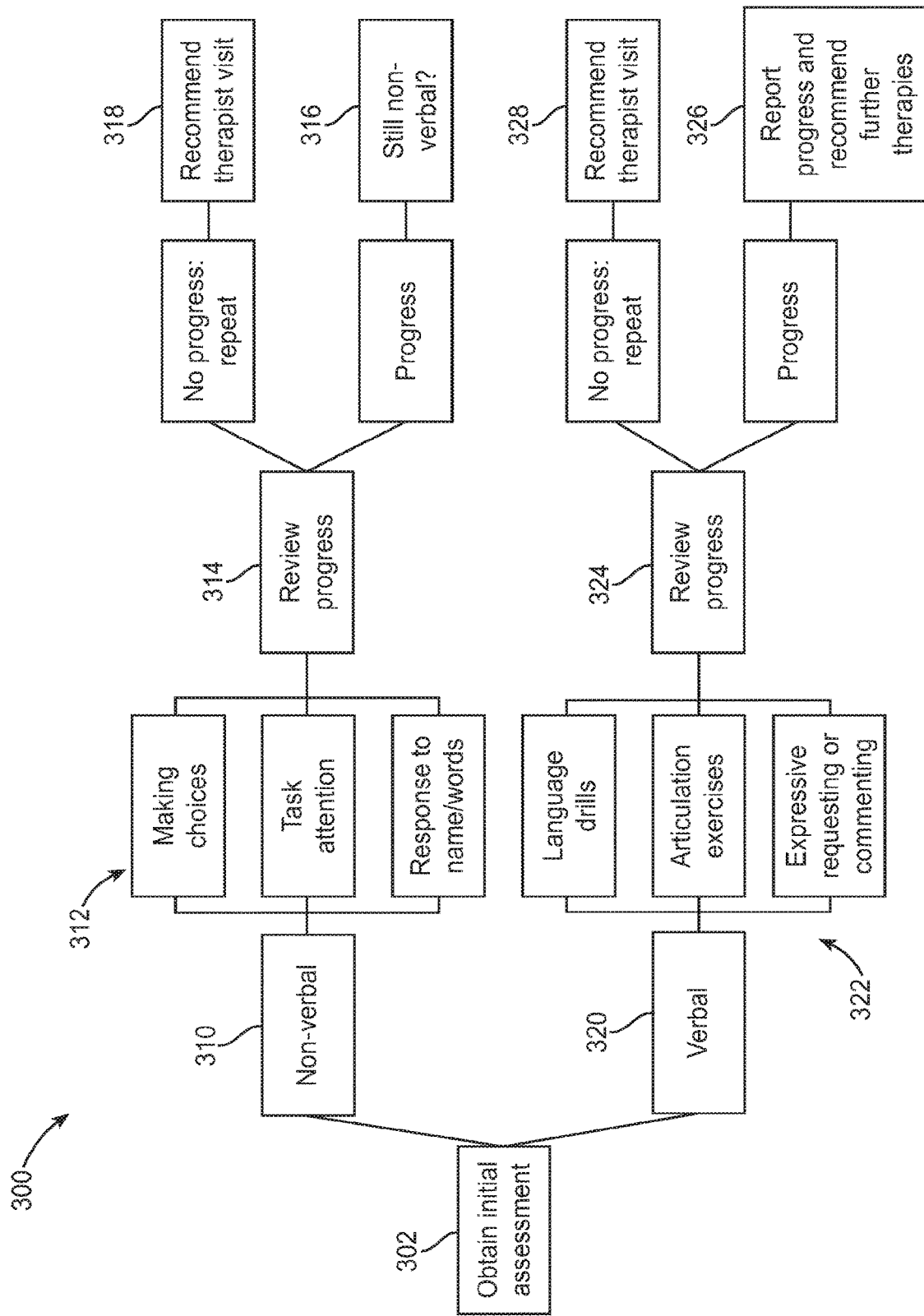
FIG. 3 illustrates an exemplary flow diagram showing the handling of autism-related developmental delay, in accordance with some embodiments.

FIG. 3 illustrates a flow diagram 300 showing the handling of suspected or confirmed speech and language delay.

In step 302 an initial assessment is determined by diagnosis module 132 (as described with respected to FIG. 1A; not shown in FIG. 3). The initial assessment can assess the subject's performance in one or more domains, such as speech and language use, and assess a degree and type of developmental delay along a number of axes, as disclosed herein. The assessment can further place the subject into one of a plurality of overall tracks of progress; for example, the subject can be assessed as verbal or nonverbal.

If the subject is determined to be non-verbal, as in step 310, one or more non-verbal therapies 312 can be recommended by the therapeutic module 134 (as described with respect to FIG. 1A; not shown in FIG. 3), such as tasks related to making choices, paying attention to tasks, or responding to a name or other words. Further suggestions of useful devices and products that may be helpful for progress may also be provided, and all suggestions can be tailored to the subject's needs as indicated by the subject's diagnosis and progress reports.

While applying the recommended therapies, progress is monitored in step 314 to determine whether a diagnosis has improved at a predicted rate.

If improvement has been measured in step 314, the system determines whether the subject is still non-verbal in step 316; if so, then the system returns to step 310 and generates a new recommended therapy 312 to induce further improvements.

If no improvement is measured in step 314, the system can recommend that the therapy be repeated a predetermined number of times. The system may also recommend trying variations in therapy to try and get better results. If such repetitions and variations fail, the system can recommend a therapist visit in step 318 to more directly address the problems impeding development.

Once the subject is determined to be verbal, as indicated in step 320, verbal therapies 322 can be generated by therapeutic module 134 (as described with respect to FIG. 1A; not shown in FIG. 3). For example, verbal therapies 322 can include one or more of language drills, articulation exercises, and expressive requesting or communicating. Further suggestions of useful devices and products that may be helpful for progress may also be provided, and all suggestions can be tailored to the subject's needs as indicated by the subject's diagnosis and progress reports.

As in the non-verbal track, progress in response to verbal therapies is continually monitored in step 324 to determine whether a diagnosis has improved at a predicted rate.

If improvement has been measured in step 324, the system reports on the progress in step 326 and generates a new recommended therapy 322 to induce further improvements.

If no improvement is detected in step 324, the system can recommend that the therapy be repeated a predetermined number of times. The system may also recommend trying variations in therapy to try and get better results. If such repetitions and variations fail, the system can recommend a therapist visit in step 328 to more directly address the problems impeding development.

The steps for non-verbal and verbal therapy can be repeated indefinitely, to the degree needed to stimulate continued learning and progress in the subject, and to prevent or retard regress through loss of verbal skills and abilities. While the specific therapy plan illustrated in FIG. 3 is directed towards pediatric speech and language delay similar plans may be generated for other subjects with developmental or cognitive issues, including plans for adult subjects. For example, neurodegenerative conditions and/or age related cognitive decline may be treated with similar diagnosis and therapy schedules, using treatments selected to be appropriate to such conditions. Further conditions that may be treated in adult or pediatric subjects by the methods and systems disclosed herein include mood disorders such as depression, OCD, and schizophrenia; cognitive impairment and decline; sleep disorders; addictive behaviors; eating disorders; and behavior related weight management problems.

Figure 4:
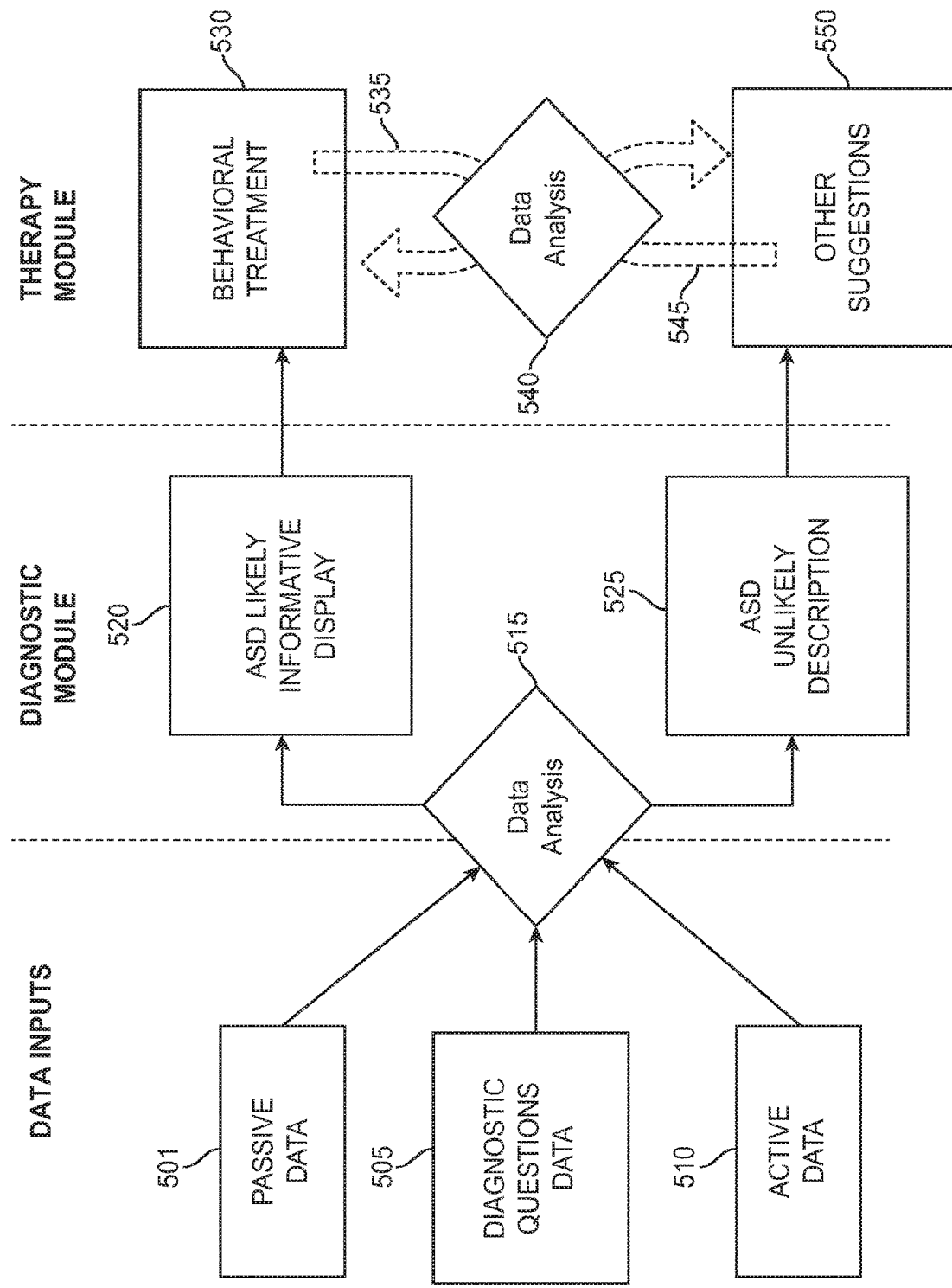
FIG. 4 illustrates an overall of data processing flows for a digital personalized medical system comprising a diagnostic module and a therapeutic module, configured to integrate information from multiple sources, in accordance with some embodiments.

FIG. 4 illustrates an overall of data processing flows for a digital personalized medical system comprising a diagnostic module and a therapeutic module, configured to integrate information from multiple sources. Data can include passive data sources (501); passive data can be configured to provide more fine-grained information, and can comprise data sets taken over longer periods of time under more nature conditions. Passive data sources can including for example, data collected from wearable devices, data collected from video feed (e.g. video feed collected from a video-enabled toy, a mobile device, eye tracking data from video footage, information on the dexterity of a subject based on information gathered from three-axis sensors or gyroscopes (e.g. sensors embedded in toys or other devices that the subject may interact with for example at home, or under normal conditions outside of a medical setting), smart devices that measure any single or combination of the following: subject's speech patterns, motions, touch response time, prosody, lexical analysis, facial expressions, and other characteristic expressed by the subject. Passive data can comprise data on the motion or motions of the user, and can include subtle information that may or may not be readily detectable to an untrained individual. In some instances, passive data can provide information that can be more encompassing.

Passively collected data can comprise data collected continuously from a variety of environments. Passively collected data can provide a more complete picture of the subject and thus can improve the quality of an assessment. In some instances, for example, passively collected data can include data collected both inside and outside of a medical setting. Passively collected data taken in a medical setting can differ from passively collected data taken from outside a medical setting. Therefore, continuously collected passive data can comprise a more complete picture of a subject's general behavior and mannerisms, and thus can include data or information that a medical practitioner would not otherwise have access to. For example, a subject undergoing evaluation in a medical setting may display symptoms, gestures, or features that are representative of the subject's response to the medical environment, and thus may not provide a complete and accurate picture of the subject's behavior outside of the medical environment under more familiar conditions. The relative importance of one or more features (e.g. features assessed by a diagnostic module) derived from an assessment in the medical environment, may differ from the relative importance of one or more features derived from or assessed outside the clinical setting.

Data can comprise information collected through diagnostic tests, diagnostic questions, or questionnaires (505). In some instances, data from diagnostic tests (505) can comprise data collected from a secondary observer (e.g. a parent, guardian, or individual that is not the subject being analyzed). Data can include active data sources (510), for example data collected from devices configured for tracking eye movement, or measuring or analyzing speech patterns.

As illustrated in FIG. 4, data inputs can be fed into a diagnostic module which can comprising data analysis (515) using for example a classifier, algorithm (e.g. machine learning algorithm), or statistical model, to make a diagnosis of whether the subject is likely to have a tested disorder (e.g. Autism Spectrum Disorder) (520) or is unlikely to have the tested disorder (525). In instances where the subject is likely to have the disorder (520), a secondary party (e.g. medical practitioner, parent, guardian or other individual) may be presented with an informative display. An informative display can provide symptoms of the disorder that can be displayed as a graph depicting covariance of symptoms displayed by the subject and symptoms displayed by the average population. A list of characteristics associated with a particular diagnosis can be displayed with confidence values, correlation coefficients, or other means for displaying the relationship between a subject's performance and the average population or a population comprised of those with a similar disorders.

If the digital personalized medicine system predicts that the user is likely to have a diagnosable condition (e.g. Autism Spectrum Disorder), then a therapeutic module can provide a behavioral treatment (530) which can comprise behavioral interventions; prescribed activities or trainings; interventions with medical devices or other therapeutics for specific durations or, at specific times or instances. As the subject undergoes the therapy, data (e.g. passive data and diagnostic question data) can continue to be collected to perform follow-up assessments, to determine whether the therapy is working, for example. Collected data can undergo data analysis (540) (e.g. analysis using machine learning, statistical modeling, classification tasks, predictive algorithms) to make determinations about the suitability of a given subject. A growth curve display can be used to show the subject's progress against a baseline (e.g. against an age-matched cohort). Performance or progress of the individual may be measured to track compliance for the subject with a suggested behavioral therapy predicted by the therapeutic module may be presented as a historic and predicted performance on a growth curve. Procedures for assessing the performance of an individual subject may be repeated or iterated (535) until an appropriate behavioral treatment is identified.

If the digital personalized medicine system predicts that the user is unlikely to have a diagnosable condition (e.g. Autism Spectrum Disorder), then a therapeutic module can provide other suggestions (550). As the subject undergoes the other suggestions, data can continue to be collected to perform follow-up assessments, to determine whether the therapy is working, for example. Collected data can undergo data analysis (540) (e.g. analysis using machine learning, statistical modeling, classification tasks, predictive algorithms) to make determinations about the progress of the other suggestions. Procedures for assessing the performance of an individual subject in response to the other suggestions may be repeated or iterated (545).

The digital therapeutics treatment methods and apparatus described with reference to FIGS. 1-4 are particularly well suited for combination with the methods and apparatus to evaluate subjects with fewer questions described herein with reference to FIGS. 5A to 14. For example the components of diagnosis module 132 as described herein can be configured to assess the subject with the decreased set of questions comprising the most relevant question as described herein, and subsequently evaluated with the therapeutic module 134 to subsequently assess the subject with subsequent set of questions comprising the most relevant questions for monitoring treatment as described herein.

Figure 5A:
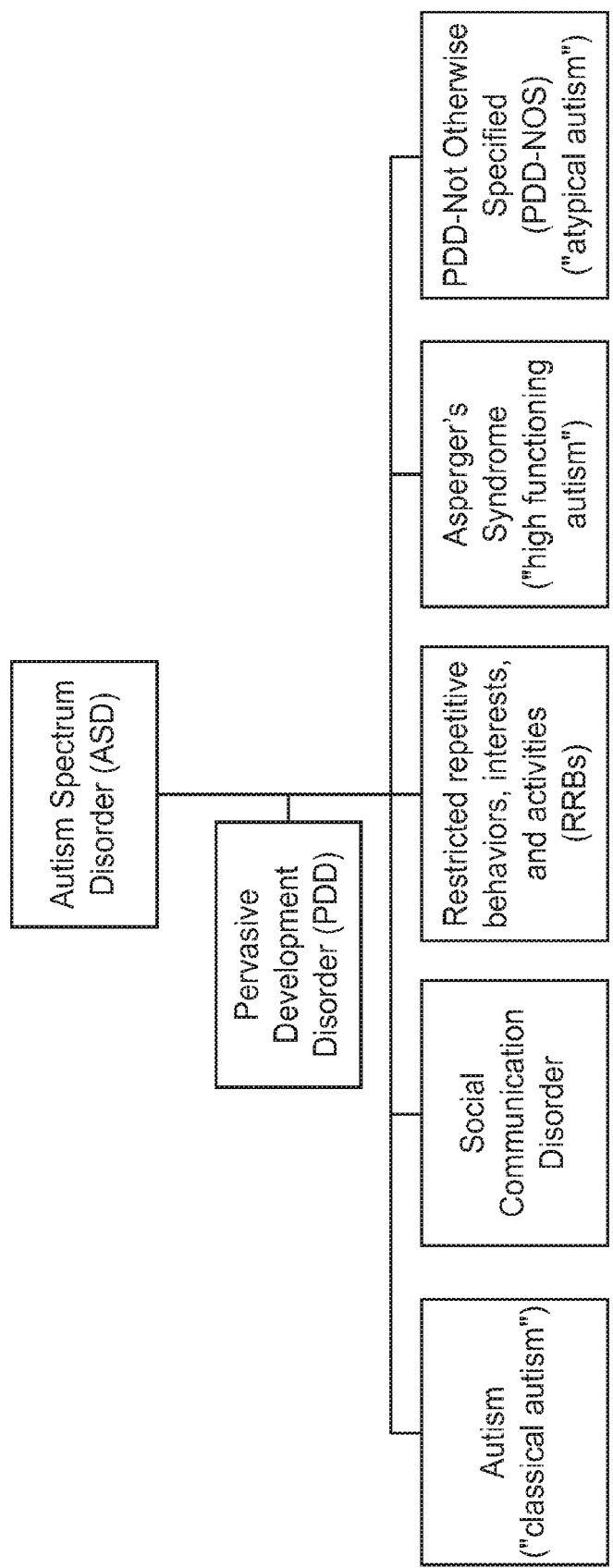
FIGS. 5A and 5B show some exemplary developmental disorders that may be diagnosed and treated using the method for diagnosis and therapy as described herein, in accordance with some embodiments.
Figure 5B:
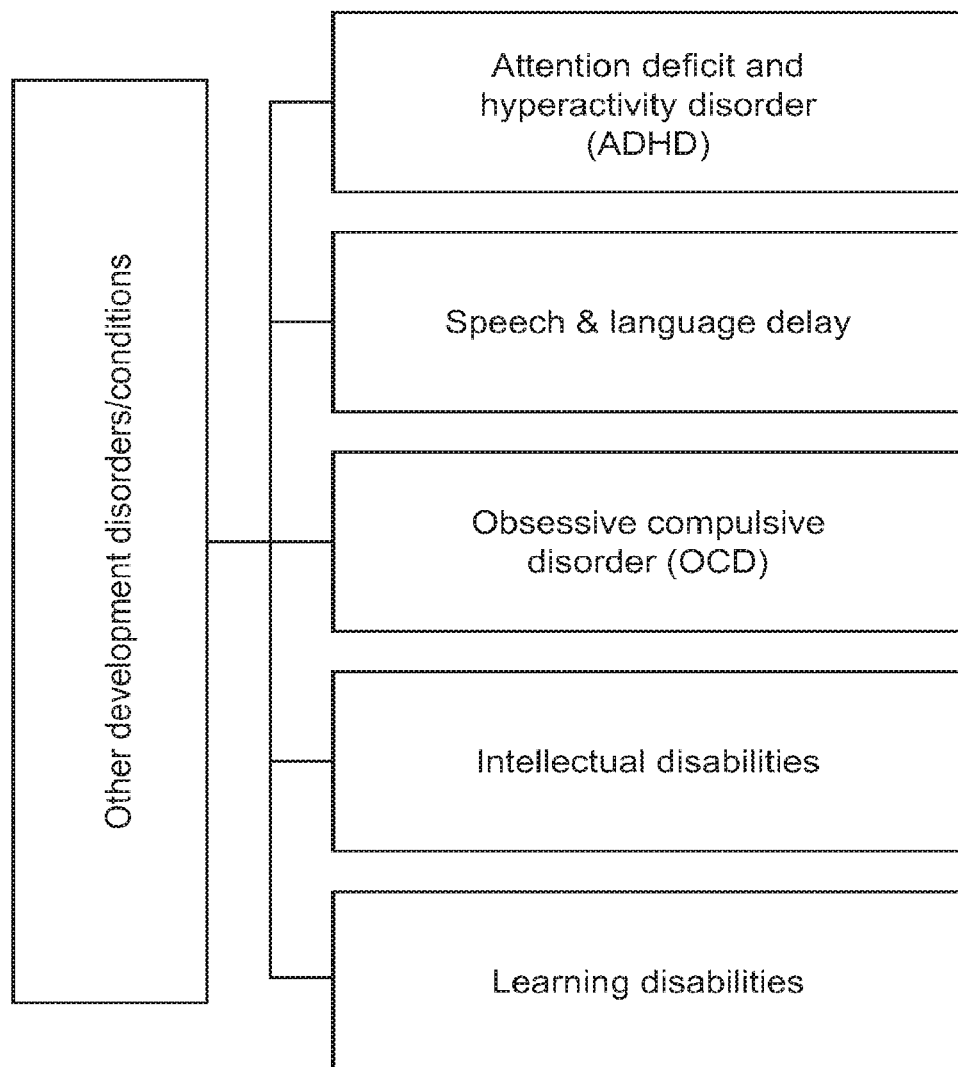

FIGS. 5A and 5B show some exemplary behavioral, neurological or mental health disorders that may be diagnosed and treated using the method for diagnosis and therapy as described herein. The diagnostic tests can be configured to evaluate a subject's risk for having one or more behavioral, neurological or mental health disorders, such as two or more related behavioral, neurological or mental health disorders. The behavioral, neurological or mental health disorders may have at least some overlap in symptoms or features of the subject. Such behavioral, neurological or mental health disorders may include pervasive development disorder (PDD), autism spectrum disorder (ASD), social communication disorder, restricted repetitive behaviors, interests, and activities (RRBs), autism ("classical autism"), Asperger's Syndrome ("high functioning autism), PDD-not otherwise specified (PDD-NOS, "atypical autism"), attention deficit and hyperactivity disorder (ADHD), speech and language delay, obsessive compulsive disorder (OCD), intellectual disability, learning disability, or any other relevant development disorder, such as disorders defined in any edition of the Diagnostic and Statistical Manual of Mental Disorders (DSM). The diagnostic tests may be configured to determine the risk of the subject for having each of a plurality of disorders. The diagnostic tests may be configured to determine the subject as at greater risk of a first disorder or a second disorder of the plurality of disorders. The diagnostic tests may be configured to determine the subject as at risk of a first disorder and a second disorder with comorbidity. The diagnostic tests may be configured to predict a subject to have normal development, or have low risk of having any of the disorders the procedure is configured to screen for. The diagnostic tests may further be configured to have high sensitivity and specificity to distinguish among different severity ratings for a disorder; for example, the procedure may be configured to predict a subject's risk for having level 1 ASD, level 2 ASD, or level 3 ASD as defined in the fifth edition of the DSM (DSM-V).

Many behavioral, neurological or mental health disorders may have similar or overlapping symptoms, thus complicating the assessment of a subject's developmental disorder. The diagnostic tests described herein can be configured to evaluate a plurality of features of the subject that may be relevant to one or more behavioral, neurological or mental health disorders. The procedure can comprise an assessment model that has been trained using a large set of clinically validated data to learn the statistical relationship between a feature of a subject and clinical diagnosis of one or more behavioral, neurological or mental health disorders. Thus, as a subject participates in the diagnostic tests, the subject's feature value for each evaluated feature (e.g., subject's answer to a question) can be queried against the assessment model to identify the statistical correlation, if any, of the subject's feature value to one or more screened behavioral, neurological or mental health disorders. Based on the feature values provided by the subject, and the relationship between those values and the predicted risk for one or more behavioral, neurological or mental health disorders as determined by the assessment model, the diagnostic tests can dynamically adjust the selection of next features to be evaluated in the subject. The selection of the next feature to be evaluated may comprise an identification of the next most predictive feature, based on the determination of the subject as at risk for a particular disorder of the plurality of disorders being screened. For example, if after the subject has answered the first five questions of the diagnostic tests, the assessment model predicts a low risk of autism and a relatively higher risk of ADHD in the subject, the diagnostic tests may select features with higher relevance to ADHD to be evaluated next in the subject (e.g., questions whose answers are highly correlated with a clinical diagnosis of ADHD may be presented next to the subject). Thus, the diagnostic tests described herein can be dynamically tailored to a particular subject's risk profile, and enable the evaluation of the subject's disorder with a high level of granularity.

Figure 6:
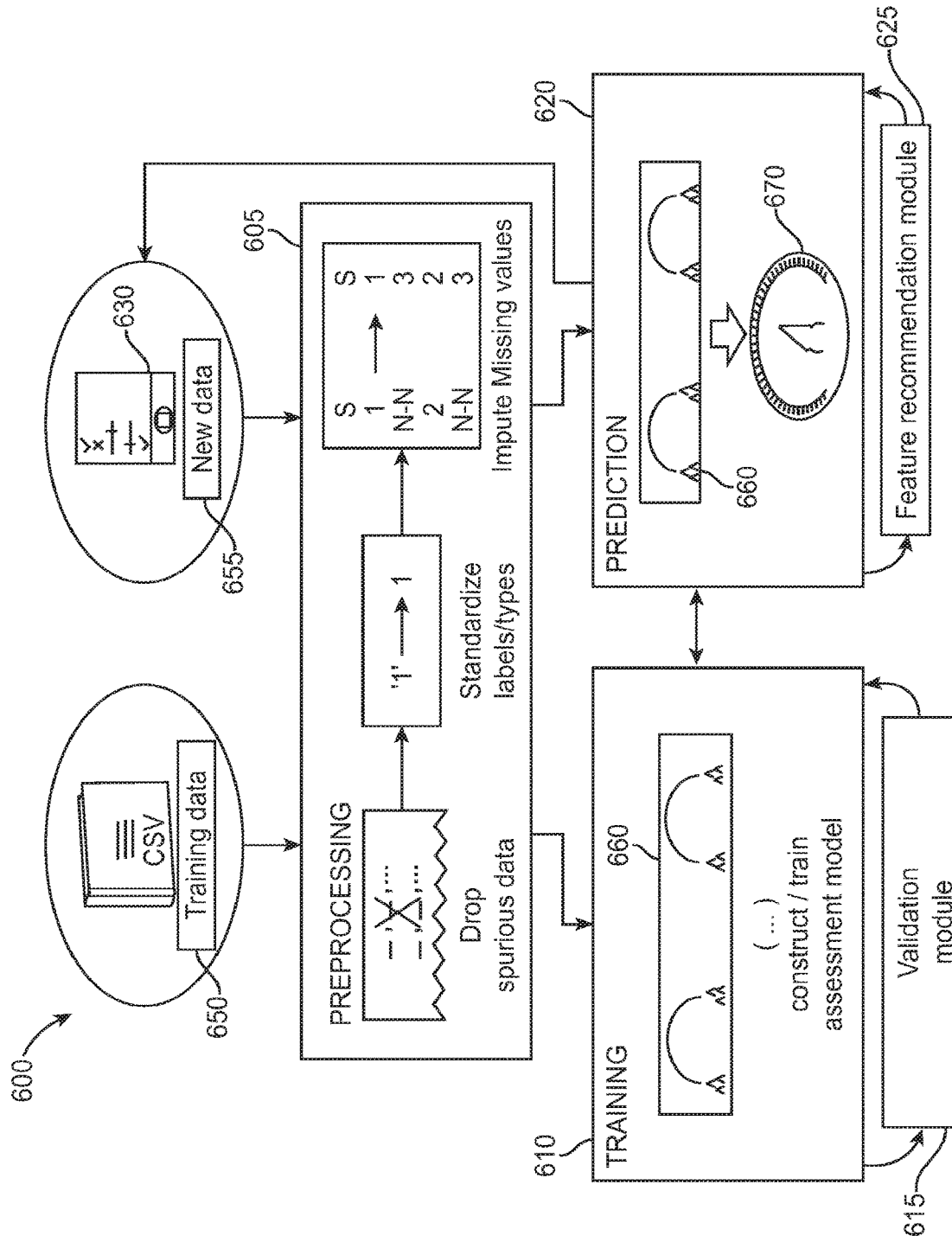
FIG. 6 is a schematic diagram of an exemplary data processing module for providing the diagnostic tests as described herein, in accordance with some embodiments.

FIG. 6 is a schematic diagram of an exemplary data processing module 600 for providing an assessment procedure for screening a subject for cognitive function as described herein, which may comprise one or more of a plurality of behavioral, neurological or mental health disorders or conditions. The assessment procedure can evaluate a plurality of features or characteristics of the subject related to cognitive function, wherein each feature can be related to the likelihood of the subject having at least one of the plurality of behavioral, neurological or mental health disorders screenable by the procedure, for example. The assessment procedure can be administered to a subject or a caretaker of the subject with a user interface provided by a computing device. In some examples, the assessment procedure may take less than 60 minutes, 45 minutes, 30 minutes, 20 minutes, 10 minutes or less to administer to the subject. In some examples, the data processing module 600 can be at least a part of the diagnosis module as described herein. The data processing module 600 may generally comprise a preprocessing module 605, a training module 610, and a prediction module 620. The data processing module can extract training data 650 from a database, or intake new data 655 with a user interface 630. The preprocessing module can apply one or more transformations to standardize the training data or new data for the training module or the prediction module. The preprocessed training data can be passed to the training module, which can construct an assessment model 660 based on the training data. The training module may further comprise a validation module 615, configured to validate the trained assessment model using any appropriate validation algorithm (e.g., Stratified K-fold cross-validation). The preprocessed new data can be passed on to the prediction module, which may output a prediction 670 of the subject's developmental disorder by fitting the new data to the assessment model constructed in the training module. The prediction module may further comprise a feature recommendation module 625, configured to select or recommend the next feature to be evaluated in the subject, based on previously provided feature values for the subject.

The training data 650, used by the training module to construct the assessment model, can comprise a plurality of datasets from a plurality of subjects, each subject's dataset comprising an array of features and corresponding feature values, and a classification of the subject's developmental disorder or condition. As described herein, the features may be evaluated in the subject via one or more of questions asked to the subject, observations of the subject, or structured interactions with the subject. Feature values may comprise one or more of answers to the questions, observations of the subject such as characterizations based on video images, or responses of the subject to a structured interaction, for example. Each feature may be relevant to the identification of one or more behavioral, neurological or mental health disorders or conditions, and each corresponding feature value may indicate the degree of presence of the feature in the specific subject. For example, a feature may be the ability of the subject to engage in imaginative or pretend play, and the feature value for a particular subject may be a score of either 0, 1, 2, 3, or 8, wherein each score corresponds to the degree of presence of the feature in the subject (e.g., 0=variety of pretend play; 1=some pretend play; 2=occasional pretending or highly repetitive pretend play; 3=no pretend play; 8=not applicable). The feature may be evaluated in the subject by way of a question presented to the subject or a caretaker such as a parent, wherein the answer to the question may comprise the feature value. Alternatively or in combination, the feature may be observed in the subject, for example with a video of the subject engaging in a certain behavior, and the feature value may be identified through the observation. In addition to the array of features and corresponding feature values, each subject's dataset in the training data may also comprise a classification of the subject. For example, the classification may be autism, autism spectrum disorder (ASD), or non-spectrum. The classification may comprise a clinical diagnosis, assigned by qualified personnel such as licensed clinical psychologists, in order to improve the predictive accuracy of the generated assessment model. The training data may comprise datasets available from large data repositories, such as Autism Diagnostic Interview-Revised (ADI-R) data and/or Autism Diagnostic Observation Schedule (ADOS) data available from the Autism Genetic Resource Exchange (AGRE), or any datasets available from any other suitable repository of data (e.g., Boston Autism Consortium (AC), Simons Foundation, National Database for Autism Research, etc.). Alternatively or in combination, the training data may comprise large self-reported datasets, which can be crowd-sourced from users (e.g., via websites, mobile applications, etc.).

The preprocessing module 605 can be configured to apply one or more transformations to the extracted training data to clean and normalize the data, for example. The preprocessing module can be configured to discard features which contain spurious metadata or contain very few observations. The preprocessing module can be further configured to standardize the encoding of feature values. Different datasets may often have the same feature value encoded in different ways, depending on the source of the dataset. For example, '900', '900.0', '904', '904.0', '−1', '−1.0', 'None', and 'NaN' may all encode for a "missing" feature value. The preprocessing module can be configured to recognize the encoding variants for the same feature value, and standardize the datasets to have a uniform encoding for a given feature value. The preprocessing module can thus reduce irregularities in the input data for the training and prediction modules, thereby improving the robustness of the training and prediction modules.

In addition to standardizing data, the preprocessing module can also be configured to re-encode certain feature values into a different data representation. In some instances, the original data representation of the feature values in a dataset may not be ideal for the construction of an assessment model. For example, for a categorical feature wherein the corresponding feature values are encoded as integers from 1 to 9, each integer value may have a different semantic content that is independent of the other values. For example, a value of '1' and a value of '9' may both be highly correlated with a specific classification, while a value of '5' is not. The original data representation of the feature value, wherein the feature value is encoded as the integer itself, may not be able to capture the unique semantic content of each value, since the values are represented in a linear model (e.g., an answer of '5' would place the subject squarely between a '1' and a '9' when the feature is considered in isolation; however, such an interpretation would be incorrect in the aforementioned case wherein a '1' and a '9' are highly correlated with a given classification while a '5' is not). To ensure that the semantic content of each feature value is captured in the construction of the assessment model, the preprocessing module may comprise instructions to re-encode certain feature values, such as feature values corresponding to categorical features, in a "one-hot" fashion, for example. In a "one-hot" representation, a feature value may be represented as an array of bits having a value of 0 or 1, the number of bits corresponding to the number of possible values for the feature. Only the feature value for the subject may be represented as a "1", with all other values represented as a "0". For example, if a subject answered "4" to a question whose possible answers comprise integers from 1 to 9, the original data representation may be [4], and the one-hot representation may be [0 0 0 1 0 0 0 0 0]. Such a one-hot representation of feature values can allow every value to be considered independently of the other possible values, in cases where such a representation would be necessary. By thus re-encoding the training data using the most appropriate data representation for each feature, the preprocessing module can improve the accuracy of the assessment model constructed using the training data.

The preprocessing module can be further configured to impute any missing data values, such that downstream modules can correctly process the data. For example, if a training dataset provided to the training module comprises data missing an answer to one of the questions, the preprocessing module can provide the missing value, so that the dataset can be processed correctly by the training module. Similarly, if a new dataset provided to the prediction module is missing one or more feature values (e.g., the dataset being queried comprises only the answer to the first question in a series of questions to be asked), the preprocessing module can provide the missing values, so as to enable correct processing of the dataset by the prediction module. For features having categorical feature values (e.g., extent of display of a certain behavior in the subject), missing values can be provided as appropriate data representations specifically designated as such. For example, if the categorical features are encoded in a one-hot representation as described herein, the preprocessing module may encode a missing categorical feature value as an array of '0' bits. For features having continuous feature values (e.g., age of the subject), the mean of all of the possible values can be provided in place of the missing value (e.g., age of 4 years).

The training module 610 can utilize a machine learning algorithm or other algorithm to construct and train an assessment model to be used in the diagnostic tests, for example. An assessment model can be constructed to capture, based on the training data, the statistical relationship, if any, between a given feature value and a specific developmental disorder to be screened by the diagnostic tests. The assessment model may, for example, comprise the statistical correlations between a plurality of clinical characteristics and clinical diagnoses of one or more behavioral, neurological or mental health disorders. A given feature value may have a different predictive utility for classifying each of the plurality of behavioral, neurological or mental health disorders to be evaluated in the diagnostic tests. For example, in the aforementioned example of a feature comprising the ability of the subject to engage in imaginative or pretend play, the feature value of "3" or "no variety of pretend play" may have a high predictive utility for classifying autism, while the same feature value may have low predictive utility for classifying ADHD. Accordingly, for each feature value, a probability distribution may be extracted that describes the probability of the specific feature value for predicting each of the plurality of behavioral, neurological or mental health disorders to be screened by the diagnostic tests. The machine learning algorithm can be used to extract these statistical relationships from the training data and build an assessment model that can yield an accurate prediction of a developmental disorder when a dataset comprising one or more feature values is fitted to the model.

One or more machine learning algorithms may be used to construct the assessment model, such as support vector machines that deploy stepwise backwards feature selection and/or graphical models, both of which can have advantages of inferring interactions between features. For example, machine learning algorithms or other statistical algorithms may be used, such as alternating decision trees (ADTree), Decision Stumps, functional trees (FT), logistic model trees (LMT), logistic regression, Random Forests, linear classifiers, or any machine learning algorithm or statistical algorithm known in the art. One or more algorithms may be used together to generate an ensemble method, wherein the ensemble method may be optimized using a machine learning ensemble meta-algorithm such as a boosting (e.g., AdaBoost, LPBoost, TotalBoost, BrownBoost, MadaBoost, LogitBoost, etc.) to reduce bias and/or variance. Once an assessment model is derived from the training data, the model may be used as a prediction tool to assess the risk of a subject for having one or more behavioral, neurological or mental health disorders. Machine learning analyses may be performed using one or more of many programming languages and platforms known in the art, such as R, Weka, Python, and/or Matlab, for example.

A Random Forest classifier, which generally comprises a plurality of decision trees wherein the output prediction is the mode of the predicted classifications of the individual trees, can be helpful in reducing overfitting to training data. An ensemble of decision trees can be constructed using a random subset of features at each split or decision node. The Gini criterion may be employed to choose the best partition, wherein decision nodes having the lowest calculated Gini impurity index are selected. At prediction time, a "vote" can be taken over all of the decision trees, and the majority vote (or mode of the predicted classifications) can be output as the predicted classification.

Figure 7:
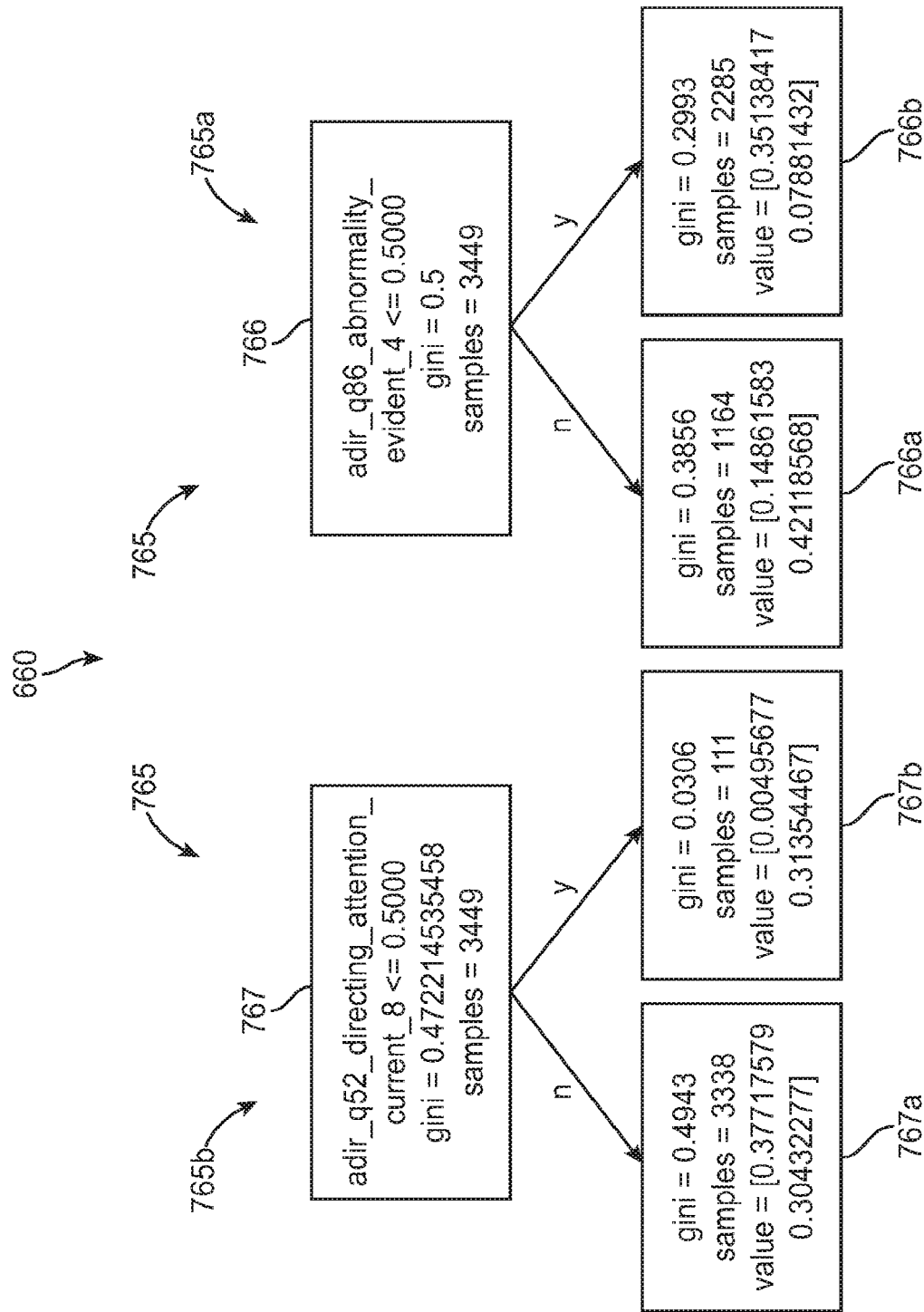
FIG. 7 is a schematic diagram illustrating a portion of an exemplary assessment model based on a Random Forest classifier, in accordance with some embodiments.

FIG. 7 is a schematic diagram illustrating a portion of an exemplary assessment model 660 based on a Random Forest classifier. The assessment module may comprise a plurality of individual decision trees 765, such as decision trees 765a and 765b, each of which can be generated independently using a random subset of features in the training data. Each decision tree may comprise one or more decision nodes such as decision nodes 766 and 767 shown in FIG. 7, wherein each decision node specifies a predicate condition. For example, decision node 766 predicates the condition that, for a given dataset of an individual, the answer to ADI-R question #86 (age when abnormality is first evident) is 4 or less. Decision node 767 predicates the condition that, for the given dataset, the answer to ADI-R question #52 (showing and direction attention) is 8 or less. At each decision node, a decision tree can be split based on whether the predicate condition attached to the decision node holds true, leading to prediction nodes (e.g., 766a, 766b, 767a, 767b). Each prediction node can comprise output values ('value' in FIG. 7) that represent "votes" for one or more of the classifications or conditions being evaluated by the assessment model. For example, in the prediction nodes shown in FIG. 7, the output values comprise votes for the individual being classified as having autism or being non-spectrum. A prediction node can lead to one or more additional decision nodes downstream (not shown in FIG. 7), each decision node leading to an additional split in the decision tree associated with corresponding prediction nodes having corresponding output values. The Gini impurity can be used as a criterion to find informative features based on which the splits in each decision tree may be constructed.

When the dataset being queried in the assessment model reaches a "leaf", or a final prediction node with no further downstream splits, the output values of the leaf can be output as the votes for the particular decision tree. Since the Random Forest model comprises a plurality of decision trees, the final votes across all trees in the forest can be summed to yield the final votes and the corresponding classification of the subject. While only two decision trees are shown in FIG. 7, the model can comprise any number of decision trees. A large number of decision trees can help reduce overfitting of the assessment model to the training data, by reducing the variance of each individual decision tree. For example, the assessment model can comprise at least about 10 decision trees, for example at least about 100 individual decision trees or more.

An ensemble of linear classifiers may also be suitable for the derivation of an assessment model as described herein. Each linear classifier can be individually trained with a stochastic gradient descent, without an "intercept term". The lack of an intercept term can prevent the classifier from deriving any significance from missing feature values. For example, if a subject did not answer a question such that the feature value corresponding to said question is represented as an array of '0' bits in the subject's data set, the linear classifier trained without an intercept term will not attribute any significance to the array of '0' bits. The resultant assessment model can thereby avoid establishing a correlation between the selection of features or questions that have been answered by the subject and the final classification of the subject as determined by the model. Such an algorithm can help ensure that only the subject-provided feature values or answers, rather than the features or questions, are factored into the final classification of the subject.

The training module may comprise feature selection. One or more feature selection algorithms (such as support vector machine, convolutional neural nets) may be used to select features able to differentiate between individuals with and without certain behavioral, neurological or mental health disorders. Different sets of features may be selected as relevant for the identification of different disorders. Stepwise backwards algorithms may be used along with other algorithms. The feature selection procedure may include a determination of an optimal number of features.

The training module may be configured to evaluate the performance of the derived assessment models. For example, the accuracy, sensitivity, and specificity of the model in classifying data can be evaluated. The evaluation can be used as a guideline in selecting suitable machine learning algorithms or parameters thereof. The training module can thus update and/or refine the derived assessment model to maximize the specificity (the true negative rate) over sensitivity (the true positive rate). Such optimization may be particularly helpful when class imbalance or sample bias exists in training data.

In at least some instances, available training data may be skewed towards individuals diagnosed with a specific developmental disorder. In such instances, the training data may produce an assessment model reflecting that sample bias, such that the model assumes that subjects are at risk for the specific developmental disorder unless there is a strong case to be made otherwise. An assessment model incorporating such a particular sample bias can have less than ideal performance in generating predictions of new or unclassified data, since the new data may be drawn from a subject population which may not comprise a sample bias similar to that present in the training data. To reduce sample bias in constructing an assessment model using skewed training data, sample weighting may be applied in training the assessment model. Sample weighting can comprise lending a relatively greater degree of significance to a specific set of samples during the model training process. For example, during model training, if the training data is skewed towards individuals diagnosed with autism, higher significance can be attributed to the data from individuals not diagnosed with autism (e.g., up to 50 times more significance than data from individuals diagnosed with autism). Such a sample weighting technique can substantially balance the sample bias present in the training data, thereby producing an assessment model with reduced bias and improved accuracy in classifying data in the real world. To further reduce the contribution of training data sample bias to the generation of an assessment model, a boosting technique may be implemented during the training process. Boosting comprises an iterative process, wherein after each iteration of training, the weighting of each sample data point is updated. For example, samples that are misclassified after the iteration can be updated with higher significances. The training process may then be repeated with the updated weightings for the training data.

The training module may further comprise a validation module 615 (as shown in FIG. 6) configured to validate the assessment model constructed using the training data. For example, a validation module may be configured to implement a Stratified K-fold cross validation, wherein k represents the number of partitions that the training data is split into for cross validation. For example, k can be any integer greater than 1, such as 3, 4, 5, 6, 7, 8, 9, or 10, or possibly higher depending on risk of overfitting the assessment model to the training data.

The training module may be configured to save a trained assessment model to a local memory and/or a remote server, such that the model can be retrieved for modification by the training module or for the generation of a prediction by the prediction module 620.

Figure 8:
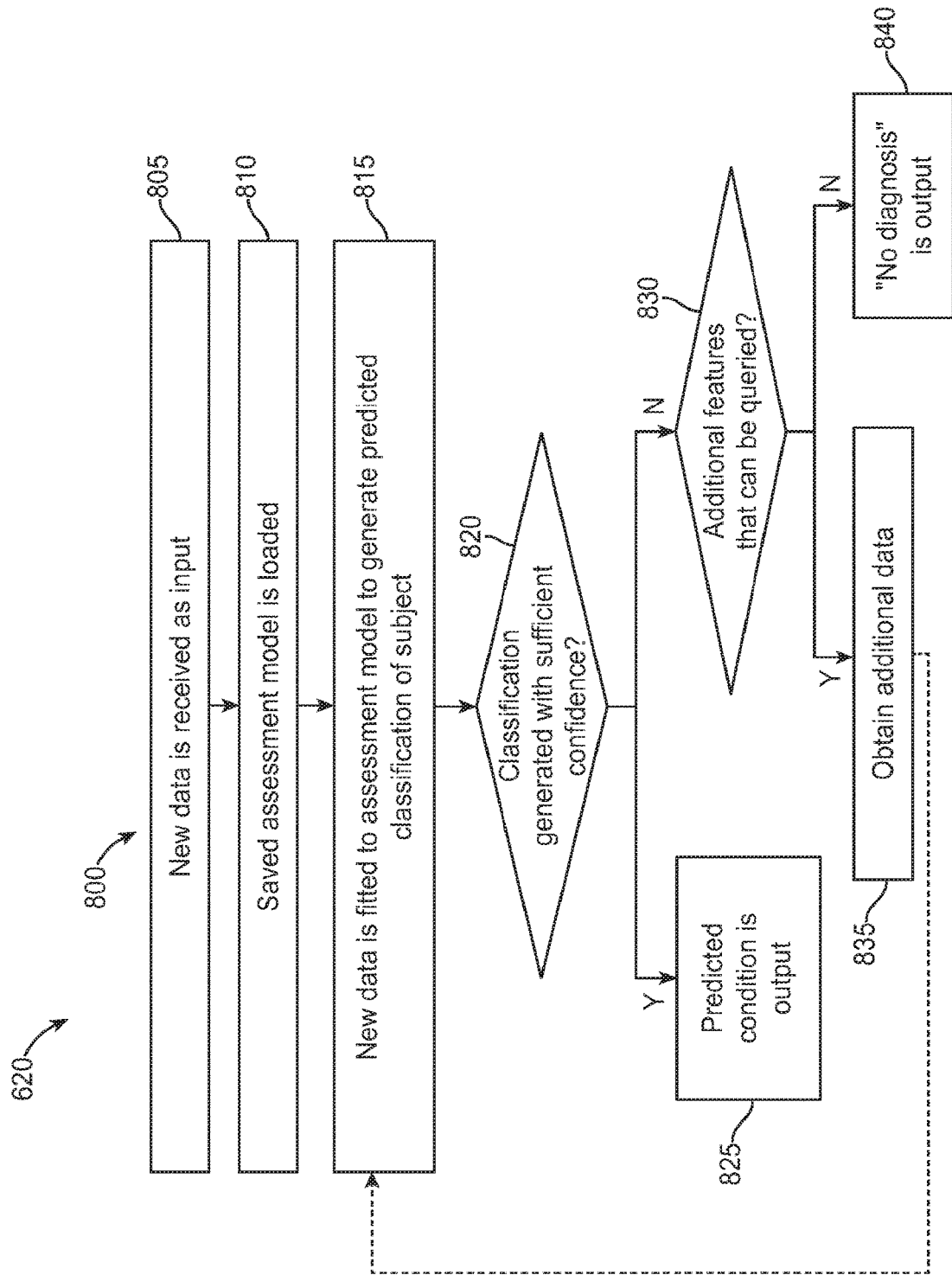
FIG. 8 is an exemplary operational flow of a prediction module as described herein, in accordance with some embodiments.

FIG. 8 is an exemplary operational flow 800 of a method of a prediction module 620 as described herein. The prediction module 620 can be configured to generate a predicted classification (e.g., developmental disorder) of a given subject, by fitting new data to an assessment model constructed in the training module. At step 805, the prediction module can receive new data that may have been processed by the preprocessing module to standardize the data, for example by dropping spurious metadata, applying uniform encoding of feature values, re-encoding select features using different data representations, and/or imputing missing data points, as described herein. The new data can comprise an array of features and corresponding feature values for a particular subject. As described herein, the features may comprise a plurality of questions presented to a subject, observations of the subject, or tasks assigned to the subject. The feature values may comprise input data from the subject corresponding to characteristics of the subject, such as answers of the subject to questions asked, or responses of the subject. The new data provided to the prediction module may or may not have a known classification or diagnosis associated with the data; either way, the prediction module may not use any pre-assigned classification information in generating the predicted classification for the subject. The new data may comprise a previously-collected, complete dataset for a subject to be diagnosed or assessed for the risk of having one or more of a plurality of behavioral, neurological or mental health disorders. Alternatively or in combination, the new data may comprise data collected in real time from the subject or a caretaker of the subject, for example with a user interface as described in further detail herein, such that the complete dataset can be populated in real time as each new feature value provided by the subject is sequentially queried against the assessment model.

At step 810, the prediction module can load a previously saved assessment model, constructed by the training module, from a local memory and/or a remote server configured to store the model. At step 815, the new data is fitted to the assessment model to generate a predicted classification of the subject. At step 820, the module can check whether the fitting of the data can generate a prediction of one or more specific disorders (e.g., autism, ADHD, etc.) within a confidence interval exceeding a threshold value, for example within a 90% or higher confidence interval, for example 95% or more. If so, as shown in step 825, the prediction module can output the one or more behavioral, neurological or mental health disorders as diagnoses of the subject or as disorders for which the subject is at risk. The prediction module may output a plurality of behavioral, neurological or mental health disorders for which the subject is determined to at risk beyond the set threshold, optionally presenting the plurality of disorders in order of risk. The prediction module may output one developmental disorder for which the subject is determined to be at greatest risk. The prediction module may output two or more development disorders for which the subject is determined to risk with comorbidity. The prediction module may output determined risk for each of the one or more behavioral, neurological or mental health disorders in the assessment model. If the prediction module cannot fit the data to any specific developmental disorder within a confidence interval at or exceeding the designated threshold value, the prediction module may determine, in step 830, whether there are any additional features that can be queried. If the new data comprises a previously-collected, complete dataset, and the subject cannot be queried for any additional feature values, "no diagnosis" may be output as the predicted classification, as shown in step 840. If the new data comprises data collected in real time from the subject or caretaker during the prediction process, such that the dataset is updated with each new input data value provided to the prediction module and each updated dataset is fitted to the assessment model, the prediction module may be able to query the subject for additional feature values. If the prediction module has already obtained data for all features included in the assessment module, the prediction module may output "no diagnosis" as the predicted classification of the subject, as shown in step 840. If there are features that have not yet been presented to the subject, as shown in step 835, the prediction module may obtain additional input data values from the subject, for example by presenting additional questions to the subject. The updated dataset including the additional input data may then be fitted to the assessment model again (step 815), and the loop may continue until the prediction module can generate an output.

Figure 9:
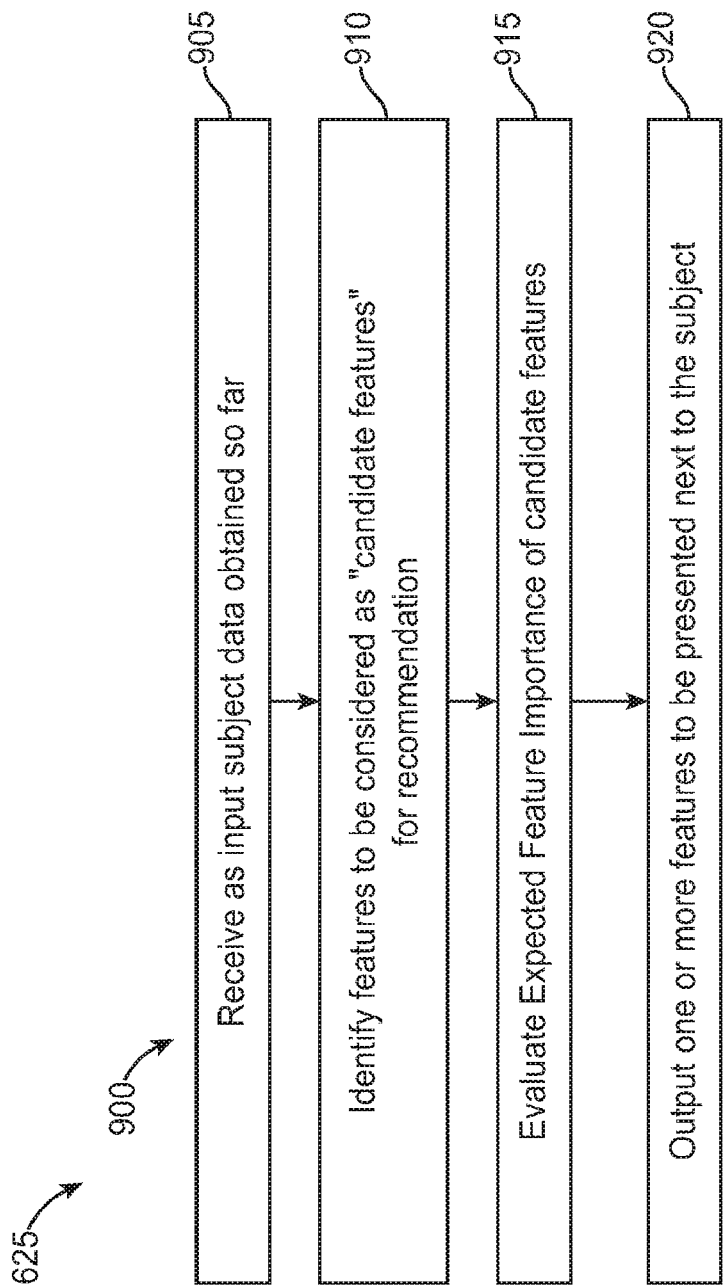
FIG. 9 is an exemplary operational flow of a feature recommendation module as described herein, in accordance with some embodiments.

FIG. 9 is an exemplary operational flow 900 of a feature recommendation module 625 as described herein by way of a non-limiting example. The prediction module may comprise a feature recommendation module 625, configured to identify, select or recommend the next most predictive or relevant feature to be evaluated in the subject, based on previously provided feature values for the subject. For example, the feature recommendation module can be a question recommendation module, wherein the module can select the most predictive next question to be presented to a subject or caretaker, based on the answers to previously presented questions. The feature recommendation module can be configured to recommend one or more next questions or features having the highest predictive utility in classifying a particular subject's developmental disorder. The feature recommendation module can thus help to dynamically tailor the assessment procedure to the subject, so as to enable the prediction module to produce a prediction with a reduced length of assessment and improved sensitivity and accuracy. Further, the feature recommendation module can help improve the specificity of the final prediction generated by the prediction module, by selecting features to be presented to the subject that are most relevant in predicting one or more specific behavioral, neurological or mental health disorders that the particular subject is most likely to have, based on feature values previously provided by the subject.

At step 905, the feature recommendation module can receive as input the data already obtained from the subject in the assessment procedure. The input subject data can comprise an array of features and corresponding feature values provided by the subject. At step 910, the feature recommendation module can select one or more features to be considered as "candidate features" for recommendation as the next feature(s) to be presented to one or more of the subject, caretaker or clinician. Features that have already been presented can be excluded from the group of candidate features to be considered. Optionally, additional features meeting certain criteria may also be excluded from the group of candidate features, as described in further detail herein.

At step 915, the feature recommendation module can evaluate the "expected feature importance" of each candidate feature. The candidate features can be evaluated for their "expected feature importance", or the estimated utility of each candidate feature in predicting a specific developmental disorder for the specific subject. The feature recommendation module may utilize an algorithm based on: (1) the importance or relevance of a specific feature value in predicting a specific developmental disorder; and (2) the probability that the subject may provide the specific feature value. For example, if the answer of "3" to ADOS question B5 is highly correlated with a classification of autism, this answer can be considered a feature value having high utility for predicting autism. If the subject at hand also has a high probability of answering "3" to said question B5, the feature recommendation module can determine this question to have high expected feature importance. An algorithm that can be used to determine the expected feature importance of a feature is described in further detail in reference to FIG. 10, for example.

At step 920, the feature recommendation module can select one or more candidate features to be presented next to the subject, based on the expected feature importance of the features as determined in step 915. For example, the expected feature importance of each candidate feature may be represented as a score or a real number, which can then be ranked in comparison to other candidate features. The candidate feature having the desired rank, for example a top 10, top 5, top 3, top 2, or the highest rank, may be selected as the feature to the presented next to the subject.

Figure 10:
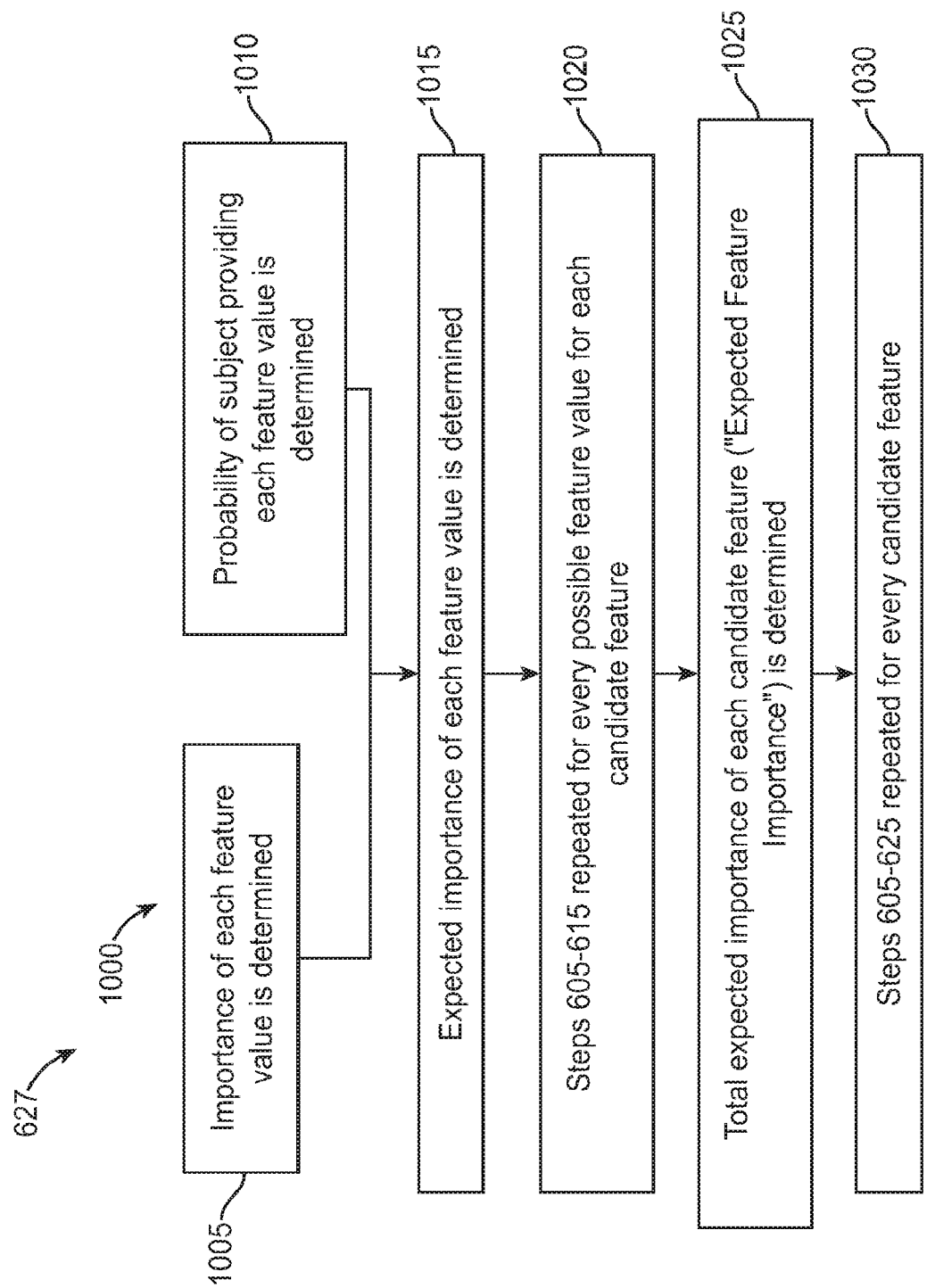
FIG. 10 is an exemplary operational flow of an expected feature importance determination algorithm as performed by a feature recommendation module described herein, in accordance with some embodiments.

FIG. 10 is an exemplary operational flow 1000 of method of determining an expected feature importance determination algorithm 627 as performed by a feature recommendation module 625 described herein.

At step 1005, the algorithm can determine the importance or relevance of a specific feature value in predicting a specific developmental disorder. The importance or relevance of a specific feature value in predicting a specific developmental disorder can be derived from the assessment model constructed using training data. Such a "feature value importance" can be conceptualized as a measure of how relevant a given feature value's role is, should it be present or not present, in determining a subject's final classification. For example, if the assessment model comprises a Random Forest classifier, the importance of a specific feature value can be a function of where that feature is positioned in the Random Forest classifier's branches. Generally, if the average position of the feature in the decision trees is relatively high, the feature can have relatively high feature importance. The importance of a feature value given a specific assessment model can be computed efficiently, either by the feature recommendation module or by the training module, wherein the training module may pass the computed statistics to the feature recommendation module. Alternatively, the importance of a specific feature value can be a function of the actual prediction confidence that would result if said feature value was provided by the subject. For each possible feature value for a given candidate feature, the feature recommendation module can be configured to calculate the actual prediction confidence for predicting one or more behavioral, neurological or mental health disorders, based on the subject's previously provided feature values and the currently assumed feature value.

Each feature value may have a different importance for each developmental disorder for which the assessment procedure is designed to screen. Accordingly, the importance of each feature value may be represented as a probability distribution that describes the probability of the feature value yielding an accurate prediction for each of the plurality of behavioral, neurological or mental health disorders being evaluated.

At step 1010, the feature recommendation module can determine the probability of a subject providing each feature value. The probability that the subject may provide a specific feature value can be computed using any appropriate statistical model. For example, a large probabilistic graphical model can be used to find the values of expressions such as:

$$\text{prob}(E=1|A=1, B=2, C=1)$$

where A, B, and C represent different features or questions in the prediction module and the integers 1 and 2 represent different possible feature values for the feature (or possible answers to the questions). The probability of a subject providing a specific feature value may then be computed using Bayes' rule, with expressions such as:

$$\text{prob}(E=1|A=1, B=2, C=1)=\text{prob}(E=1, A=1, B=2, C=1)/\text{prob}(A=1, B=2, C=1)$$

Such expressions may be computationally expensive, in terms of both computation time and required processing resources. Alternatively or in combination with computing the probabilities explicitly using Bayes' rule, logistic regression or other statistical estimators may be used, wherein the probability is estimated using parameters derived from a machine learning algorithm. For example, the following expression may be used to estimate the probability that the subject may provide a specific feature value:

$$\text{prob}(E=1|A=1, B=2, C=1) \approx \text{sigmoid}(a1*A+a2*B+a3*C+a4),$$

wherein a1, a2, a3, and a4 are constant coefficients determined from the trained assessment model, learned using an optimization algorithm that attempts to make this expression maximally correct, and wherein sigmoid is a nonlinear function that enables this expression to be turned into a probability. Such an algorithm can be quick to train, and the resulting expressions can be computed quickly in application, e.g., during administration of the assessment procedure. Although reference is made to four coefficients, as many coefficients as are helpful may be used as will be recognized by a person of ordinary skill in the art.

At step 1015, the expected importance of each feature value can be determined based on a combination of the metrics calculated in steps 1005 and 1010. Based on these two factors, the feature recommendation module can determine the expected utility of the specific feature value in predicting a specific developmental disorder. Although reference is made herein to the determination of expected importance via multiplication, the expected importance can be determined by combining coefficients and parameters in many ways, such as with look up tables, logic, or division, for example.

At step 1020, steps 1005-1015 can be repeated for every possible feature value for each candidate feature. For example, if a particular question has 4 possible answers, the expected importance of each of the 4 possible answers is determined.

At step 1025, the total expected importance, or the expected feature importance, of each candidate feature can be determined. The expected feature importance of each feature can be determined by summing the feature value importances of every possible feature value for the feature, as determined in step 1020. By thus summing the expected utilities across all possible feature values for a given feature, the feature recommendation module can determine the total expected feature importance of the feature for predicting a specific developmental disorder in response to previous answers.

At step 1030, steps 1005-1025 can be repeated for every candidate feature being considered by the feature recommendation module. The candidate features may comprise a subset of possible features such as questions. Thus, an expected feature importance score for every candidate feature can be generated, and the candidate features can be ranked in order of highest to lowest expected feature importance.

Optionally, in addition to the two factors determined in steps 1005 and 1010, a third factor may also be taken into account in determining the importance of each feature value. Based on the subject's previously provided feature values, the subject's probability of having one or more of the plurality of behavioral, neurological or mental health disorders can be determined. Such a probability can be determined based on the probability distribution stored in the assessment model, indicating the probability of the subject having each of the plurality of screened behavioral, neurological or mental health disorders based on the feature values provided by the subject. In selecting the next feature to be presented to the subject, the algorithm may be configured to give greater weight to the feature values most important or relevant to predicting the one or more behavioral, neurological or mental health disorders that the subject at hand is most likely to have. For example, if a subject's previously provided feature values indicate that the subject has a higher probability of having either an intellectual disability or speech and language delay than any of the other behavioral, neurological or mental health disorders being evaluated, the feature recommendation module can favor feature values having high importance for predicting either intellectual disability or speech and language delay, rather than features having high importance for predicting autism, ADHD, or any other developmental disorder that the assessment is designed to screen for. The feature recommendation module can thus enable the prediction module to tailor the prediction process to the subject at hand, presenting more features that are relevant to the subject's potential developmental disorder to yield a final classification with higher granularity and confidence.

Although the above steps show an exemplary operational flow 1000 of an expected feature importance determination algorithm 627, a person of ordinary skill in the art will recognize many variations based on the teachings described herein. The steps may be completed in a different order. Steps may be added or deleted. Some of the steps may comprise sub-steps of other steps. Many of the steps may be repeated as often as desired by the user.

An exemplary implementation of the feature recommendation module is now described. Subject X has provided answers (feature values) to questions (features) A, B, and C in the assessment procedure:

Subject $X=\{\text{'}A\text{'}:1, \text{'}B\text{'}:2, \text{'}C\text{'}:1\}$

The feature recommendation module can determine whether question D or question E should be presented next in order to maximally increase the predictive confidence with which a final classification or diagnosis can be reached. Given Subject X's previous answers, the feature recommendation module determines the probability of Subject X providing each possible answer to each of questions D and E, as follows:

$\text{prob}(E=1|A=1, B=2, C=1)=0.1$ $\text{prob}(E=2|A=1, B=2, C=1)=0.9$ $\text{prob}(D=1|A=1, B=2, C=1)=0.7$ $\text{prob}(D=2|A=1, B=2, C=1)=0.3$ The feature importance of each possible answer to each of questions D and E can be computed based on the assessment model as described. Alternatively, the feature importance of each possible answer to each of questions D and E can be computed as the actual prediction confidence that would result if the subject were to give the specific answer. The importance of each answer can be represented using a range of values on any appropriate numerical scale. For example:

$\text{importance}(E=1)=1$ $\text{importance}(E=2)=3$ $\text{importance}(D=1)=2$ $\text{importance}(D=2)=4$ Based on the computed probabilities and the feature value importances, the feature recommendation module can compute the expected feature importance of each question as follows:

$$\text{Expectation}[\text{importance}(E)] = \\ (prob(E=1|A=1, B=2, C=1)*\text{importance}(E=1) + \\ (prob(E=2|A=1, B=2, C=1)*\text{importance}(E=2) = \\ 0.1*1 + 0.9*3 = 2.8$$

$$\text{Expectation}[\text{importance}(D)] = (prob(D=1|A=1, B=2, C=1)* \\ \text{importance}(D=1) + (prob(D=2|A=1, B=2, C-1)* \\ \text{importance}(D=2) = 0.7*2 + 0.3*4 = 2.6$$

Hence, the expected feature importance (also referred to as relevance) from the answer of question E is determined to be higher than that of question D, even though question D has generally higher feature importances for its answers. The feature recommendation module can therefore select question E as the next question to be presented to Subject X.

When selecting the next best feature to be presented to a subject, the feature recommendation module 625 may be further configured to exclude one or more candidate features from consideration, if the candidate features have a high co-variance with a feature that has already been presented to the subject. The co-variance of different features may be determined based on the training data, and may be stored in the assessment model constructed by the training module. If a candidate feature has a high co-variance with a previously presented feature, the candidate feature may add relatively little additional predictive utility, and may hence be omitted from future presentation to the subject in order to optimize the efficiency of the assessment procedure.

The prediction module 620 may interact with the person participating in the assessment procedure (e.g., a subject or the subject's caretaker) with a user interface 630. The user interface may be provided with a user interface, such as a display of any computing device that can enable the user to access the prediction module, such as a personal computer, a tablet, or a smartphone. The computing device may comprise a processor that comprises instructions for providing the user interface, for example in the form of a mobile application. The user interface can be configured to display instructions from the prediction module to the user, and/or receive input from the user with an input method provided by the computing device. Thus, the user can participate in the assessment procedure as described herein by interacting with the prediction module with the user interface, for example by providing answers (feature values) in response to questions (features) presented by the prediction module. The user interface may be configured to administer the assessment procedure in real-time, such that the user answers one question at a time and the prediction module can select the next best question to ask based on recommendations made by the feature recommendation module. Alternatively or in combination, the user interface may be configured to receive a complete set of new data from a user, for example by allowing a user to upload a complete set of feature values corresponding to a set of features.

As described herein, the features of interest relevant to identifying one or more behavioral, neurological or mental health disorders may be evaluated in a subject in many ways. For example, the subject or caretaker or clinician may be asked a series of questions designed to assess the extent to which the features of interest are present in the subject. The answers provided can then represent the corresponding feature values of the subject. The user interface may be configured to present a series of questions to the subject (or any person participating in the assessment procedure on behalf of the subject), which may be dynamically selected from a set of candidate questions as described herein. Such a question-and-answer based assessment procedure can be administered entirely by a machine, and can hence provide a very quick prediction of the subject's developmental disorder(s).

Alternatively or in combination, features of interest in a subject may be evaluated with observation of the subject's behaviors, for example with videos of the subject. The user interface may be configured to allow a subject or the subject's caretaker to record or upload one or more videos of the subject. The video footage may be subsequently analyzed by qualified personnel to determine the subject's feature values for features of interest. Alternatively or in combination, video analysis for the determination of feature values may be performed by a machine. For example, the video analysis may comprise detecting objects (e.g., subject, subject's spatial position, face, eyes, mouth, hands, limbs, fingers, toes, feet, etc.), followed by tracking the movement of the objects. The video analysis may infer the gender of the subject, and/or the proficiency of spoken language(s) of the subject. The video analysis may identify faces globally, or specific landmarks on the face such as the nose, eyes, lips and mouth to infer facial expressions and track these expressions over time. The video analysis may detect eyes, limbs, fingers, toes, hands, feet, and track their movements over time to infer behaviors. In some cases, the analysis may further infer the intention of the behaviors, for example, a child being upset by noise or loud music, engaging in self-harming behaviors, imitating another person's actions, etc. The sounds and/or voices recorded in the video files may also be analyzed. The analysis may infer a context of the subject's behavior. The sound/voice analysis may infer a feeling of the subject. The analysis of a video of a subject, performed by a human and/or by a machine, can yield feature values for the features of interest, which can then be encoded appropriately for input into the prediction module. A prediction of the subject's developmental disorder may then be generated based on a fitting of the subject's feature values to the assessment model constructed using training data.

Alternatively or in combination, features of interest in a subject may be evaluated through structured interactions with the subject. For example, the subject may be asked to play a game such as a computer game, and the performance of the subject on the game may be used to evaluate one or more features of the subject. The subject may be presented with one or more stimuli (e.g., visual stimuli presented to the subject via a display), and the response of the subject to the stimuli may be used to evaluate the subject's features. The subject may be asked to perform a certain task (e.g., subject may be asked to pop bubbles with his or her fingers), and the response of the subject to the request or the ability of the subject to carry out the requested task may be used to evaluate to the subject's features.

The methods and apparatus described herein can be configured in many ways to determine the next most predictive or relevant question. At least a portion of the software instructions as described herein can be configured to run locally on a local device so as to provide the user interface and present questions and receive answers to the questions. The local device can be configured with software instructions of an application program interface (API) to query a remote server for the most predictive next question. The API can return an identified question based on the feature importance as described herein, for example. Alternatively or in combination, the local processor can be configured with instructions to determine the most predictive next question in response to previous answers. For example, the prediction module 620 may comprise software instructions of a remote server, or software instructions of a local processor, and combinations thereof. Alternatively or in combination, the feature recommendation module 625 may comprise software instructions of a remote server, or software instructions of a local processor, and combinations thereof, configured to determine the most predictive next question, for example. The exemplary operational flow 1000 of method of determining an expected feature importance determination algorithm 627 as performed by a feature recommendation module 625 described herein can be performed with one or more processors as described herein, for example.

Figure 11:
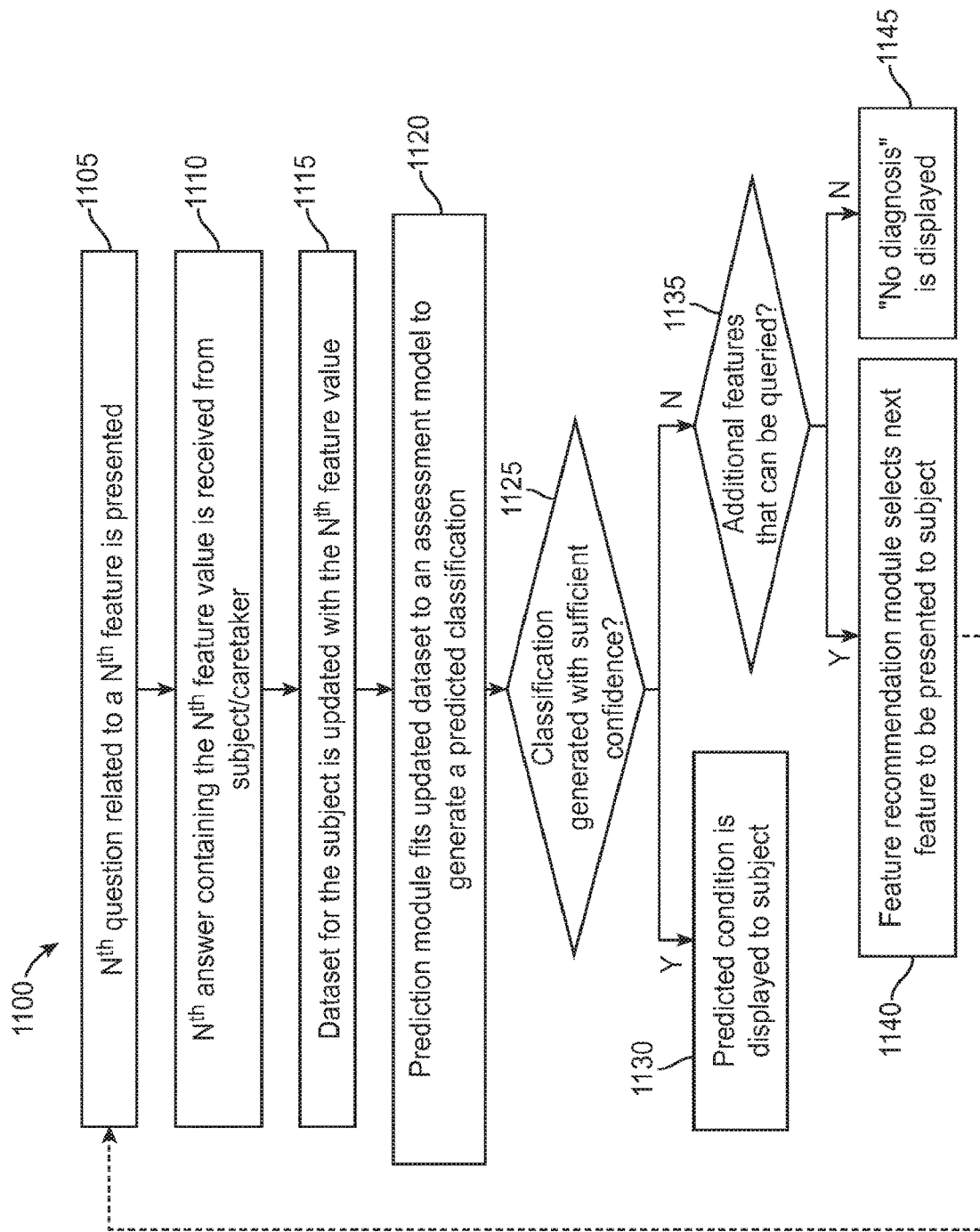
FIG. 11 illustrates a method of administering a diagnostic test as described herein, in accordance with some embodiments.

FIG. 11 illustrates a method 1100 of administering an assessment procedure as described herein. The method 1100 may be performed with a user interface provided on a computing device, the computing device comprising a display and a user interface for receiving user input in response to the instructions provided on the display. The user participating in the assessment procedure may be the subject himself, or another person participating in the procedure on behalf of the subject, such as the subject's caretaker. At step 1105, an $N^{th}$ question related an $N^{th}$ feature can be presented to the user with the display. At step 1110, the subject's answer containing the corresponding $N^{th}$ feature value can be received. At step 1115, the dataset for the subject at hand can be updated to include $N^{th}$ the feature value provided for the subject. At step 1120, the updated dataset can be fitted to an assessment model to generate a predicted classification. Step 1120 may be performed by a prediction module, as described herein. At step 1125, a check can be performed to determine whether the fitting of the data can generate a prediction of a specific developmental disorder (e.g., autism, ADHD, etc.) sufficient confidence (e.g., within at least a 90% confidence interval). If so, as shown at step 1130, the predicted developmental disorder can be displayed to the user. If not, in step 1135, a check can be performed to determine whether there are any additional features that can be queried. If yes, as shown at step 1140, the feature recommendation module may select the next feature to be presented to the user, and steps 1105-1125 may be repeated until a final prediction (e.g., a specific developmental disorder or "no diagnosis") can be displayed to the subject. If no additional features can be presented to the subject, "no diagnosis" may be displayed to the subject, as shown at step 1145.

Although the above steps show an exemplary a method 1100 of administering an assessment procedure, a person of ordinary skill in the art will recognize many variations based on the teachings described herein. The steps may be completed in a different order. Steps may be added or deleted. Some of the steps may comprise sub-steps of other steps. Many of the steps may be repeated as often as desired by the user.

Figure 12:
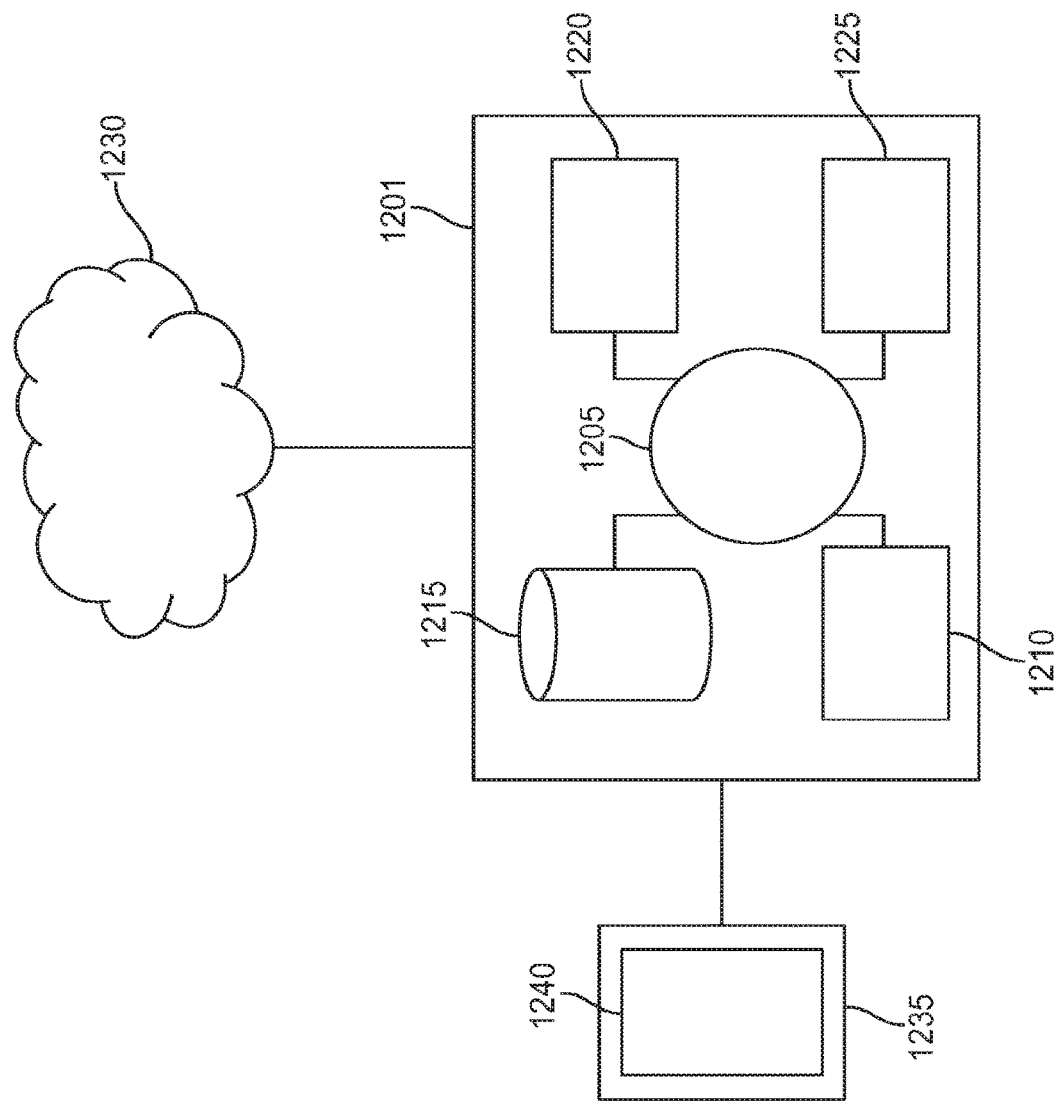
FIG. 12 shows an exemplary computer system suitable for incorporation with the methods and apparatus described herein, in accordance with some embodiments.

The present disclosure provides computer control systems that are programmed to implement methods of the disclosure. FIG. 12 shows a computer system 1201 suitable for incorporation with the methods and apparatus described herein. The computer system 1201 can process various aspects of information of the present disclosure, such as, for example, questions and answers, responses, statistical analyses. The computer system 1201 can be an electronic device of a user or a computer system that is remotely located with respect to the electronic device. The electronic device can be a mobile electronic device.

The computer system 1201 includes a central processing unit (CPU, also "processor" and "computer processor" herein) 1205, which can be a single core or multi core processor, or a plurality of processors for parallel processing. The computer system 1201 also includes memory or memory location 1210 (e.g., random-access memory, read-only memory, flash memory), electronic storage unit 1215 (e.g., hard disk), communication interface 1220 (e.g., network adapter) for communicating with one or more other systems, and peripheral devices 1225, such as cache, other memory, data storage and/or electronic display adapters. The memory 1210, storage unit 1215, interface 1220 and peripheral devices 1225 are in communication with the CPU 1205 through a communication bus (solid lines), such as a motherboard. The storage unit 1215 can be a data storage unit (or data repository) for storing data. The computer system 1201 can be operatively coupled to a computer network ("network") 1230 with the aid of the communication interface 1220. The network 1230 can be the Internet, an internet and/or extranet, or an intranet and/or extranet that is in communication with the Internet. The network 1230 in some cases is a telecommunication and/or data network. The network 1230 can include one or more computer servers, which can enable distributed computing, such as cloud computing. The network 1230, in some cases with the aid of the computer system 1201, can implement a peer-to-peer network, which may enable devices coupled to the computer system 1201 to behave as a client or a server.

The CPU 1205 can execute a sequence of machine-readable instructions, which can be embodied in a program or software. The instructions may be stored in a memory location, such as the memory 1210. The instructions can be directed to the CPU 1205, which can subsequently program or otherwise configure the CPU 1205 to implement methods of the present disclosure. Examples of operations performed by the CPU 1205 can include fetch, decode, execute, and writeback.

The CPU 1205 can be part of a circuit, such as an integrated circuit. One or more other components of the system 1201 can be included in the circuit. In some cases, the circuit is an application specific integrated circuit (ASIC).

The storage unit 1215 can store files, such as drivers, libraries and saved programs. The storage unit 1215 can store user data, e.g., user preferences and user programs. The computer system 1201 in some cases can include one or more additional data storage units that are external to the computer system 1201, such as located on a remote server that is in communication with the computer system 1201 through an intranet or the Internet.

The computer system 1201 can communicate with one or more remote computer systems through the network 1230. For instance, the computer system 1201 can communicate with a remote computer system of a user (e.g., a parent). Examples of remote computer systems and mobile communication devices include personal computers (e.g., portable PC), slate or tablet PC's (e.g., Apple® iPad, Samsung® Galaxy Tab), telephones, Smart phones (e.g., Apple® iPhone, Android-enabled device, Blackberry®), personal digital assistants, wearable medical devices (e.g., Fitbits), or medical device monitors (e.g., seizure monitors). The user can access the computer system 1201 with the network 1230.

Methods as described herein can be implemented by way of machine (e.g., computer processor) executable code stored on an electronic storage location of the computer system 1201, such as, for example, on the memory 1210 or electronic storage unit 1215. The machine executable or machine readable code can be provided in the form of software. During use, the code can be executed by the processor 1205. In some cases, the code can be retrieved from the storage unit 1215 and stored on the memory 1210 for ready access by the processor 1205. In some situations, the electronic storage unit 1215 can be precluded, and machine-executable instructions are stored on memory 1210.

The code can be pre-compiled and configured for use with a machine have a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 401, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1201 can include or be in communication with an electronic display 1235 that may comprise a user interface (UI) 1240 for providing, for example, questions and answers, analysis results, recommendations. Examples of UI's include, without limitation, a graphical user interface (GUI) and web-based user interface.

Methods and systems of the present disclosure can be implemented by way of one or more algorithms and with instructions provided with one or more processors as disclosed herein. An algorithm can be implemented by way of software upon execution by the central processing unit 1205. The algorithm can be, for example, random forest, graphical models, support vector machine or other.

Although the above steps show a method of a system in accordance with an example, a person of ordinary skill in the art will recognize many variations based on the teaching described herein. The steps may be completed in a different order. Steps may be added or deleted. Some of the steps may comprise sub-steps. Many of the steps may be repeated as often as if beneficial to the platform.

Each of the examples as described herein can be combined with one or more other examples. Further, one or more components of one or more examples can be combined with other examples.

Figure 13:
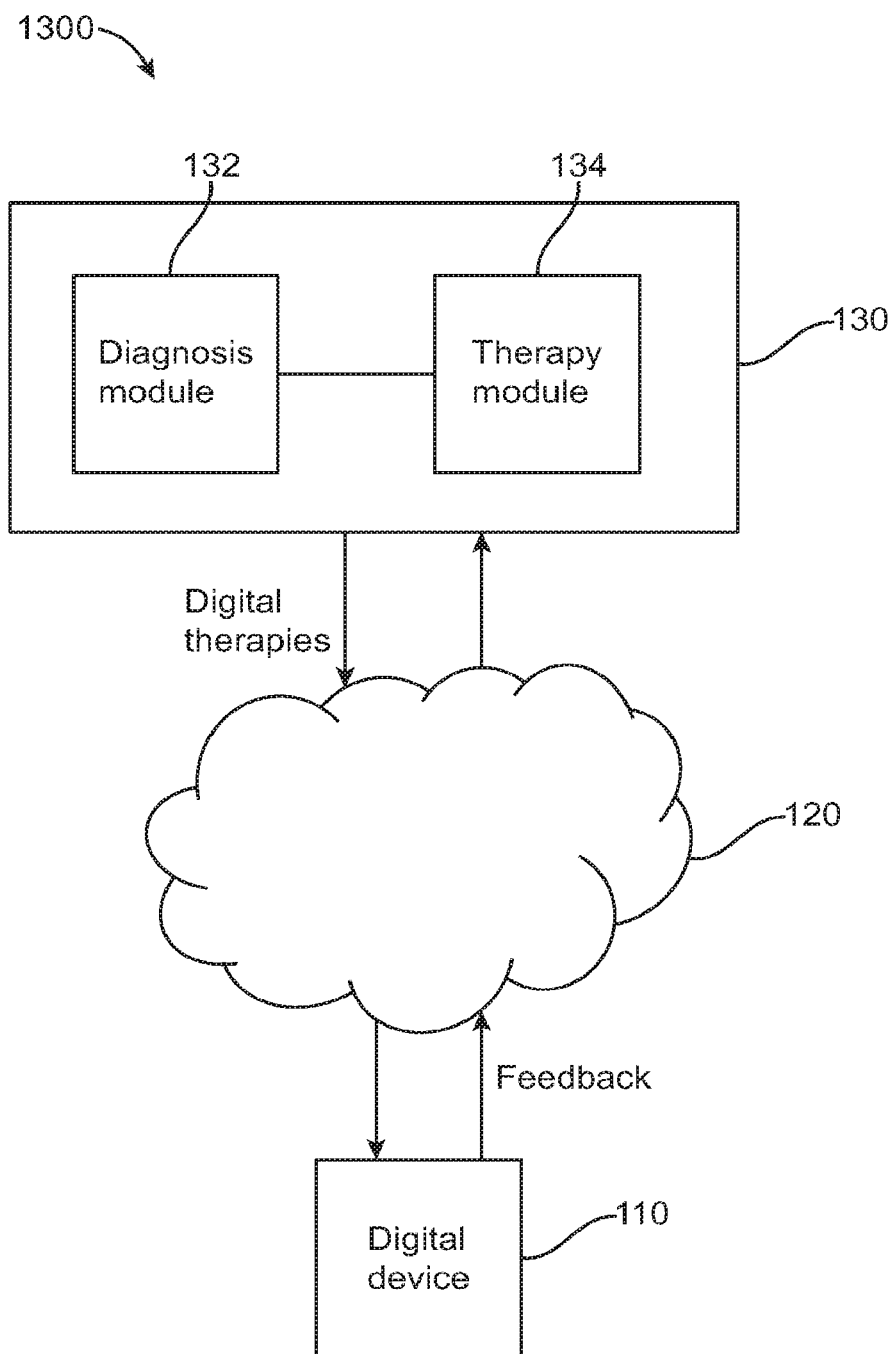
FIG. 13 illustrates an exemplary system diagram for a digital personalized medicine platform with a feedback loop and reduced tests, in accordance with some embodiments.

FIG. 13 illustrates an exemplary system diagram for a digital personalized medicine platform 1300 with a feedback loop and reduced tests. The platform 1300 can provide diagnosis and treatment of pediatric cognitive and behavioral conditions associated with developmental delays, for example. A user digital device 110, for example a mobile device such as a smart phone, an activity monitors, or a wearable digital monitor, can records data and metadata related to a subject. Data may be collected based on interactions of the subject with the device, as well as based on interactions with caregivers and health care professionals, as discussed hereinabove.

The digital device 110 can communicate with a personalized medical system 130 over a communication network 120. The personalized medical system 130 may comprise a diagnosis module 132 to provide initial and updated diagnosis of a subject's developmental status, and a therapeutic module 134 to provide personalized therapy recommendations in response to the diagnoses of diagnosis module 132.

In some instances, the diagnosis module 132 can comprise data processing module as described herein. The data processing module can enable the diagnosis module 132 to provide an assessment on the subject with reduced number of test questions. The data processing module can comprise a preprocessing module, a training module and a prediction module as described herein. The data processing module can extract training data from a database or a user, apply one or more transformations to standardize the training data and pass the standardized training data to the training module. The training module can utilize a machine learning algorithm or other algorithm to construct and train an assessment model to be used in the diagnostic tests, based on the standardized training data. Once an assessment model is derived from the training data, the model may be used as a prediction tool to assess the risk of a subject for cognitive function such as developmental advancement, or one or more disorders such as behavioral, neurological or mental health disorders. The training data can comprise data developed on a population where the subject is not a member of the population. The prediction module can be configured to generate a predicted classification of cognitive function (e.g., developmental disorder) of a given subject, by fitting new data to an assessment model constructed in the training module. The data processing module can identify a most predictive next question based on a plurality of answers to a plurality of asked questions, as discussed herein, such that a person can be diagnosed or identified as at risk and treated with fewer questions.

Diagnostic tests (for example, a set of tests and questions) as generated from the diagnosis module 132 can be provided to the subject or caregiver via the digital device 110. The subject's answers to the diagnostic tests can be received by the diagnosis module 132. The diagnosis module 132 can generate an initial diagnosis based on the subject's answers. For example, the diagnostic module may diagnose autism-related speech delay based on questions asked to the caregiver and tests administered to the subject such as vocabulary or verbal communication tests.

The diagnosis module can communicate its initial diagnosis to the therapeutic module 134, which uses the initial diagnosis to suggest initial therapies to be performed to treat any diagnosed symptoms. The therapeutic module 134 sends its recommended therapies to the digital device 110, including instructions for the subject and caregivers to perform the therapies recommended over a given time frame. The subject and caregivers can provide feedback to the diagnostic module 132, and the diagnostic module 132 can then instruct the data processing module to provide new diagnostic tests and questions to the digital device 110. The diagnostic module 132 then provides an updated diagnosis to the therapeutic module 134 which suggests updated therapies to be performed by the subject and caregivers as a next step of therapy. Therefore, a feedback loop between the subject and caregivers, the diagnostic module and the therapeutic module can be formed, and the subject can be diagnosed with fewer questions. The feedback can identify relative levels of efficacy, compliance and responses resulting from the therapeutic interventions, and allow corrective changes to improve treatment.

In some instances, the therapeutic module may rely on the diagnostic module in order to classify subjects as having different conditions or different severity levels of a condition. Optionally, the therapeutic module can have its own independent prediction module or recommendation module in order to decide on next best therapy or treatment from a list of options. This decision can take into account the assessment from the diagnostic module, as well as independently compiled statistics relating to the historical probability for certain subjects to respond to certain treatments, broken down by demographics like gender/age/race/etc. The therapeutic module can perform the predictive task using simple rules or sophisticated machine learning techniques. In the case of machine learning, an independent feedback loop would take place, connecting subject treatment outcome back to the therapeutic module.

In some instances, a third-party system, such as a computer system of a health care professional, can be connected to the communication network 120. The health care professional or other third party can be alerted to significant deviations from the diagnosis provided by the diagnostic module and/or therapies suggested by the therapeutic module based on the reduced number of questions. Appropriate further action can then be taken by the third party. For example, third-party system can review and modify therapies suggested by the therapeutic module.

In some instances, the subject can have response profiles in response to the therapies, and the therapeutic module can be configured to categorize the response profiles based on an initial response of the subject. For example, the subject could have a response profile that indicates the treatment is working or a response profile indicating that treatment is not working. These initial response profiles can be somewhat counter intuitive. For example, a fluctuation in symptoms could be an indicator that the treatment is working even though these fluctuations could include an increase and a decrease in a symptom relative to baseline. For some treatments, the time at which there's a change in symptoms could be delayed.

The user, such as the subject and caregivers, can for example download and install an App comprising software instructions on the digital device 110. The App can enable the user to receive instructions from the cloud-based server for the diagnostic tests, upload the answers to diagnostic tests, receive a treatment (for example, games or interactive content) from the cloud-based server, offer feedback, periodically receive new tests to determine how the treatment is progressing, and receive updated treatment. The app can be installed on a plurality of digital devices, such as a first device for the subject to receive digital therapy and second device for the caregiver to monitor progress of the therapy. A feedback loop is thus created between the user and the cloud-based server (for example, the personalized medicine system 130), in which the evaluation of the subject subsequent to the initiation of therapy is used to adjust therapy to improve the response.

Figure 14:
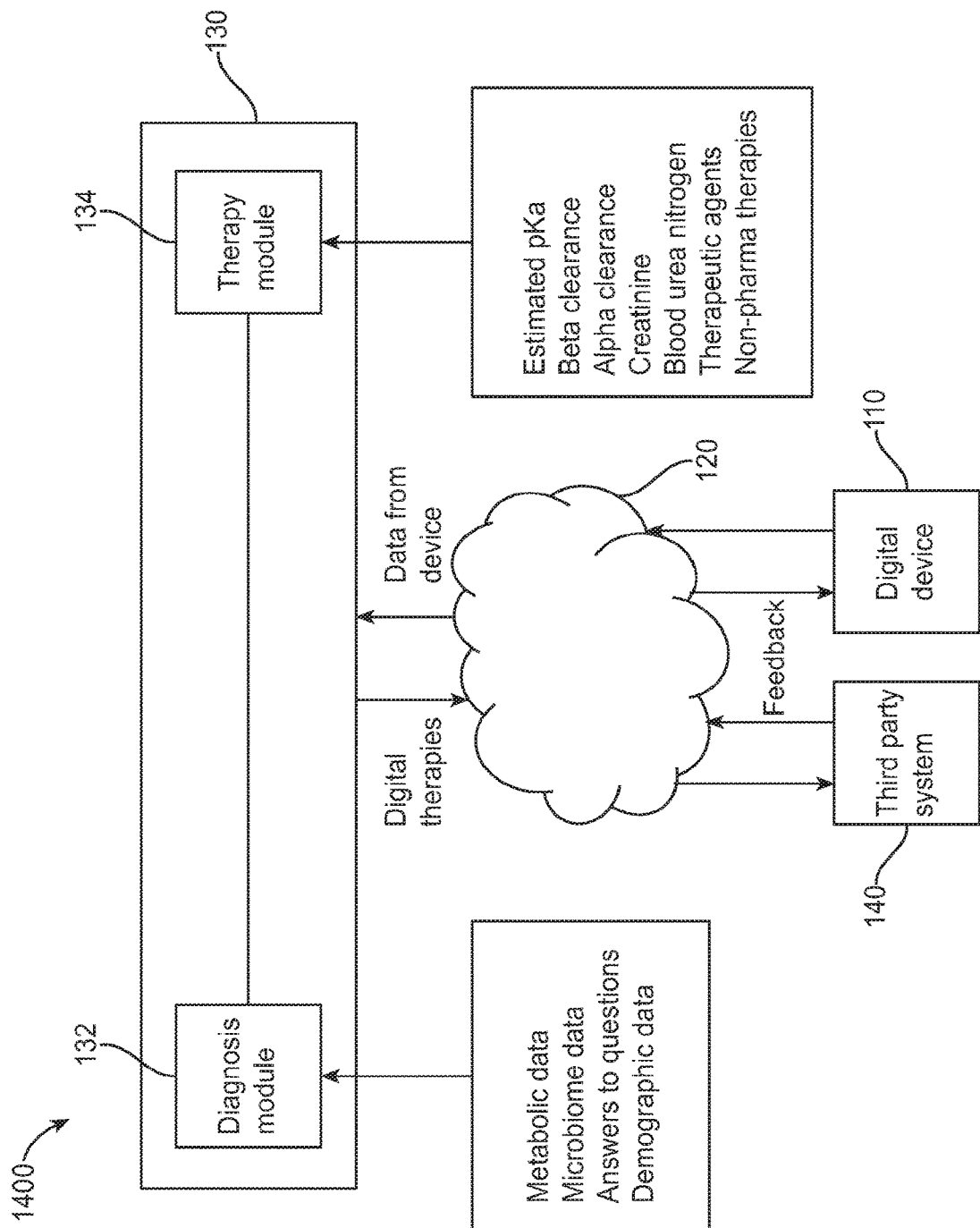
FIG. 14 illustrates an exemplary system diagram for a digital personalized medicine platform with a feedback loop, in accordance with some embodiments.

FIG. 14 illustrates an exemplary system diagram for a digital personalized medicine platform with a feedback loop. The platform 1400 may comprise any one or more of the elements of the platform 1300 of FIG. 13, such as the personalized medical system 130, the diagnosis module 132, the therapeutic module 134, the computer network 120, or the digital device 110, as described herein. The platform 1400 may further comprise a third-party system 140, as described herein. The personalized medical system 130 may be configured to communicate information regarding digital therapies to the computer network 120 and/or configured to receive information regarding device data from the computer network 120. The third-party system 140 may be configured to send and/or receive information to and/or from the computer network 120.

The diagnosis module may be configured to receive information regarding one or more pieces of diagnostic information. For instance, the diagnosis module may be configured to receive metabolic data, microbiome data, one or more answers to one or more questions asked during one or more assessments, and/or demographic data (such as a user's age, sex, height, weight, diagnostic status for one or more disorders, and/or any other demographic data as is known to one having skill in the art). For instance, the diagnosis module may be configured to receive metabolic data that may be relevant to behavioral disorders such as autism spectrums disorders, attention deficits disorders, bipolar disorder, schizophrenia, epilepsy, cerebral palsy, and/or any other behavioral disorder as is known to one having skill in the art. The metabolic data may be relevant to assessing the efficacy of treatment of the disorder with a drug or other therapeutic. For instance, the metabolic data may be relevant to assessing the efficacy of the use of an antipurinergic therapy to treat a behavioral disorder, such as autism. The metabolic data may be relevant to assessing the efficacy of the use of suramin (8-[[4-methyl-3-[[3-[[2-methyl-5-[(4,6,8-trisulfonaphthalen-1-yl)carbamoyl]phenyl]carbamoyl]phenyl]carbamoylamino]bhenzoyl]amino] benzoyl]amino]naphthalene-1,3,5-trisulfonic acid) to treat a behavioral disorder, such as autism, for example.

The metabolic data may comprise measurements of blood levels of one or more metabolites associated with the use of suramin to treat autism. For instance, the metabolic data may comprise blood levels of one or more of creatinine, xanthine, hypoxanthine, inosine, LTB4, guanosine, 1-methylnicotinamide, 11-dehydro-thromboxane B2, 4-hydroxyphenyllactic acid, L-cystine, hexanoylcarnitine, dihexosylceramide, ceramide, 2,3-diphosphoglyceric acid, phosphatidyl inositol, cysteine-glutathione disulfide, D-glucose, trihexosylceramide, bismonoacylphospholipid, malondialdehyde, phosphatidylcholine, 3,5-tetradecadiencarnitine, epoxy-5,8,11-eicosatrienoic acid, cardiolipin, 8,9-epoxyeicosatrienoic acid, myristoylcarnitine, cholic acid, octanoylcarnitine, pimelylcarnitine, dodecynoylcarnitine, L-homocysteic acid, 9-decenoylcarnitine, hydroxyisocaproic acid, propionic acid, 5-alpha-cholestanol, glyceric acid 1,3-biphosphate, 3-methylphenylacetic acid, cytidine, oxaloacetic acid, 9-hexadecenoylcarnitine, dehydroisoandrosterone 3-sulfate, 11-R-hydroxyeicosatetraenoic acid, pyridoxamine, 11,12-dihydroxyeicosatrienoic acid, sedoheptulose 7-phosphate, and/or 5-aminoimidazole-4-carboxamide ribonucleotide.

The blood levels of the metabolites may be associated with metabolic pathways involved in creatine or creatinine metabolism, purine metabolism, eicosanoid metabolism, resolvin metabolism, vitamin B3 metabolism, nicotinamide adenine dinucleotide metabolism, microbiome metabolism, fatty acid oxidation and/or synthesis, ganglioside metabolism, sphingolipid metabolism, glycolysis and/or gluconeogenesis, S-adenosylmethionine metabolism, S-adenosylhomocysteine metabolism, glutathione metabolism, phospholipid metabolism, nitric oxide metabolism, reactive oxygen species metabolism, cardiolipin metabolism, bile salt metabolism, cholesterol metabolism, cortisol metabolism, steroid metabolism, oxalate metabolism, glyoxylate metabolism, tryptophan metabolism, Krebs cycle, gamma-aminobutyric acid metabolism, glutamate metabolism, arginine metabolism, ornithine metabolism, proline metabolism, pyrimidine metabolism, vitamin B2 metabolism, thyroxine metabolism, amino-sugar metabolism, galactose metabolism, methionine metabolism, biopterin metabolism, neopterin metabolism, and/or molybdopterin metabolism.

The therapeutic module may be configured to determine information regarding one or more pieces of therapeutic information. For instance, the therapeutic module may be configured to determine an estimated pharmacokinetic ("PK") parameter of a therapeutic agent, such as an estimated alpha clearance rate, or an estimated beta clearance rate, for example. The PK parameter can be determined in response to measured physiological parameters of the subject, or demographic data. The PK parameter can be used to determine estimate amounts of the therapeutic agent in the subject. The therapeutic module can estimate biomarkers levels such as creatinine level, blood urea nitrogen level, in response to the data provided to the diagnostic module. The PK parameter can be used to determine a therapeutic agent level, or an estimated non-pharma therapy level, for example. The therapeutic module may utilize models determined by machine learning, a classifier, artificial intelligence, or statistical modeling to determine information regarding the pieces of therapeutic information.

The classifier of the therapeutic module or the diagnostic module may be configured to produce one or more cognitive function scores, as described herein. These cognitive function scores may correspond to an ADOS score or a Vineland Adaptive Behavior Scale score, for example, so as to allow a determination of where the subject is in the autistic spectrum, for example. Similar scores can be developed for other cognitive functions as described herein by a person of ordinary skill in the art. The relative weight of each answer can be combined with other answers for the subject and used to determine the cognitive score for the subject. The cognitive score of the subject can be determined in response to the feature importance for each question as described herein, for example. The cognitive score can be determined based on a combination of the question feature importance and the answer to the question for each of the plurality of questions. A magnitude of the cognitive score may be indicative of the severity of a behavioral disorder at a particular moment in time, for example. A change in the magnitude of the cognitive score may be indicative of a change in state of the behavioral disorder, such as may occur in response to a therapeutic intervention, a treatment, or a progression of the disorder. For example the score may be related to where the subject falls on the autism spectrum, e.g. from autism to Asperger's syndrome.

The diagnostic or therapeutic module may further comprise a second diagnostic or therapeutic classifier that can assess a patient's behavior or performance. The assessment may be based directly on answers to a plurality of questions related to a cognitive function of the patient or can be based in combination with passive data obtained from or related to the patient or data obtained or collected from third parties. The second classifier may assign a numerical score to the patient's behavior or performance. The second classifier may compare the numerical score of a patient, or a change in the numerical score, to scores obtained from other patients or other cohorts to determine relative values. For instance, the second classifier may compare the numerical score, or a change in the numerical score, to scores obtained from other patients or cohorts that are in some way similar to the patient, such as in age or other demographics. The classifier may determine a numerical comparison between the patient and other similar patients or cohorts. For instance, the classifier may determine that the patient's behavior or performance falls within a particular percentile rank compared to other similar patients or cohorts. The classifier may also provide a milestone or developmental skills assessment. The diagnostic or therapeutic module may compare a value or a change in value of a patient's score or other assessment metric over time to other patients defined by a similar or like cohort. Based on this comparison or matching of a patient's score or assessment metric to similar cohorts, which may be made for example at particular milestones, the therapeutic module may determine and output a personal therapeutic treatment plan for the patient.

A plurality of questions can be answered at each of a plurality of separate times, such as pre-treatment, 3 weeks post treatment, 6 weeks post treatment, etc., and the score determined at each of the plurality of follow up times. The dosage can be adjusted in response to the score generated for each of the plurality of times. The score from the diagnostic module can be transmitted to the therapeutic module to determine the appropriate dosage of the subject in response to the answers at each of the plurality of times, for example.

The system of FIG. 14 may be utilized to determine a therapeutic plan for a subject. The therapeutic module may be configured to determine a personal therapeutic treatment plan in response to diagnostic data for a subject. The therapeutic plan may comprise the timing or amount of a dose of a therapeutic agent. The diagnostic module may be configured to receive updated subject data from a subject in response to therapy of the subject. The diagnostic module may generate updated diagnostic data based on the updated subject data. The therapeutic module may be configured to receive the updated diagnostic data to determine an updated amount or an updated timing for administering an updated dose of a therapeutic agent. The therapeutic module may be configured to output an updated personal treatment plan for the subject in response to the diagnostic data or the updated diagnostic data. The personal therapeutic treatment plan may comprise an updated amount or updated timing of administering the updated dosage of the therapeutic agent.

The therapeutic module may be configured to determine the timing or amount of a dose of the therapeutic agent in response to measured pharmacokinetics of a subject. The therapeutic agent may have an alpha elimination half-life and/or a beta elimination half-life. The beta elimination half-life may comprise a time within a range from about 1 day to 30 days, for example. The therapeutic module may be configured to determine an amount and/or a timing of a subsequent dose of the therapeutic agent in response to the beta elimination half-life. The pharmacokinetics of the subject may be determined in response to administering a known amount of the therapeutic agent to the subject at a first time and determining an amount of the therapeutic agent at one or more later times.

The therapeutic module may be configured to determine the timing or amount of the dosage of the therapeutic agent in response to an estimated beta clearance rate of the subject based on the demographics of the subject. The demographics may be the subject's height, weight, age, or gender.

The therapeutic agent may comprise suramin, for example. The subject may be a pediatric subject. The suramin may be injected into the subject. The injected amount may be within a range from about 10 mg of suramin per kg of body weight to about 30 mg of suramin per kg of body weight of the subject. The therapeutic module may be configured to target a suramin blood concentration within a range from about 1 µM to about 100 µM.

Figure 15:
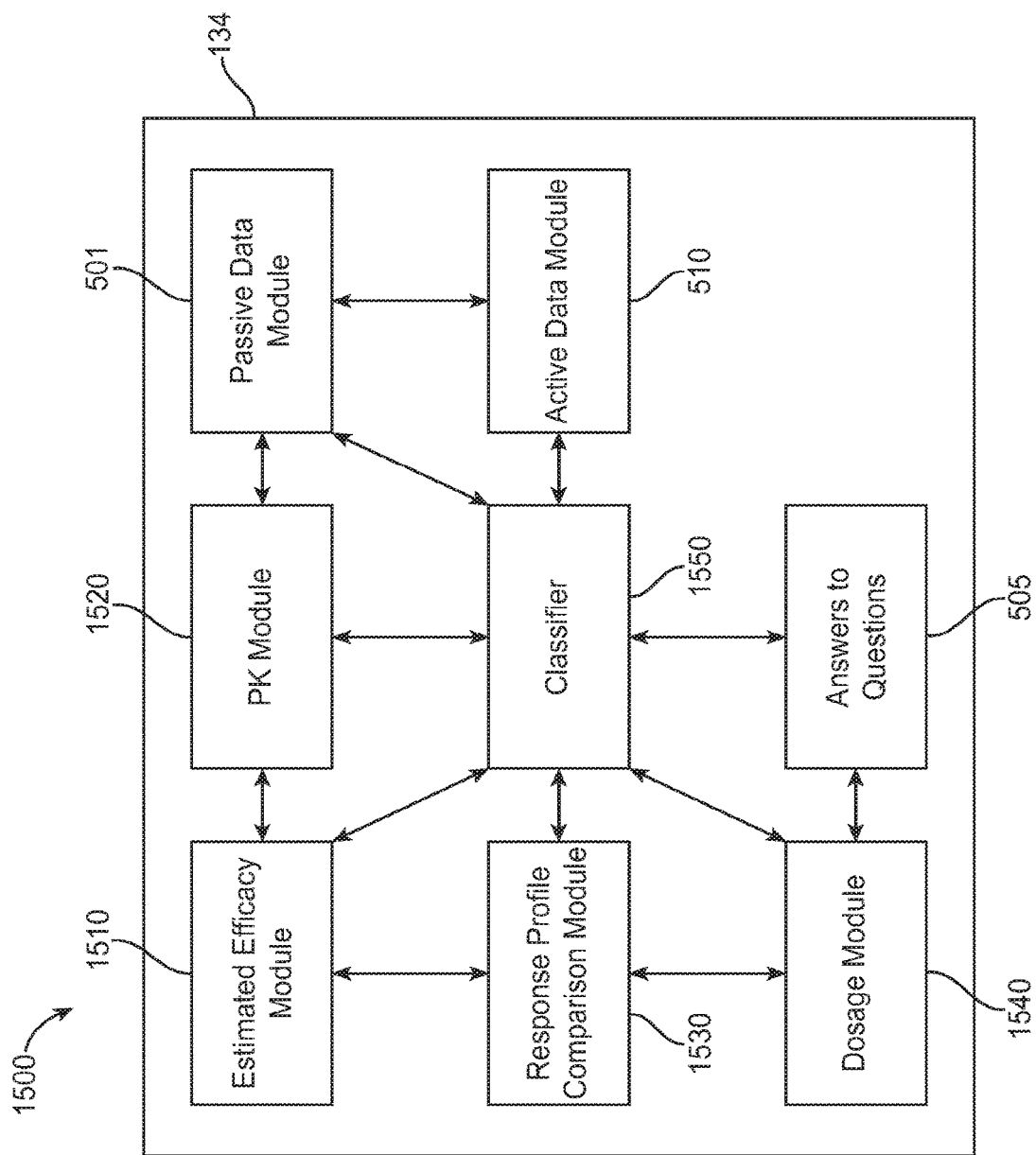
FIG. 15 shows an exemplary system diagram for a therapeutic module, in accordance with some embodiments.

FIG. 15 shows an exemplary system diagram for a therapeutic module 1500. The therapeutic module 134 may comprise a classifier 1550, passive data module 501, active data module 510, and/or answers to questions 505, as described herein. The classifier 1500 may comprise one or more components similar to classifier 600 as described herein. The classifier 1550 may comprise a separate classifier from classifier 600, or the classifiers may be combined, such that classifier 1550 may comprise a combined diagnosis and treatment module, comprising at least some components of classifier 600. Alternatively or in combination, classifier 600 can be configured to transmit and receive data from classifier 1550. Also, the therapeutic module 1500 may comprise components of the diagnostic module as described herein, such that therapeutic module 1500 comprises a combined diagnosis and therapeutic module.

The therapeutic module may further comprise an estimated efficacy module 1510, a PK module 1520, a response profile comparison module 1530 and/or a dosage module 1540. Any element of the therapeutic module may be configured to communicate with any other element of the therapeutic module. For instance, the classifier may be configured to communicate with the estimated efficacy module, passive data module, PK module, response profile comparison module, active data module, dosage module, and/or answers to questions. The estimated efficacy module may be configured to communicate with the classifier, passive data module, PK module, response profile comparison module, active data module, dosage module, and/or answers to questions. The passive data module may be configured to communicate with the classifier, estimated efficacy module, PK module, response profile comparison module, active data module, dosage module, and/or answers to questions. The PK module may be configured to communicate with the classifier, estimated efficacy module, passive data module, response profile comparison module, active data module, dosage module, and/or answers to questions. The response profile comparison module may be configured to communicate with the classifier, estimated efficacy module, passive data module, PK module, active data module, dosage module, and/or answers to questions. The active data module may be configured to communicate with the classifier, estimated efficacy module, passive data module, PK module, response profile comparison module, dosage module, and/or answers to questions. The dosage module may be configured to communicate with the classifier, estimated efficacy module, passive data module, PK module, response profile comparison module, active data module, and/or answers to questions. The answers to questions may be configured to communicate with the classifier, estimated efficacy module, passive data module, PK module, response profile comparison module, active data module, and/or dosage module.

The estimated efficacy module may communicate with the other elements of the therapeutic module to determine an estimated efficacy of a therapy. For instance, the estimated efficacy module may communicate with the classifier, passive data module, active data module, PK module, and dosage module to determine the efficacy of administration of a drug with a particular dosage and PK to treat a behavioral disorder. The PK module may communicate with the other elements of the therapeutic module to estimate a PK of a drug. The response profile comparison module may communicate with the other elements of the therapeutic module to compare a response profile of a given individual and a given course of treatment to other individuals being treated with the same treatment or a different treatment. The dosage module may communicate with the other elements of the therapeutic module to determine a dosage (such as an amount and timing of a dosage) for a drug therapy.

The PK module 1520 can be configured with PK parameters for the subject as described herein. The PK module can be used to determine the amount of therapeutic agent in the blood of the subject over time, for example a profile of a therapeutic agent in response to an amount of therapeutic agent from the dosage module. The PK module can be configured to determine the profile and area under the curve ("AUC") of the therapeutic agent overtime in the blood of the subject, and transmit this data to the estimated efficacy module 1510. The estimated efficacy module 1510 can compare the profile over time in the blood of the subject with target therapeutic amounts of the therapeutic agent and estimate the overall efficacy of the subject. The estimated efficacy module may produce any data related to the estimated overall efficacy of the subject.

The dosage module 1540 can be configured to store and modify the timing and amount of the therapeutic agent. The dosing module can be configured to determine the dosing of the subject in response to the therapeutic agent. The dosing module can provide input to the estimated efficacy module 1510.

The estimated efficacy module 1510 can be configured to estimate the efficacy of the therapeutic agent in response to the dosage provided by the dosage module 1540 and the PK module 1520. The estimated efficacy module can determine the estimated efficacy of the therapeutic agent in response to profile of the therapeutic agent in the blood overtime determined with the PK module and the dosage of therapeutic agent. The response profile comparison module can be configured to compare response profiles of subjects based on subject specific data such as biomarkers, demographics, data provided from the answers to questions module 505, data provided from the passive data module 501, and data provided from active data module 510.

Each of the plurality of modules therapeutic module 1500, such as modules 501, 505, 510, 1510, 1530 and 1540, can be configured with its own classifier in order to determine the relevant data to be provided to the other modules. The classifier of said each of the plurality of modules may comprise one or more components of classifier 600 as described herein.

Figure 16:
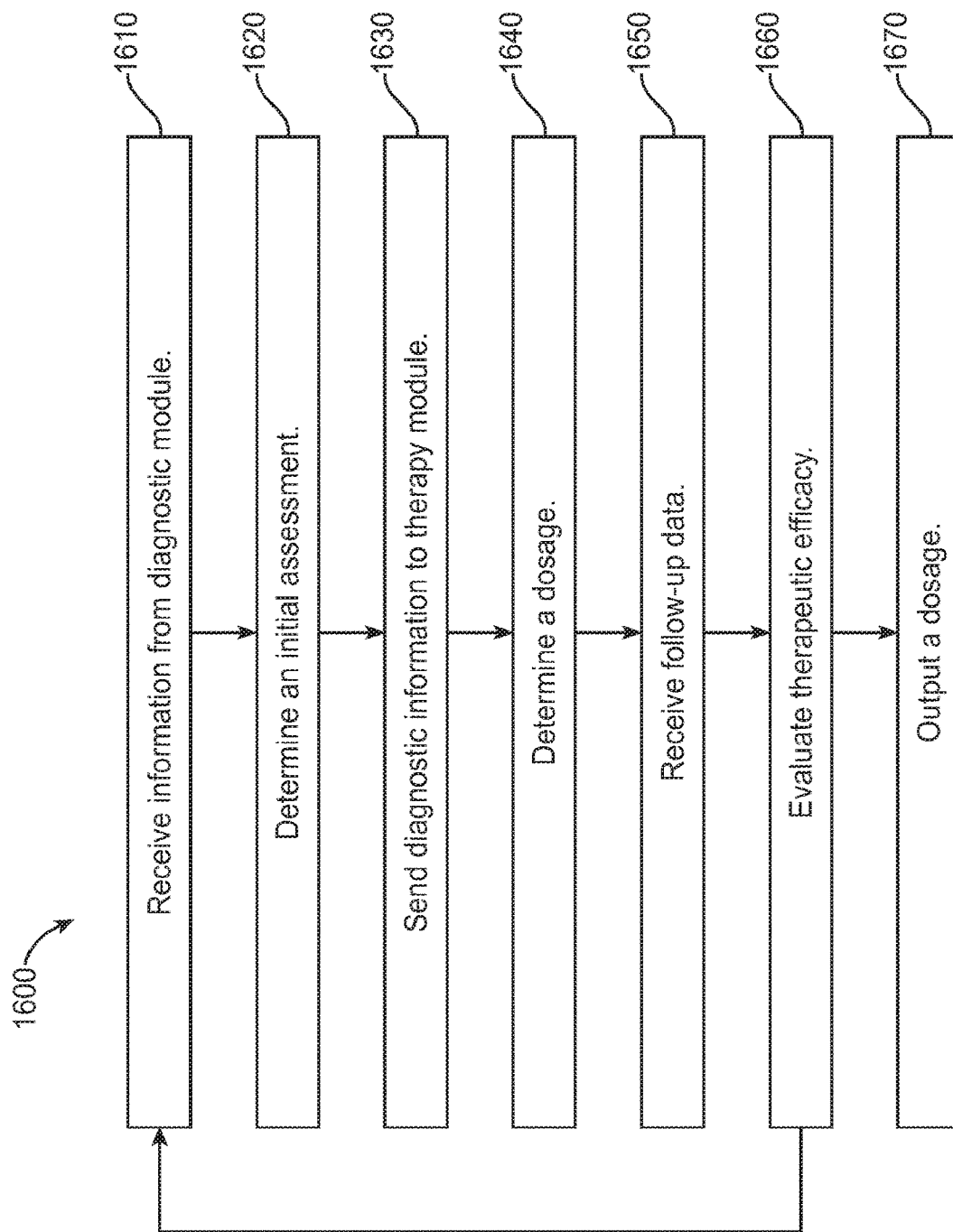
FIG. 16 shows a flowchart for a method of determining a dosage of a therapeutic agent, in accordance with some embodiments.

FIG. 16 shows a flowchart for a method of determining a dosage of a therapeutic agent. The method 1600 may comprise the steps of receiving information from the diagnostic module, determining an initial assessment, sending diagnostic information to the therapeutic module, determining a dosage, receiving follow-up data, evaluating therapeutic efficacy, and outputting a dosage.

In step 1610, information is received from the diagnostic module. The information may comprise any information utilized by the diagnostic module, as described herein.

In step 1620, an initial assessment is determined. The initial assessment may comprise a preliminary assessment of a subject's cognitive function determined by the diagnostic module, as described herein.

In step 1630, diagnostic information is sent to the therapeutic module. The diagnostic information may comprise any information relevant to a diagnosis of a subject's cognitive function determined by the diagnostic module, as described herein. For instance, the diagnostic information may comprise a diagnosis that the subject suffers from an autism spectrum disorder or other behavioral disorder.

In step 1640, a dosage is determined. The dosage may comprise an amount and/or a timing of the dosage. The dosage may be determined by the dosage module, as described herein.

In step 1650, follow-up data is received. The follow-up data may comprise any information that allows the efficacy of the treatment to be assessed, as described herein. For instance, the follow-up data may comprise blood metabolite levels that may allow a determination of the efficacy of a treatment using a pharmaceutical, as described herein.

In step 1660, the therapeutic efficacy is determined. If the therapeutic efficacy is determined to fall below a threshold efficacy, steps 1610, 1620, 1630, 1640, 1650, and 1660 may be repeated. If the therapeutic efficacy meets or exceeds the threshold efficacy, dosage information is output in step 1670.

The systems and methods described herein may be used to determine a treatment plan for using a therapeutic agent.

Figure 17:
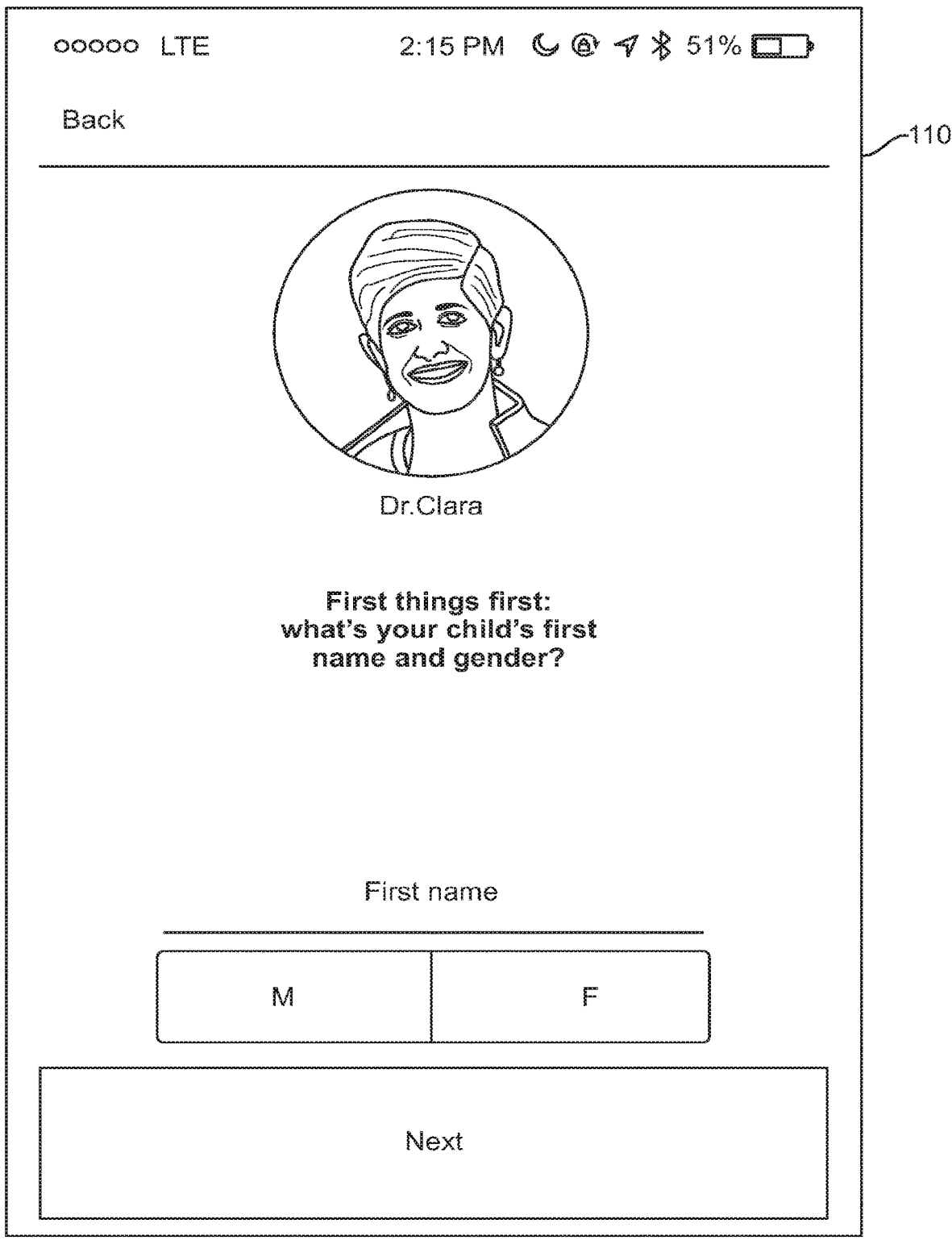
FIG. 17 shows a graphical user interface for use with a digital personalized medicine platform that prompts a user for a child's demographic information, in accordance with some embodiments.

FIG. 17 shows a graphical user interface for use with a digital personalized medicine platform that prompts a user for a child's demographic information. The user digital device 110 may display a prompt asking for the child's first name and gender. The user digital device may comprise a data entry field for inputting the child's first name and a selection field for selecting whether the child is male or female.

FIG. 18 shows a graphical user interface for use with a digital personalized medicine platform that prompts a user for information about their child's diagnostic state. The user digital device 110 may display data entry fields for inputting the child's first name, last name, and/or date of birth. The user digital device may display selection fields for selecting whether the child is male or female and/or whether the child has been diagnosed with a behavioral disorder. The user digital device may display selection fields for selecting whether the child has been diagnosed with one or more personality disorders, such as a selection field for selecting whether the child has been diagnosed with autism spectrum disorder, a selection field for selecting whether the child has been diagnosed with attention deficit disorder, a selection field for selecting whether the child has been diagnosed with sensory processing disorder, a selection field for selecting whether the child has been diagnosed with intellectual disability, a selection field for selecting whether the child has been diagnosed with developmental delay, a selection field for selecting whether the child has been diagnosed with language delay, and/or a selection field for selecting whether the child has been diagnosed with speech delay. The user digital device may display selection fields for selecting who provided the child's diagnosis. The user digital device may a selection field for selecting whether a doctor provided the child's diagnosis, a selection field for selecting whether a clinical psychologist provided the child's diagnosis, a selection field for selecting whether a school psychologist provided the child's diagnosis, and/or a selection field for selecting whether another person provided the child's diagnosis.

FIG. 19 shows a graphical user interface for use with a digital personalized medicine platform that prompts a user for information about their child's strengths. The user digital device 110 may display selection fields for selecting whether one or more areas are areas of strength for a user's child. The user digital device may display a selection field for selecting whether the child is responsive and displays normal use of language, a selection field for selecting whether the child interacts well with other children, a selection field for selecting whether the child works well in groups, a selection field for selecting whether the child works well one-on-one, a selection field for selecting whether the child is able to organize toys and items, a selection field for selecting whether the child follows instructions well, a selection field for selecting whether the child like learning new things, a selection field for selecting whether the child is potty trained or making progress toward potty training, and/or a selection field for selecting whether the child sleeps through the night.

FIG. 20 shows a graphical user interface for use with a digital personalized medicine platform that prompts a user for information about their concerns regarding their child. The user digital device 110 may display selection fields for selecting whether one or more areas are areas of concern for a user's child. The user digital device may display a selection field for selecting whether the child displays delayed or odd use of language, a selection field for selecting whether the child displays little interaction with other children, a selection field for selecting whether the child displays problem behaviors (such as tantrums or oppositional behavior), a selection field for selecting whether the child is unable to follow commands or respond to their name, a selection field for selecting whether the child is very restless or can't sit still, a selection field for selecting whether the child displays odd or repetitive hand or finger mannerisms or body movements, a selection field for selecting whether the child displays sleep problems, a selection field for selecting whether the child display tummy troubles (such as aches, constipation, or diarrhea), a selection field for selecting whether the child displays an odd use of toys, and/or a selection field for selecting whether the child displays none of these traits.

Figure 21:
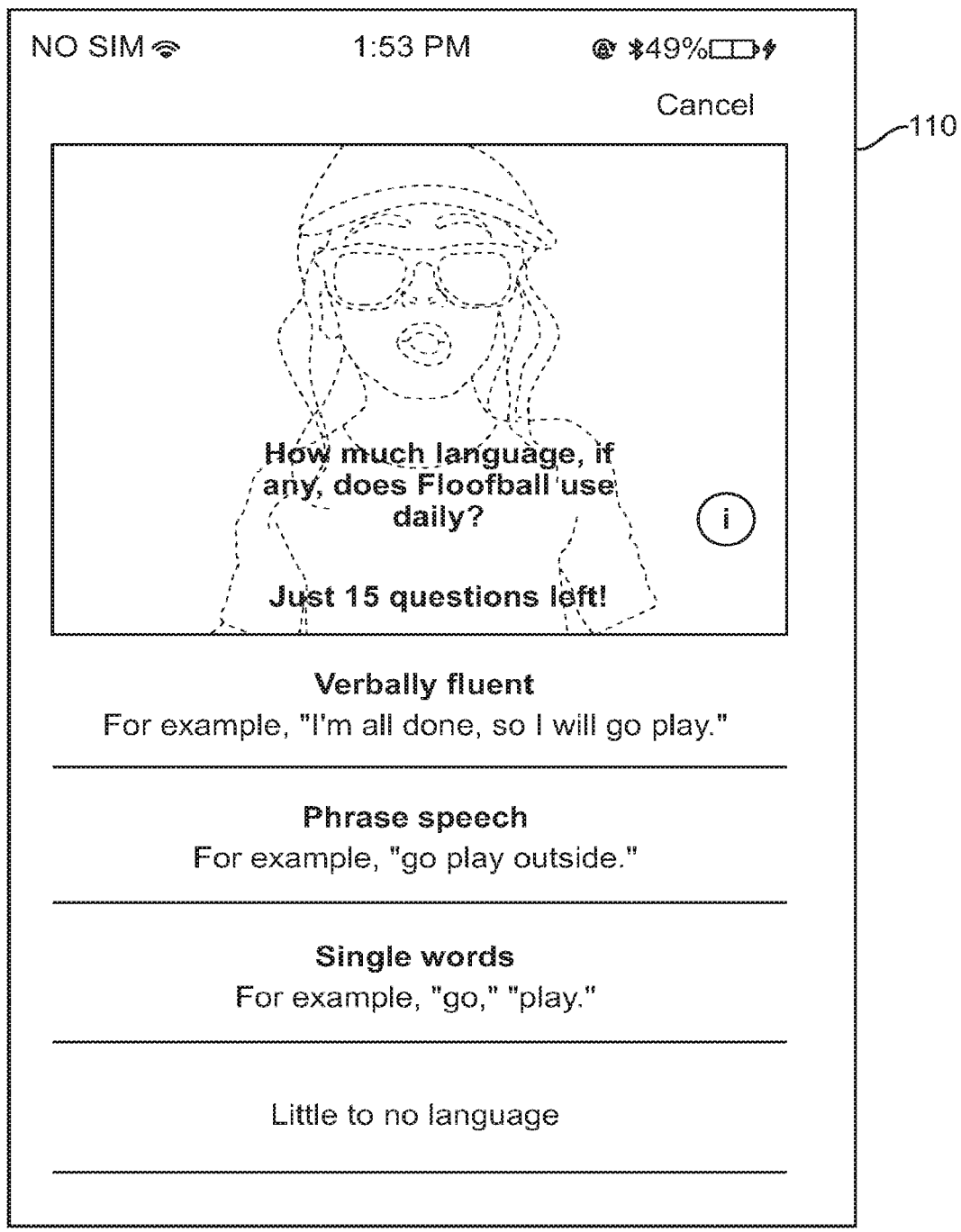
FIG. 21 shows a graphical user interface for use with a digital personalized medicine platform that prompts a user for information about their child's language usage, in accordance with some embodiments.

FIG. 21 shows a graphical user interface for use with a digital personalized medicine platform that prompts a user for information about their child's language usage. The user digital device 110 may display selection fields for selecting how much language a user's child uses on a daily basis. The user digital device may display a selection field for indicating that the child is verbally fluent (for instance, that the child uses fully-developed speech such as "I'm all done, so I will go play"), a selection field for indicating that the child uses phrase speech (for instance, that the child uses less-developed speech such as "go play outside"), a selection field for indicating that the child uses single words (for instance, that the child uses poorly-developed speech such as "go" or "play"), and/or a selection field for indicating that the child uses little to no language.

Figure 22:
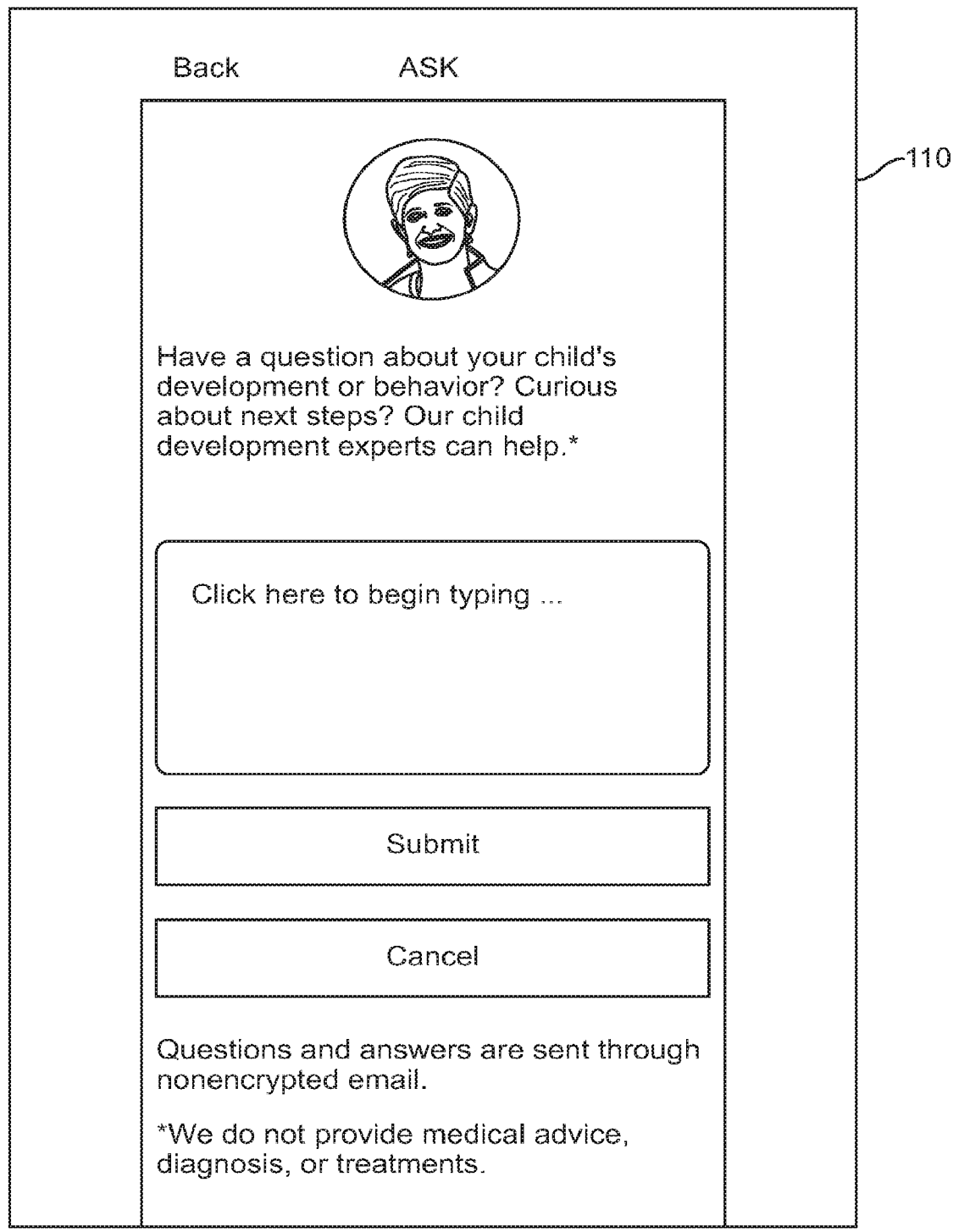
FIG. 22 shows a graphical user interface for use with a digital personalized medicine platform that allows a user to ask a medical professional questions regarding their child, in accordance with some embodiments.

FIG. 22 shows a graphical user interface for use with a digital personalized medicine platform that allows a user to ask a medical professional questions regarding their child. The user digital device 110 may display a field for entering any questions that a user may have regarding their child's development. For instance, the user digital device may allow a user to ask questions regarding their child's development or behavior and/or next steps following an assessment of their child.

Figure 23:
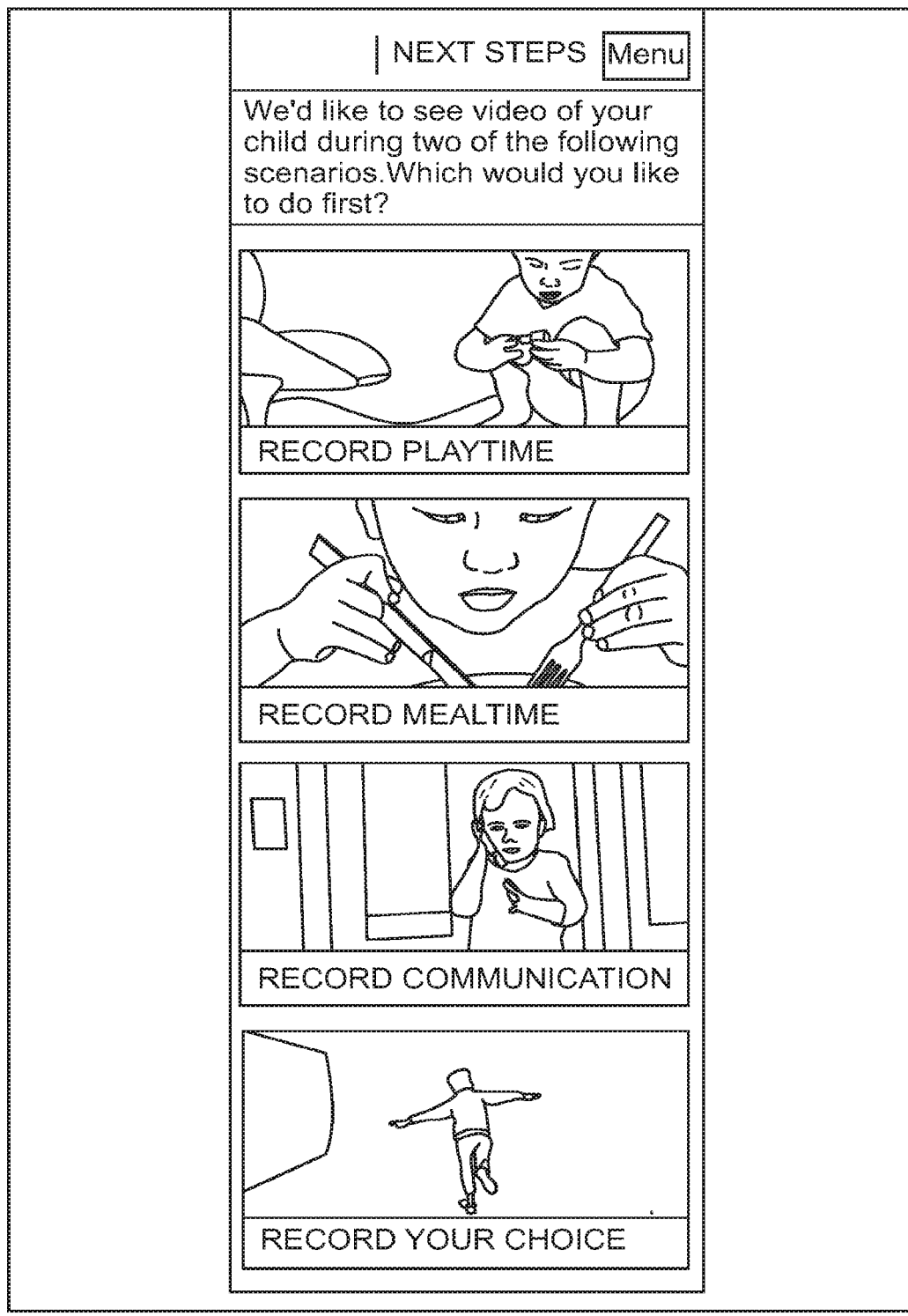
FIG. 23 shows a graphical user interface for use with a digital personalized medicine platform that prompts a user to submit video of their child engaging in activities, in accordance with some embodiments.

FIG. 23 shows a graphical user interface for use with a digital personalized medicine platform that prompts a user to submit video of their child engaging in activities. The user digital device 110 may display a prompt asking the user to submit one or more videos of their child engaging in certain activities and one or more buttons that allow the user to record and/or upload video. The user digital device may display a button allowing a user to record and/or upload a video of their child engaging in playtime, a button allowing a user to record and/or upload a video of their child engaging in mealtime, a button allowing a user to record and/or upload a video of their child engaging in communication, and/or a button allowing a user to record and/or upload a video of their child engaging in an activity of the user's choice.

Figure 24:
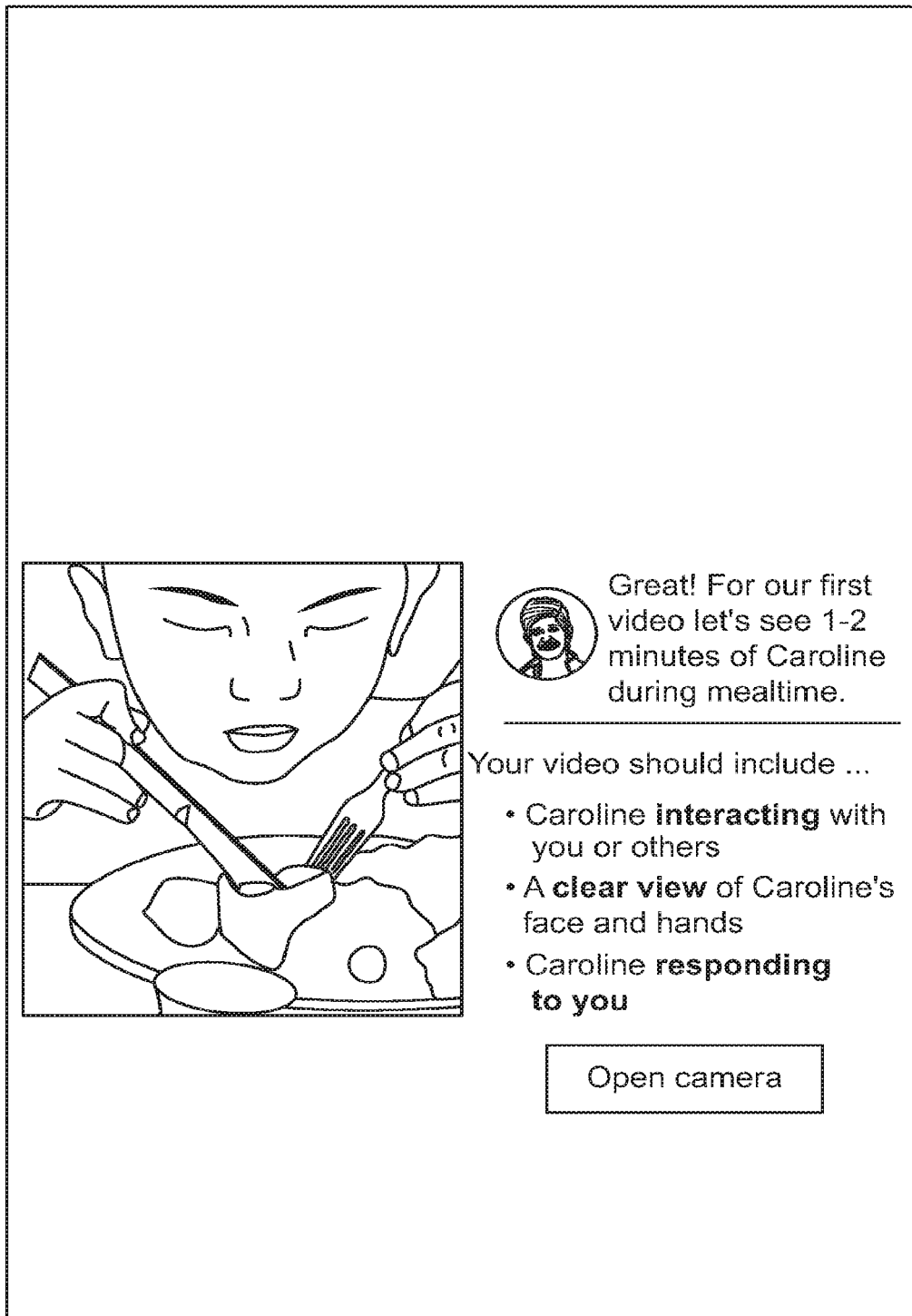
FIG. 24 shows a graphical user interface for use with a digital personalized medicine platform that instructs a user regarding how to submit video of their child engaging in activities, in accordance with some embodiments.

FIG. 24 shows a graphical user interface for use with a digital personalized medicine platform that instructs a user regarding how to submit video of their child engaging in activities. The user digital device 110 may display a set of instructions for recording a user's child engaging in activities. The user digital device may display a set of instructions for obtaining more than 1 minute, more than 2 minutes, more than 3 minutes, more than 4 minutes, or more than 5 minutes of video of the child during playtime, during mealtime, during communication, and/or during an activity of the user's choice. The user digital device may display instructions that the video should include the user's child interacting with the user and/or other people, that the video should include a clear view of the child's face and hands, and/or that the video should show the child interacting with the user. The user digital device may display a button for opening the user's camera to record the video.

Figure 25:
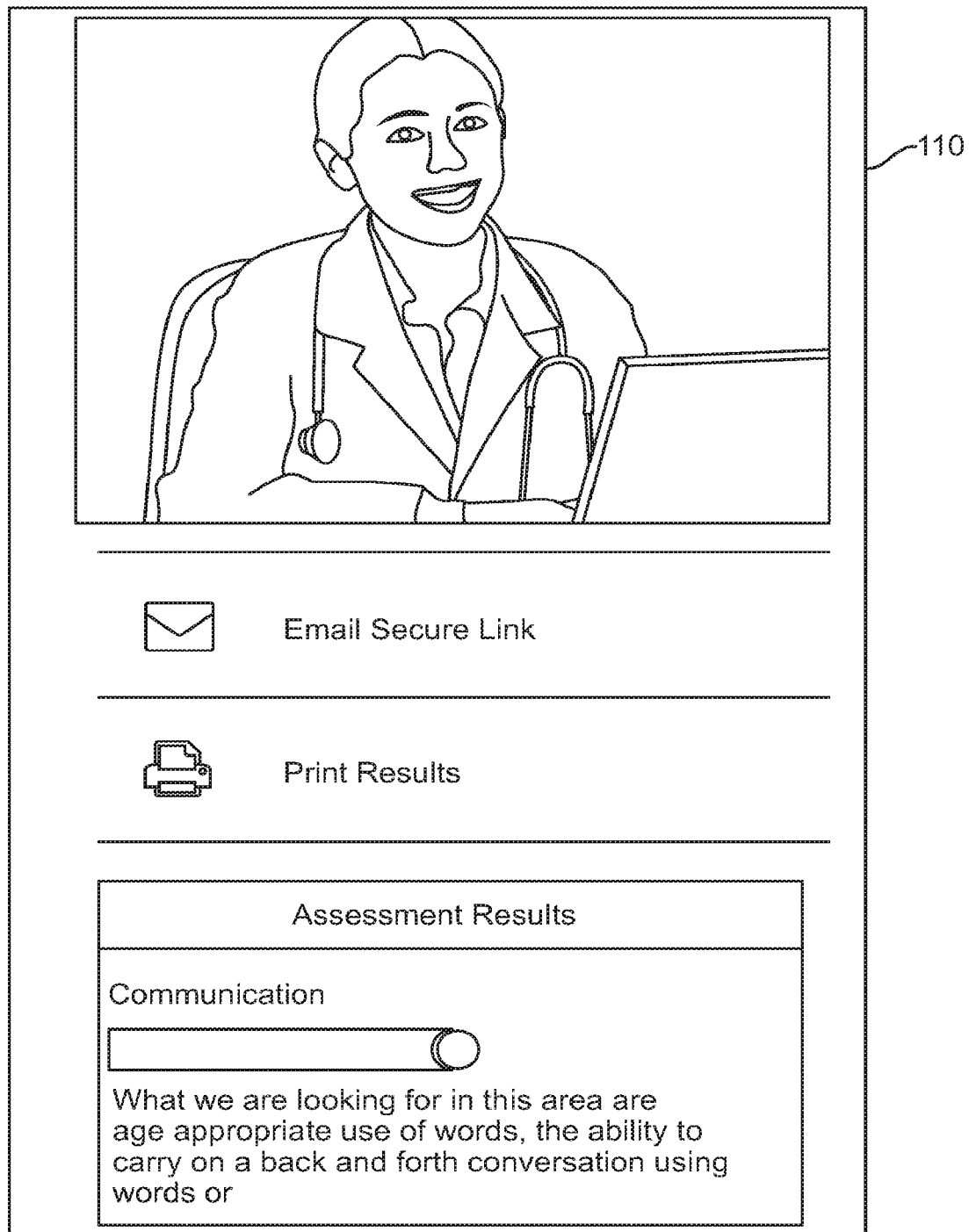
FIG. 25 shows a graphical user interface for use with a digital personalized medicine platform that allows a user to submit diagnostic information to medical professional, in accordance with some embodiments.

FIG. 25 shows a graphical user interface for use with a digital personalized medicine platform that allows a user to submit diagnostic information to medical professional. The user digital device 110 may display a button allowing a user to email assessment results to a medical professional and/or a button allowing a user to print assessment results.

Figure 26:
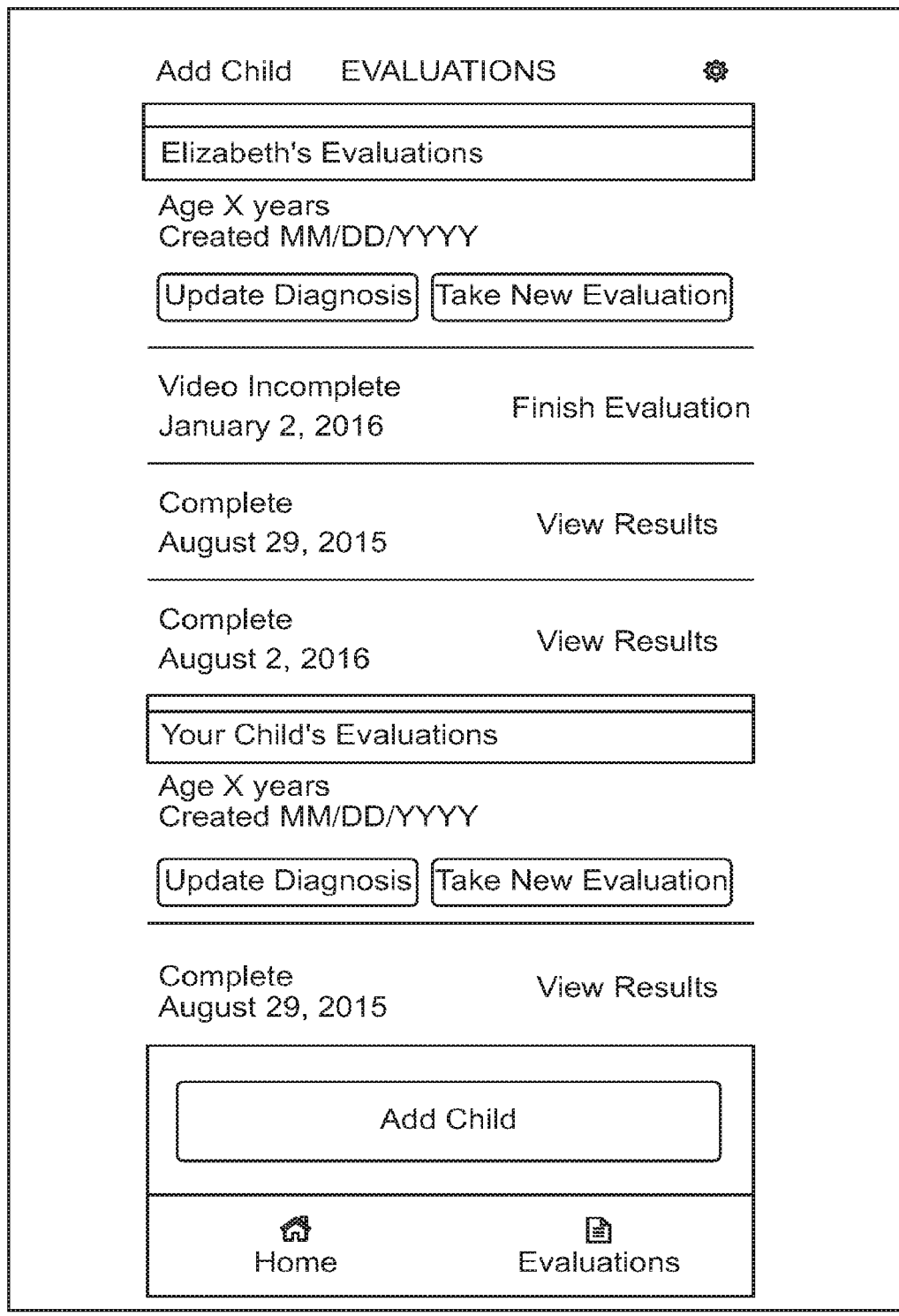
FIG. 26 shows a graphical user interface for use with a digital personalized medicine platform that shows a profile for a user's child, in accordance with some embodiments.

FIG. 26 shows a graphical user interface for use with a digital personalized medicine platform that shows a profile for a user's child. The user digital device 110 may display information regarding the age of a user's child and/or the date on which a profile for the child was created. The user digital device may display a button allowing a user to update a diagnosis and/or a button allowing a user to take a new evaluation. The user digital device may display one or more buttons allowing a user to access one or more partially or fully completed assessments. For instance, the user digital device may display one or more button allowing a user to access an incomplete evaluation (such as a video) and the ability to finish that evaluation, as well as one or more buttons allowing a user to access prior completed evaluations.

Figure 27:
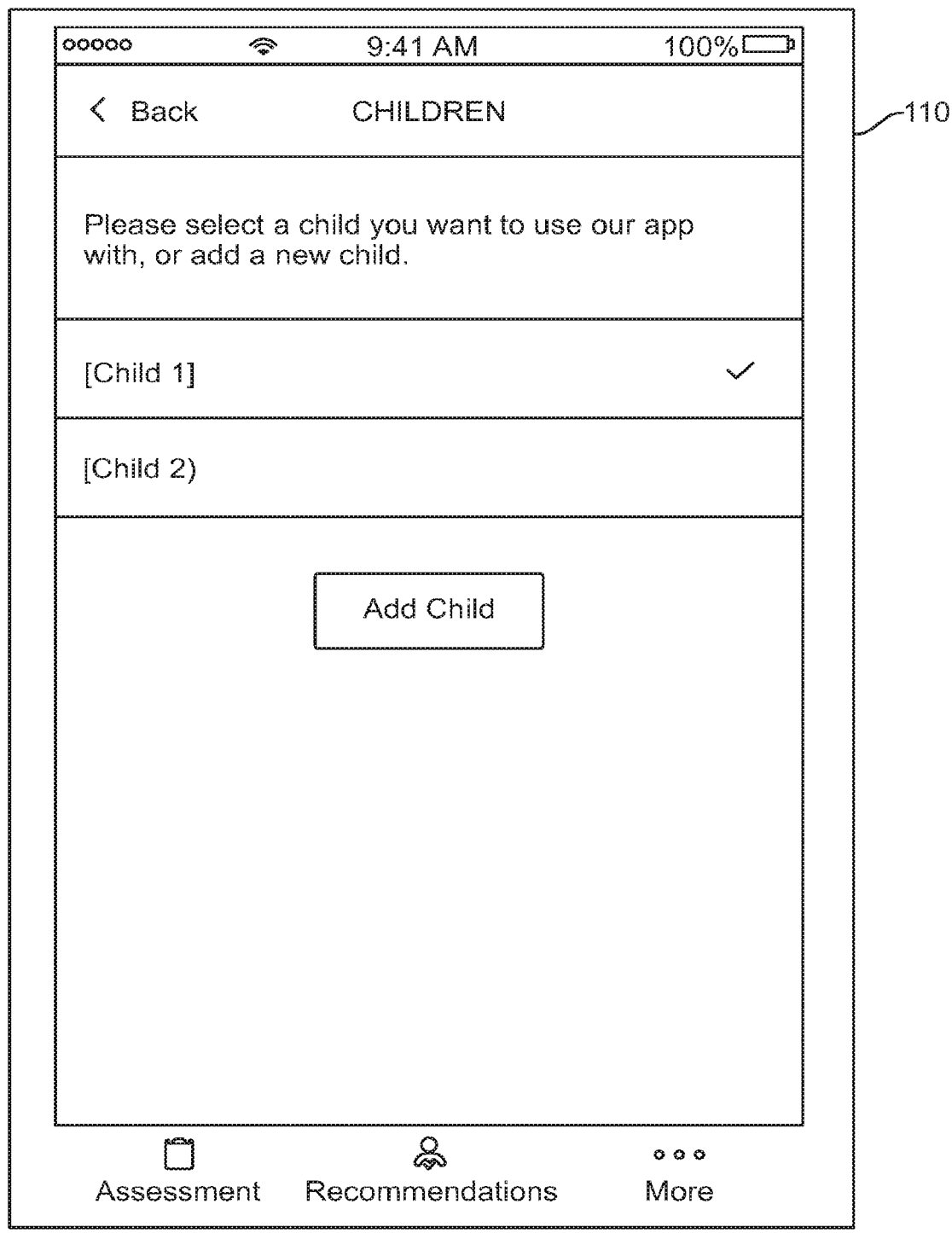
FIG. 27 shows a graphical user interface for use with a digital personalized medicine platform that allows a user to select between different profiles, in accordance with some embodiments.

FIG. 27 shows a graphical user interface for use with a digital personalized medicine platform that allows a user to select between different profiles. The user digital device 110 may display one or more selection fields that allow a user to select between previously created profiles for each of the user's children. The user digital device may display a button allowing a user to add a profile for another child.

Figure 28:
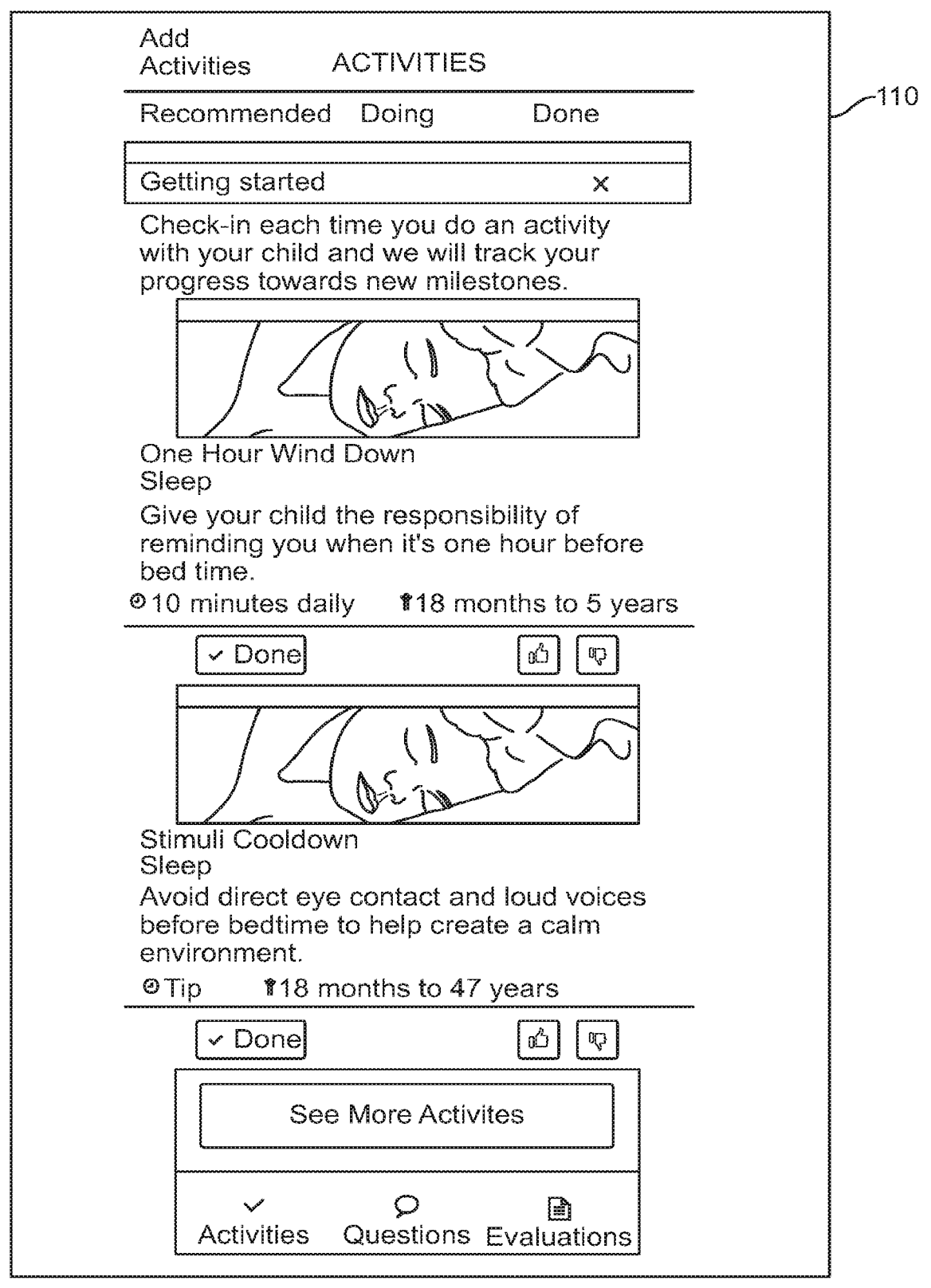

FIG. 28 shows a graphical user interface for use with a digital personalized medicine platform that provides suggestions to a user regarding activities that their child can perform to alleviate symptoms associated with their child's diagnosis. The user digital device 110 may display a listing of one or more activities that a user's child may be performing for therapeutic purposes. The user digital device may display buttons allowing a user to select activities that have been recommended, activities that the child is doing, and/or activities that the child has already done. The user digital device may display a prompt telling the user to check in each time the user performs an activity with their child. The user digital device may display one or more activities that have been recommended, that the child is doing, and/or that the child has done. For instance, the user digital display device may display a one hour wind down activity with a prompt to have a user give their child the responsibility of reminding the user when bedtime is an hour away. The user digital device may display a stimuli cooldown activity with a prompt to have a user avoid eye contact and loud voices before bedtime to help create a calm environment. The user digital device may display a button allowing a user to see more activities.

Experimental Data

A data processing module as described herein was built on Python 2.7, Anaconda Distribution. The training data used to construct and train the assessment model included data generated by the Autism Genetic Resource Exchange (AGRE), which performed in-home assessments to collect ADI-R and ADOS data from parents and children in their homes. ADI-R comprises a parent interview presenting a total of 93 questions, and yields a diagnosis of autism or no autism. ADOS comprises a semi-structured interview of a child that yields a diagnosis of autism, ASD, or no diagnosis, wherein a child is administered one of four possible modules based on language level, each module comprising about 30 questions. The data included clinical diagnoses of the children derived from the assessments; if a single child had discrepant ADI-R versus ADOS diagnoses, a licensed clinical psychologist assigned a consensus diagnosis for the dataset for the child in question. The training data included a total of 3,449 data points, with 3,315 cases (autism or ASD) and 134 controls (non-spectrum). The features evaluated in the training data targeted 3 key domains: language, social communication, and repetitive behaviors.

A boosted Random Forest classifier was used to build the assessment model as described herein. Prior to training the assessment model on the training data, the training data was pre-processed to standardize the data, and re-encode categorical features in a one-hot representation as described herein. Since the training data was skewed towards individuals with autism or ASD, sample weighting was applied to attribute up to 50 times higher significance to data from non-spectrum individuals compared to data from autistic/ASD individuals. The assessment model was trained iteratively with boosting, updating the weighting of data points after each iteration to increase the significance attributed to data points that were misclassified, and retraining with the updated significances.

Figure 29:
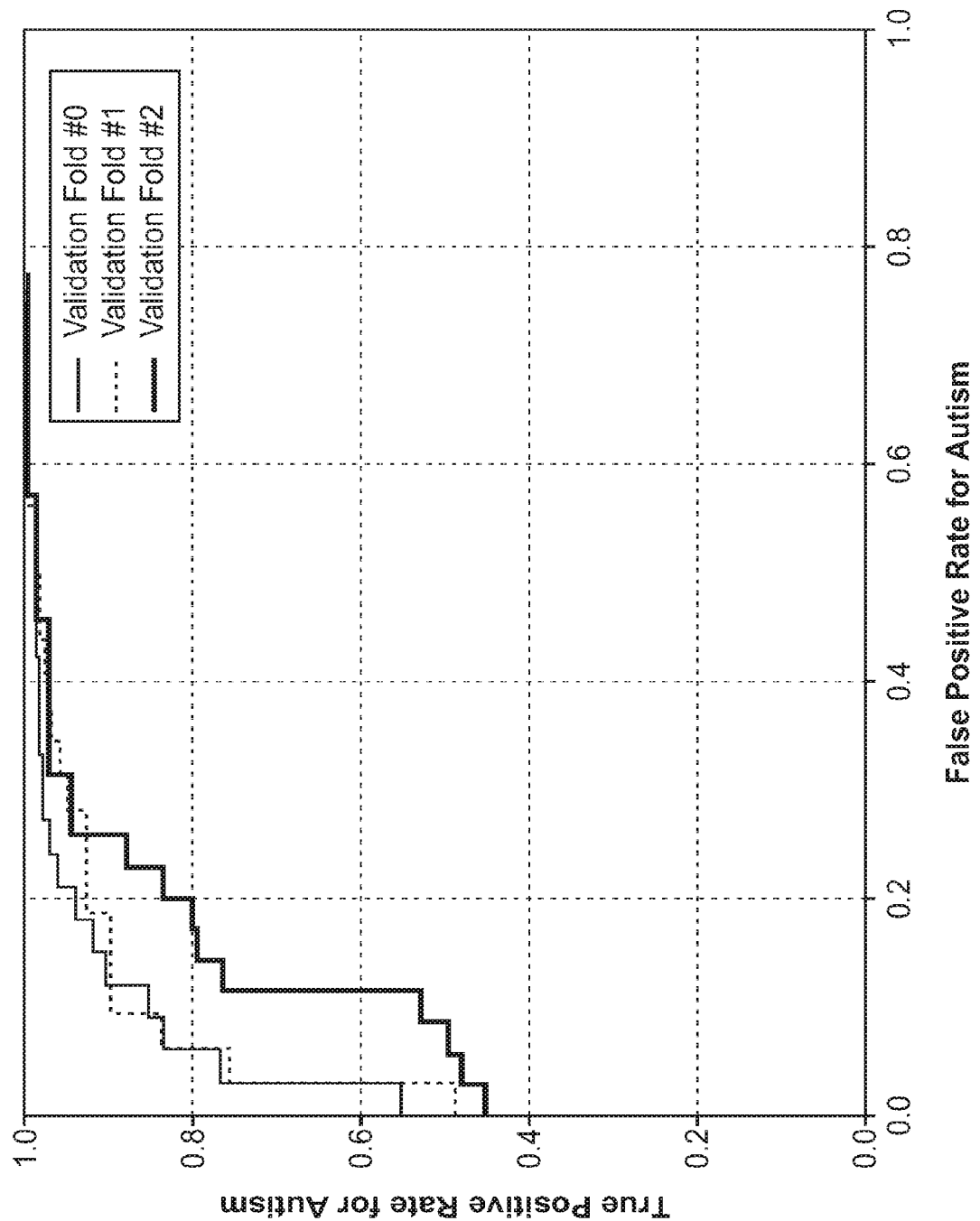
FIG. 29 shows receiver operating characteristic (ROC) curves mapping sensitivity versus fall-out for an exemplary assessment model as described herein, in accordance with some embodiments.

The trained model was validated using Stratified k-fold cross validation with k=5. The cross-validation yielded an accuracy of about 93-96%, wherein the accuracy is defined as the percentage of subjects correctly classified using the model in a binary classification task (autism/non-spectrum). Since the training data contained a sample bias, a confusion matrix was calculated to determine how often the model confused one class (autism or non-spectrum) with another. The percentage of correctly classified autism individuals was about 95%, while the percentage of correctly classified non-spectrum individuals was about 76%. It should be noted, however, that the model may be adjusted to more closely fit one class versus another, in which case the percentage of correct classifications for each class can change. FIG. 29 shows receiver operating characteristic (ROC) curves mapping sensitivity versus fall-out for an exemplary assessment model as described herein. The true positive rate (sensitivity) for the diagnosis of autism is mapped on the y-axis, as a function of the false positive rate (fall-out) for diagnosis mapped on the x-axis. Each of the three curves, labeled "Fold #0", "Fold #1", and "Fold #2", corresponds to a different "fold" of the cross-validation procedure, wherein for each fold, a portion of the training data was fitted to the assessment model while varying the prediction confidence threshold necessary to classify a dataset as "autistic". As desired or appropriate, the model may be adjusted to increase the sensitivity in exchange for some increase in fall-out, or to decrease the sensitivity in return for a decrease in fall-out, as according to the ROC curves of the model.

Figure 30:
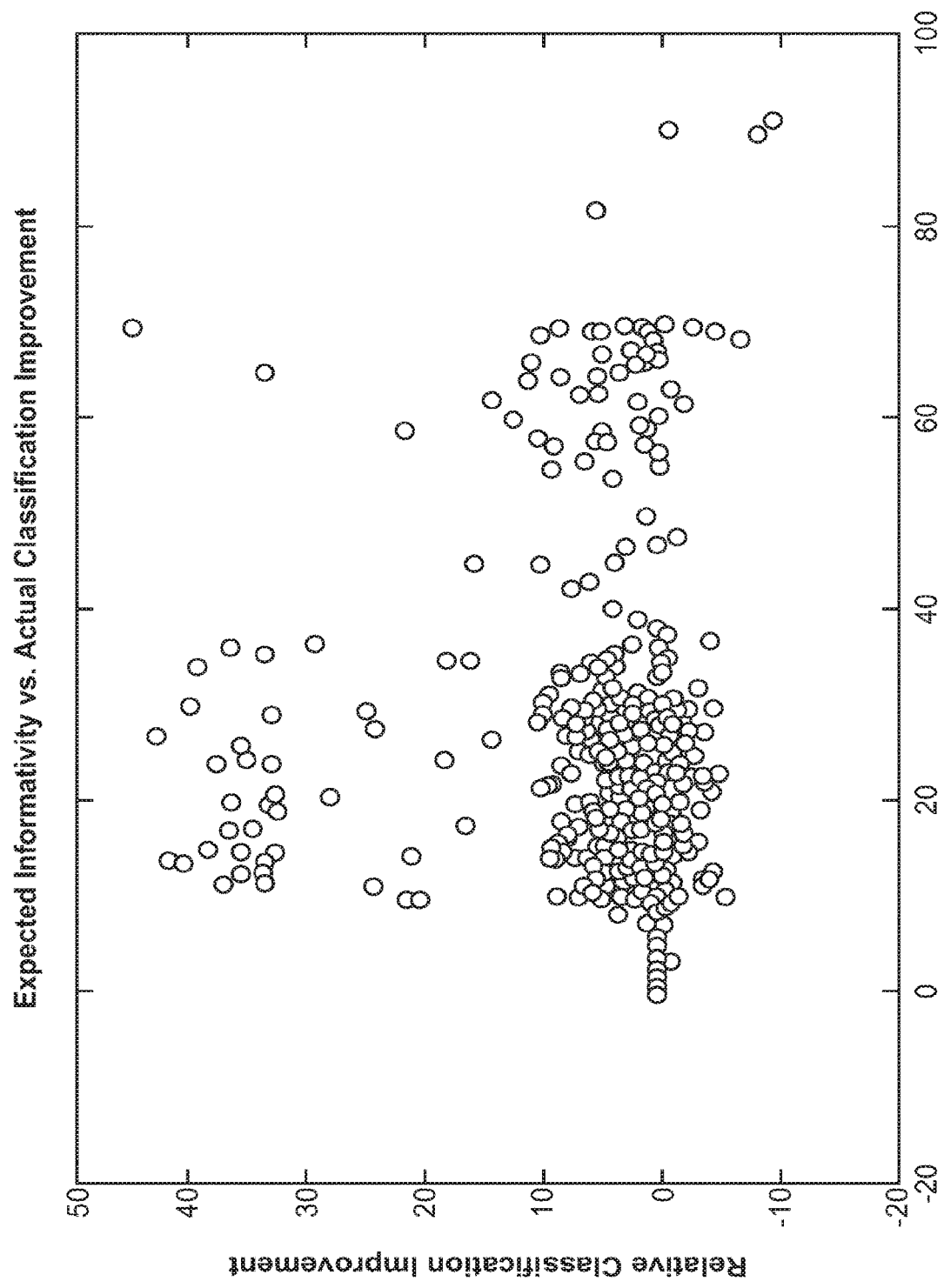
FIG. 30 is a scatter plot illustrating a performance metric for a feature recommendation module as described herein, in accordance with some embodiments.

The feature recommendation module was configured as described herein, wherein the expected feature importance of each question was computed, and candidate questions ranked in order of computed importance with calls to a server with an application program interface (API). The feature recommendation module's ability to recommend informative questions was evaluated by determining the correlation between a question's recommendation score with the increase in prediction accuracy gained from answering the recommended question. The following steps were performed to compute the correlation metric: (1) the data was split up into folds for cross-validation; (2) already answered questions were randomly removed from the validation set; (3) expected feature importance (question recommendation/score) was generated for each question; (4) one of the questions removed in step 2 was revealed, and the relative improvement in the subsequent prediction accuracy was measured; and (5) the correlation between the relative improvement and the expected feature importance was computed. The calculated Pearson correlation coefficient ranged between 0.2 and 0.3, indicating a moderate degree of correlation between the expected feature importance score and the relative improvement. FIG. 30 is a scatter plot showing the correlation between the expected feature importance ("Expected Informativitiy Score") and the relative improvement ("Relative Classification Improvement") for each question. The plot shows a moderate linear relationship between the two variables, demonstrating the feature recommendation module is indeed able to recommend questions that would increase the prediction accuracy.

The length of time to produce an output using the developed prediction module and the feature recommendation model was measured. The prediction module took about 46 ms to make a prediction of an individual's risk of autism. The feature recommendation module took about 41 ms to generation question recommendations for an individual. Although these measurements were made with calls to a server through an API, the computations can be performed locally, for example.

While the assessment model of the data processing module described with respect to FIGS. 9-10 was constructed and trained to classify subjects as having autism or no autism, a similar approach may be used to build an assessment model that can classify a subject as having one or more of a plurality of behavioral, neurological or mental health disorders, as described herein.

A person of ordinary skill in the art can generate and obtain additional datasets and improve the sensitivity and specificity and confidence interval of the methods and apparatus disclosed herein to obtain improved results without undue experimentation. Although these measurements were performed with example datasets, the methods and apparatus can be configured with additional datasets as described herein and the subject identified as at risk with a confidence interval of 80% in a clinical environment without undue experimentation. The sensitivity and specificity of 80% or more in a clinical environment can be similarly obtained with the teachings provided herein by a person of ordinary skill in the art without undue experimentation, for example with additional datasets.

Additional datasets may be obtained from large archival data repositories as described herein, such as the Autism Genetic Resource Exchange (AGRE), Boston Autism Consortium (AC), Simons Foundation, National Database for Autism Research, and the like. Alternatively or in combination, additional datasets may comprise mathematically simulated data, generated based on archival data using various simulation algorithms. Alternatively or in combination, additional datasets may be obtained via crowd-sourcing, wherein subjects self-administer the assessment procedure as described herein and contribute data from their assessment. In addition to data from the self-administered assessment, subjects may also provide a clinical diagnosis obtained from a qualified clinician, so as to provide a standard of comparison for the assessment procedure.

Although the detailed description contains many specifics, these should not be construed as limiting the scope of the disclosure but merely as illustrating different examples and aspects of the present disclosure. It should be appreciated that the scope of the disclosure includes other embodiments not discussed in detail above. Various other modifications, changes and variations which will be apparent to those skilled in the art may be made in the arrangement, operation and details of the method and apparatus of the present disclosure provided herein without departing from the spirit and scope of the invention as described herein. For example, one or more aspects, components or methods of each of the examples as disclosed herein can be combined with others as described herein, and such modifications will be readily apparent to a person of ordinary skill in the art. For each of the methods disclosed herein, a person of ordinary skill in the art will recognize many variations based on the teachings described herein. The steps may be completed in a different order. Steps may be added or deleted. Some of the steps may comprise sub-steps of other steps. Many of the steps may be repeated as often as desired, and the steps of the methods can be combined with each other.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A computer-implemented method for determining a timing or a dosage of a drug for treating a human subject having autism or autism spectrum disorder, said method comprising:
   (a) receiving subject data for said human subject, wherein said subject data comprises information for said autism or autism spectrum disorder, demographic data of said human subject, metabolic data of said human subject, pharmacokinetic data of said human subject, clearance data of said human subject, or microbiome data of said human subject;
   (b) generating diagnostic data based on said subject data received for said human subject, wherein said diagnostic data is generated with a diagnostic module;
   (c) determining said timing or said dosage of said drug that achieves in said human subject a target blood concentration level of said drug, wherein said timing or said dosage is determined with a therapeutic module that uses said diagnostic data to determine said timing or said dosage; and
   (d) treating said human subject with said drug by providing said drug to said human subject at said dosage or with said timing that is determined in (c) to achieve said target blood concentration level of said drug.

2. The method of claim 1, wherein said diagnostic data comprises an assessment of cognitive function of said subject.

3. The method of claim 1, further comprising receiving updated subject data, generating updated diagnostic data based on said updated subject data, and determining an updated dosage or updated timing of said drug that achieves in said human subject said target blood concentration level of said drug.

4. The method of claim 1, wherein (d) further comprises treating said human subject with a digital therapy.

5. The method of claim 4, wherein said treating said human subject with said digital therapy comprises providing a timing or a dosage of said digital therapy.

6. The method of claim 4, wherein said digital therapy comprises digital activities or games.

7. The method of claim 6, further comprising obtaining an active or passive data stream from interaction with said digital activities or games by said human subject, and updating said timing or said dosage of said drug based at least on said active or passive data stream.

8. The method of claim 1, wherein said pharmacokinetic data of said human subject is determined in response to administering a known amount of said drug to said human subject at a first time and determining said blood level of said drug or a metabolite thereof at a second time.

9. The method of claim 1, wherein said clearance data of said human subject is determined using a beta clearance rate of said drug in said human subject, and wherein said beta clearance rate is estimated using said demographic data of said human subject.

10. The method of claim 1, further comprising receiving updated subject data for said human subject in response to said treating in (d) and generating an updated dosage or an updated timing of said drug for said human subject using said therapeutic module.

11. The method of claim 10, further comprising treating said human subject with said drug at said updated dosage or said updated timing.

12. The method of claim 1, further comprising determining a treatment efficacy of said treating in (d).

13. The method of claim 12, further comprising displaying a plurality of questions related to at least one of a behavior or a cognitive function of said human subject after said treating in (d), and wherein said treatment efficacy is determined at least in part from answers to said plurality of questions.

14. The method of claim 12, further comprising determining a treatment response profile of said drug, wherein said treatment response profile comprises said blood level of said drug over time, and comparing said treatment response profile with at least one target therapeutic amount of said drug, thereby determining said treatment efficacy of said drug.

15. The method of claim 1, further comprising evaluating a behavior or a performance of said human subject using said diagnostic module, wherein said diagnostic module uses answers to a plurality of questions related to said autism or autism spectrum disorder.

16. The method of claim 1, further comprising sending said timing or said dosage to a first digital device of said human subject.

17. The method of claim 16, further comprising providing treatment monitoring through a second digital device of a secondary observer.

18. The method of claim 16, wherein said first digital device comprises a smartphone.

19. The method of claim 1, wherein said subject data comprises an alpha elimination half-life of said drug or a beta elimination half-life of said drug.

20. The method of claim 1, wherein said subject data comprises metabolic data of said human subject for creatinine, xanthine, hypoxanthine, inosine, LTB4, guanosine, 1-methylnicotinamide, 11-dehydro-thromboxane B2, 4-hydroxyphenyllactic acid, L-cystine, hexanoylcarnitine, dihexosylceramide, ceramide, 2,3-diphosphoglyceric acid, phosphatidyl inositol, cysteine-glutathione disulfide, D-glucose, trihexosylceramide, bismonoacylphospholipid, malondialdehyde, phosphatidylcholine, 3,5-tetradecadiencamitine, epoxy-5,8,11-eicosatrienoic acid, cardiolipin, 8,9-epoxyeicosatrienoic acid, myristoylcarnitine, cholic acid, octanoylcarnitine, pimelylcarnitine, dodecynoylcarnitine, L-homocysteic acid, 9-decenoylcarnitine, hydroxyisocaproic acid, propionic acid, 5-alpha-cholestanol, glyceric acid 1,3-biphosphate, 3-methylphenylacetic acid, cytidine, oxaloacetic acid, 9-hexadecenoylcarnitine, dehydroisoandrosterone 3-sulfate, 11-R-hydroxyeicosatetraenoic acid, pyridoxamine, 11,12-dihydroxyeicosatrienoic acid, sedoheptulose 7-phosphate, 5-aminoimidazole-4-carboxamide ribonucleotide, or any combination thereof.

* * * * *